US00RE47009E

(19) United States
(12) Reissued Patent
Kozikowski et al.

(10) Patent Number: US RE47,009 E
(45) Date of Reissued Patent: Aug. 28, 2018

(54) HDAC INHIBITORS AND THERAPEUTIC METHODS USING THE SAME

(71) Applicants: THE CHILDREN'S HOSPITAL OF PHILADELPHIA, Philadelphia, PA (US); THE TRUSTEES OF THE UNIVERSITY OF ILLINOIS, Urbana, IL (US)

(72) Inventors: Alan Kozikowski, Chicago, IL (US); Jay Hans Kalin, Chicago, IL (US); Kyle Vincent Butler, Stanford, CA (US); Joel Bergman, Chicago, IL (US); Wayne W. Hancock, Philadelphia, PA (US)

(73) Assignees: THE CHILDREN'S HOSPITAL OF PHILADELPHIA, Philadelphia, PA (US); THE TRUSTEES OF THE UNIVERSITY OF ILLINOIS, Urbana, IL (US)

(21) Appl. No.: 15/182,061

(22) Filed: Jun. 14, 2016

Related U.S. Patent Documents

Reissue of:

(64) Patent No.: 9,249,087
Issued: Feb. 2, 2016
Appl. No.: 13/985,760
PCT Filed: Jan. 31, 2012
PCT No.: PCT/US2012/023332
§ 371 (c)(1),
(2) Date: Dec. 20, 2013
PCT Pub. No.: WO2012/106343
PCT Pub. Date: Aug. 9, 2012

U.S. Applications:

(60) Provisional application No. 61/438,435, filed on Feb. 1, 2011, provisional application No. 61/443,960, filed on Feb. 17, 2011, provisional application No. 61/554,653, filed on Nov. 2, 2011.

(51) Int. Cl.

| | |
|---|---|
| ***A61K 31/497*** | (2006.01) |
| ***A61K 49/00*** | (2006.01) |
| ***C07C 259/10*** | (2006.01) |
| ***A61K 51/04*** | (2006.01) |
| ***C07C 229/52*** | (2006.01) |
| ***C07D 207/30*** | (2006.01) |
| ***C07D 209/04*** | (2006.01) |
| ***A61K 31/405*** | (2006.01) |
| ***C07D 235/06*** | (2006.01) |
| ***C07D 207/323*** | (2006.01) |
| ***C07D 209/08*** | (2006.01) |
| ***C07D 209/14*** | (2006.01) |
| ***C07D 213/56*** | (2006.01) |
| ***C07D 231/12*** | (2006.01) |
| ***C07D 473/00*** | (2006.01) |
| ***C07D 209/18*** | (2006.01) |
| ***C07D 209/20*** | (2006.01) |
| ***A61K 45/06*** | (2006.01) |
| ***C07D 207/08*** | (2006.01) |

(52) U.S. Cl.

CPC ..... *C07C 229/52* (2013.01); *A61K 45/06* (2013.01); *A61K 49/0002* (2013.01); *A61K 51/04* (2013.01); *A61K 51/0446* (2013.01); *A61K 51/0453* (2013.01); *A61K 51/0455* (2013.01); *A61K 51/0459* (2013.01); *C07C 259/10* (2013.01); *C07D 207/08* (2013.01); *C07D 207/323* (2013.01); *C07D 209/08* (2013.01); *C07D 209/14* (2013.01); *C07D 209/18* (2013.01); *C07D 209/20* (2013.01); *C07D 213/56* (2013.01); *C07D 231/12* (2013.01); *C07D 235/06* (2013.01); *C07D 473/00* (2013.01); *C07C 2101/08* (2013.01)

(58) Field of Classification Search

CPC ..... C07C 229/52

See application file for complete search history.

(56) References Cited

U.S. PATENT DOCUMENTS

| | | | |
|---|---|---|---|
| 4,923,865 | A | 5/1990 | Cossement et al. |
| 6,541,661 | B1 | 4/2003 | Delorme et al. |
| 9,249,087 | B2 | 2/2016 | Kozikowski et al. |
| 2005/0154201 | A1 | 7/2005 | Chen et al. |
| 2008/0200521 | A1 | 8/2008 | Neogi et al. |
| 2008/0207590 | A1 | 8/2008 | Deziel et al. |
| 2008/0319012 | A1 | 12/2008 | Kim et al. |
| 2010/0093743 | A1 | 4/2010 | Finn et al. |

FOREIGN PATENT DOCUMENTS

| | | | |
|---|---|---|---|
| EP | 0341231 | A1 | 11/1989 |
| EP | 0887348 | A1 | 12/1998 |
| WO | WO-00/18744 | A1 | 4/2000 |
| WO | WO-01/70675 | A2 | 9/2001 |
| WO | WO-03/076422 | A1 | 9/2003 |
| WO | WO-2007/022638 | A1 | 3/2007 |
| WO | WO-2008/019025 | A2 | 2/2008 |
| WO | WO-2008/055068 | A2 | 5/2008 |
| WO | WO-2009/046804 | A1 | 4/2009 |
| WO | WO-2009/055917 | A1 | 5/2009 |
| WO | WO-2009/073620 | A2 | 6/2009 |
| WO | WO-2010/100475 | A1 | 9/2010 |
| WO | WO-2011/011186 | A2 | 1/2011 |
| WO | WO-2011/021209 | A1 | 2/2011 |
| WO | WO-2012/178208 | A2 | 12/2012 |

OTHER PUBLICATIONS

Brown et al., Molecular addition compounds. 4. Unusually slow reaction of tertiary amines with 9-borabicyclo[3.3.1]nonane (9-BBN) dimer. New, stable, mildly reactive amine complexes of 9-BBN, Inorg. Chem., 16(12):3090-4 (1977).

(Continued)

*Primary Examiner* — Johnny F Railey

(74) *Attorney, Agent, or Firm* — Marshall, Gerstein & Borun LLP

(57) ABSTRACT

Histone deacetylases inhibitors (HDACIs) and compositions containing the same are disclosed. Methods of treating diseases and conditions wherein inhibition of HDAC provides a benefit, like a cancer, a neurodegenerative disorder, a peripheral neuropathy, a neurological disease, traumatic brain injury, stroke, hypertension, malaria, an autoimmune disease, autism, autism spectrum disorders, and inflammation, also are disclosed.

11 Claims, 2 Drawing Sheets

(56) References Cited

OTHER PUBLICATIONS

Chai et al., Metal-mediated inhibition is a viable approach for inhibiting cellular methionine aminopeptidase, Bioorg. Med. Chem. Lett., 19(24):6862-4 (2009).
Dell'Erba et al., alpha-Arylation vs. alpha-arylhydrazonylation of alkyl aryl ketones with arylazo tert-butyl sulfides, Tetrahedron, 49(1):235-42 (1993).
Esterbauer, Synthese einiger 4-hydroxy-2-alkenale, Monatsheft für Chemie, 102:824-7 (1971).
Faul et al., A new one step synthesis of maleimides by condensation of glyoxylate esters with acetamides, Tetrahedron Lett., 40:1109-12 (1999).
Kawase et al., In vitro susceptibility of helicobacter pylori to trifluoromethyl ketones, Bioorg. Med. Chem. Lett., 9:193-4 (1999).
Kitazume et al., A synethetic approach to seven-membered lactones by the microbial transformation of ynones having a trifluoromethyl group, J. Fluorine Chem., 30:189-202(1985).
Kon-ya et al., Indole derivatives as potent inhibitors of larval settlement by the barnacle, *Balanus* amphitrite, Biosci. Biotech. Biochem., 58(12):2178-81 (1994).
Lautens et al., Rhodium-catalyzed heck-type coupling of boronic acids with activated alkenes in an aqueous emulsion, Synthesis, 12:2006-14 (2004).
Morand et al., The effect of substituted carboxylic acids on hepatic cholesterogenesis, J. Med. Chem., 7:504-8 (1964).
Nelson et al., Synthesis and antiinflammatory activity of some 1,6-methano[10]annuleneacetic acids, J. Med. Chem., 18(6):593- 6 (1975).
Remiszewski et al., N-hydroxy-3-phenyl-2-propenamides as novel inhibitors of human histone deacetylase with in vivo antitumor activity: discovery of (2E)-N-hydroxy-3-[4-[[(2-hydroxyethyl)[2-(1H-indol-3-yl)ethyl]amino]methyl]phenyl]-2-propenamide (NVP-LAQ824), J. Med. Chem., 46(21):4609-24 (2003).
Smith et al., e-Anilino-4-arylmaleimides: potent and selective inhibitors of glycogen synthase kinase-3 (GSK-3), Bioorg. Med. Chem. Lett., 11:635-9 (2001).
Suzuki, Explorative study on isoform-selective histone deacetylase inhibitors, Chem. Pharm. Bull., 47(9):897-906 (2009).
CAS Registry No. 3360-46-1; STN Entry Date Nov. 16, 1984.
CAS Registry No. 854631-63-3; STN Entry Date Jul. 12, 2005.
CAS Registry No. 864408-96-8; STN Entry Date Oct. 4, 2005.
Cossement et al., [Mivazerol and other benzylimidazoles with alpha-2 adrenergic properties], J. Pharm. Belg., 49(3):206-15 (1994).
Examination Report No. 2 for Standard Patent Application, Australian Patent Application No. 2012212323, dated Feb. 16, 2017.
Examination Report, European patent application No. EP 12742236.8, dated Mar. 9, 2017.
Yee et al., A novel series of selective leukotriene antagonists: exploration and optimization of the acidic region in 1,6-disubstituted indoles and indazoles, J. Med. Chem., 33(9):2437-51 (1990).
Nyandege, Abner, et al., "Further Studies on the Binding of N1-Substituted Tryptamines at h5-HT6 Receptors," Bioorganic & Medicinal Chemistry Letters, 2007, vol. 17, pp. 1691-1694.
Tang, H., et al., "Novel Inhibitors of Human Histone Deacetylase (HDAC) Identified by QSAR Modeling of Known Inhibitors, Virtual Screening, and Experimental Validation," *Journal of Chemical Information Modeling.*, 2009, vol. 49, No. 2, pp. 461-476.
International Search Report in international patent application No. PCT/US2012/023332, dated Aug. 7, 2012.
Examination Report, European patent application No. 12742236.8, dated Apr. 29, 2015.
Headley et al., Effects of solvents on the tautomerization of N,N-dimethylglycine, J. Phys. Org. Chem., 10:898-900 (1997).
Takagi et al., Synthesis of indolyl aryl 1,2-diketones, Pharm. Bull., 5(6):617-8 (1957).

HDAC INHIBITORS AND THERAPEUTIC METHODS USING THE SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is the U.S. National phase of PCT/US2012/023332, filed Jan. 31, 2012, which claims the benefit of U.S. provisional application No. 61/438,435, filed Feb. 1, 2011, U.S. provisional application No. 61/443,960, filed Feb. 17, 2011, and U.S. provisional application No. 61/554,653, filed Nov. 2, 2011, each incorporated herein by reference in its entirety.

STATEMENT OF GOVERNMENT INTEREST

This invention was made with government support under NIH Grant No. P01AI073489 awarded by the National Institutes of Health. The government has certain rights in the invention.

FIELD OF THE INVENTION

The present invention relates to histone deacetylase (HDAC) inhibitors, to pharmaceutical compositions comprising one or more of the HDAC inhibitors, to methods of increasing the sensitivity of cancer cells to the cytotoxic effects of radiotherapy and/or chemotherapy comprising contacting the cell with one or more of the HDAC inhibitors, and to therapeutic methods of treating conditions and diseases wherein inhibition of HDAC provides a benefit, for example, a cancer, an inflammation, a neurological disease, a neurodegenerative disorder, stroke, traumatic brain injury, allograft rejection, autoimmune diseases, and malaria, comprising administering a therapeutically effective amount of a present HDAC inhibitor to an individual in need thereof.

BACKGROUND OF THE INVENTION

Inhibitors of HDACs modulate transcription and induce cell growth arrest, differentiation, and apoptosis. HDAC inhibitors (HDACIs) also enhance the cytotoxic effects of therapeutic agents used in cancer treatment, including radiation and chemotherapeutic drugs. Moreover, recent research indicates that transcriptional dysregulation may contribute to the molecular pathogenesis of certain neurodegenerative disorders, such as Huntington's disease, Rett syndrome, Charcot-Marie-Tooth disease (CMT) and other peripheral neuropathies, spinal muscular atrophy, amyotropic lateral sclerosis, and ischemia. For example, suberoylanilide hydroxamic acid (SAHA) has been shown to penetrate into the brain to dramatically improve motor impairment in a mouse model of Huntington's disease, thereby validating research directed to HDACIs in the treatment of neurodegenerative diseases. Furthermore, selective HDAC6 inhibitors have been shown to rescue the CMT phenotype, restore proper mitochondrial motility, and correct the axonal transport defects observed in transgenic mice. Selective HDAC6 inhibitors also induce the re-innervation of muscles and increase the number of observed neuromuscular junctions in these same models (C. d'Ydewalle et al., Nature Medicine 2011).

A recent review summarized evidence that aberrant histone acetyltransferase (HAT) and HDAC activity may be a common underlying mechanism contributing to neurodegeneration. Moreover, from a mouse model of depression, the therapeutic potential of HDACs in treating depression is discussed. See WO 2008/019025, designating the United States, incorporated herein in its entirety.

Eleven isozymes in the HDAC family of enzymes, which can be grouped into classes by their evolutionary relationships, have been identified. Structure and function appear to be conserved among members of the various classes. The HDAC family is made up of class I HDACs, including HDAC1, 2, 3, and 8; class IIa, including HDAC4, 5, 7, and 9; class IIb, including HDAC6 and 10; and a class IV enzyme, HDAC11 (A. J. de Ruijter et al., The Biochemical Journal 2003, 370(Pt), 737-749).

The class I HDACs are found primarily in the nucleus and are expressed in all tissue types, except for the muscle cell-specific HDAC8. The class I HDACs interact with many key transcription factors regulating gene expression, including CoREST and NuRD. Class IIa HDACs have tissue specific expression, and are found in both the nucleus and cytoplasm. Unlike the other isozymes, the class IIb HDAC6 does not extensively associate with transcription factors, and acts as a deacetylase on non-histone proteins, including α-tubulin, HSP90, cortactin, and the peroxiredoxins (O. Witt et al., Cancer Letters 2008; R. B. Parmigiana et al., PNAS 2008).

HDACs form multiprotein complexes with many regulatory proteins inside the cell. For example, HDAC4, 5, and 7 actually lack intrinsic deacetylase ability, and gain activity only by interacting with HDAC3. Each isozyme interacts with a specific series of regulatory proteins and transcription factors and has a specific set of substrates, and thus each regulates a specific series of genes and proteins (O. Witt et al., Cancer Letters 2008). The design of selective HDAC isozyme inhibitors allows preferential inhibition of only the isozyme(s) relevant to a particular disease or condition, thereby reducing the probability of counterproductive and/or adverse effects resulting from an unwanted and undesired inhibition of other HDAC isozymes.

HDAC6 is the most abundant histone deacetylase isozyme in the human body, and along with HDAC7, is the most commonly expressed isozyme in the brain (A. J. de Ruijter et al., The Biochemical Journal 2003, 370(Pt), 737-749). Structurally significant features of HDAC6 include two deacetylase domains and a zinc finger motif. It is most commonly found in the cytoplasm, but can be shuttled into the nucleus via its nuclear export signal. A cytoplasmic retention signal, which sequesters the enzyme in the cytoplasm, also was found (A. Valenzuela-Fernandez et al., Trends in Cell Biology 2008, 18(6), 291-297). The functions of HDAC6 are unlike any of the other HDAC isozymes.

Many non-histone substrates are deacetylated by HDAC6, including α-tubulin, HSP90, cortactin, and peroxiredoxins (O. Witt et al., Cancer Letters 2008; R. B. Parmigiani et al., PNAS USA 2008, 105 (28), 9633-9638).

The design of HDACIs focuses on the three major domains of the enzyme molecule. A zinc binding group (ZBG) of the HDACI typically is a hydroxamic acid, benzamide, or thiol, although other functional groups have been used. This ZBG moiety of the inhibitor chelates the zinc cofactor found in the active site of the enzyme. The ZBG moiety typically is bonded to a lipophilic linker group, which occupies a narrow channel leading from the HDAC surface to the active site. This linker, in turn, is bonded to a surface recognition, or 'cap', moiety, which typically is an aromatic group that interacts with residues at the surface of the enzyme (K. V. Butler et al., Current Pharmaceutical Design 2008, 14(6), 505-528).

Consideration of each structural element is important in the design of HDACIs (37). Alteration of the ZBG has profound effects on inhibitor potency. The most potent inhibitors frequently feature a hydroxamic acid ZBG, though other groups such as ketones, amides, and thiols effectively inhibit the enzyme with lower potency. Low molecular weight compounds having carboxylic acid ZBGs, such as valproic acid, inhibit HDACs at micromolar potency, but have profound effects in vivo when given in high doses. Hydroxamic acids chelate zinc in a bidentate fashion and hydrogen bond with H142 and H143 (HDAC8), as revealed by crystal structure data. Computational studies have refined this description of chelation, demonstrating that the hydroxamic acid carbonyl coordinates zinc more strongly than the hydroxyl group. Energetically favorable interactions between hydroxamic acid and the active site provide for high potency inhibition, but the hydroxamic acid functional group has some undesirable properties from a drug design perspective. Hydroxamic acids are potentially mutagenic, and have given positive results in the Ames test. Hydroxamic acids also are promiscuous zinc chelators and potently inhibit many zinc-containing metalloproteins. The replacement of hydroxamic acid with a different potent ZBG is an active area of research in HDACI design and development.

The linker region typically is a hydrophobic aryl or alkyl scaffold, which occupies the hydrophobic HDAC catalytic channel. Most reported HDACIs, including SAHA, feature an alkyl chain linker, mimicking the lysine alkyl chain. Aromatic groups are frequently included in the linker region of an HDACI, for example, in the HDACIs panbinostat and belinostat.

Manipulation of the cap group can greatly increase potency because this group has the potential to interact with multiple residues at the enzyme surface. The most potent inhibitors typically feature an aryl cap group scaffold. Biaryl and heteroaromatic cap group scaffolds have been extensively investigated. The large tetrapeptide motif of apicidin imparts high potency, and gives high potency with a number of diverse ZBGs. The tetrapeptide cap group motif is common to natural product HDACIs, and has been engineered to produce libraries of tetrapeptide HDACIs for use in screening protocols.

Currently, at least eleven HDACIs are in clinical development. These HDACIs can be divided into at least five chemical classes, illustrated below, based on their structure, and in most cases they broadly and nonselectively inhibit class I/II HDACs with varying efficiency. These five chemical classes are hydroxamates, cyclic tetrapeptides, cyclic peptides, short-chain fatty acids, and benzamides. Typically, known HDACIs fail to show prominent HDAC isozyme selectivity, which as stated above can cause serious problems in a clinical setting, especially in the treatment of diseases and conditions wherein a prolonged drug administration of an HDACI is required. For example, it has been found that some HDACIs enhance lung and microglial inflammation (TSA and SAHA), as well as high glucose-induced inflammation. If this effect is linked to specific HDAC isozymes, the use of certain HDACIs would be contraindicated in various diseases and conditions, such as diabetes and asthma.

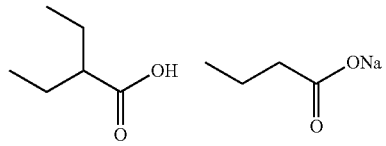

Valproic acid Sodium butyrate

Aliphatic acids

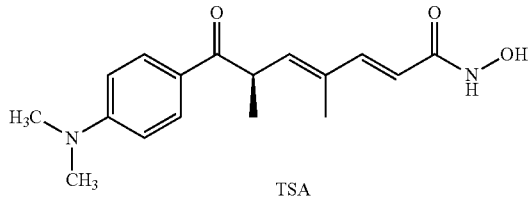

TSA

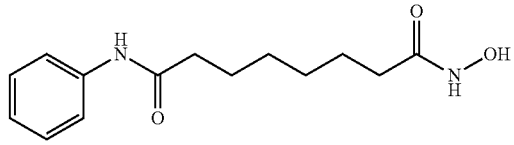

SAHA

Hydroxamate

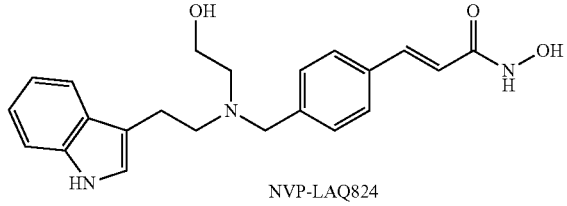

NVP-LAQ824

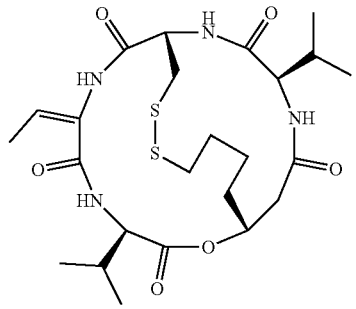

Depsipeptide

Cyclic peptide

-continued

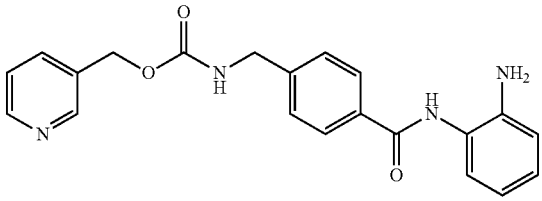

MS-275

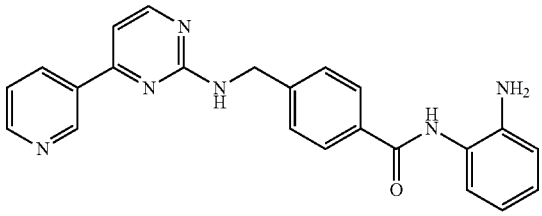

MGCD0103

Benzamide

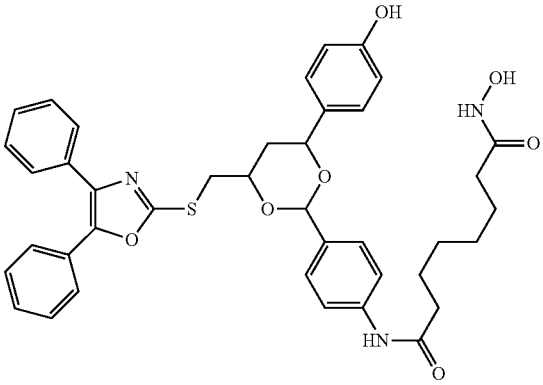

Tubacin

Other

Classes of HDAC inhibitors

Additional HDACI's include

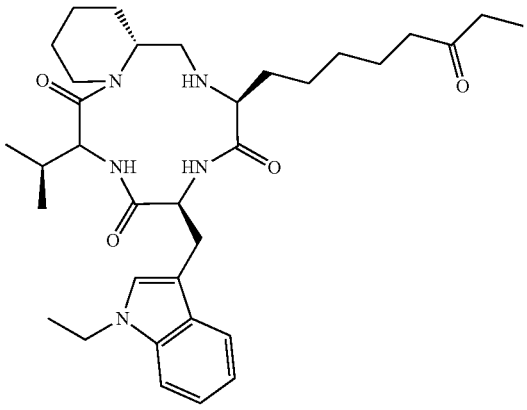

Apicidin
Natural Product

-continued

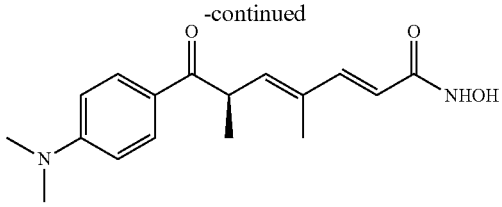

Trichostatin A
Natural Product

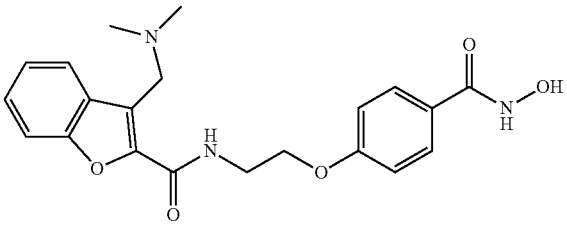

PCI-24781
Synthetic

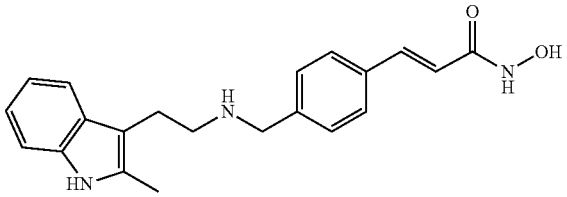

Panbinostat
Synthetic

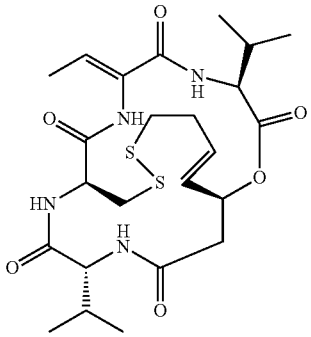

Romidepsin
Natural Product

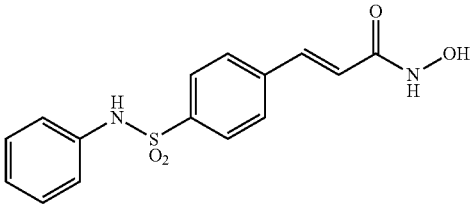

Belinostat
Synthetic

The following table summarizes some HDACIs that presently are in clinical trials.

TABLE I

| Inhibitor | Indications |
|---|---|
| SAHA | T-cell lymphoma (Approved) |
| Romidepsin | T-cell lymphoma (Approved) |
| | Multiple myeloma (Phase III) |
| | Peripheral T-cell lymphoma (Phase III) |
| | Refractory renal cell cancer (Phase II) |

TABLE I-continued

| Inhibitor | Indications |
|---|---|
| Valproic Acid | Bipolar disorder (Approved) |
| | Acute myeloid leukemia (Phase I/II with all trans-retinoic acid) |
| PCI-24781 | Leukemia (Phase I/II) |
| ITF-2357 | Hodgkins lymphoma (Phase II) |
| | Follicular lymphoma (Phase III, with yttrium-90-ibritumomab) |
| | Juvenile arthritis (Phase II) |
| | Myeloproliferative Diseases (Phase II) |
| MS-275 | Melanoma |
| | Lymphoma (halted due to dose limiting toxicities) |
| | Advanced acute leukemias (Phase 1) |
| | Combination trials with DNA methyltransferase inhibitors and 5-azacitidine in non-small cell lung cancer (Preclinical) |
| Panbinostat | T-cell lymphoma (Phase II) |
| | Prostate cancer (Phase I with docetaxel) |
| Belinostat | Solid tumors (Phase I) |
| | Mesothelioma (Abandoned) |
| MGCD0103 | Solid tumors (Phase II with gemcitabine) |
| | Diffuse large B-cell lymphoma (Phase II) |
| EVP-0334 | Parkinson's disease (Phase I) |

Clinical trial information relating to HDACIs is published in J. Tan et al., Journal of hematology & oncology. 3:5 (2010) and L. Wang et al., Nat Rev Drug Discov. 8:969-81 (2009).

HDAC-regulated factors have been implicated in the mechanisms of major central nervous system (CNS) disorders. In Parkinson's disease (PD), α-synuclein binds to histones and inhibits HAT activity, causing neurodegeneration. Application of HDACIs to PD neurons blocks α-synuclein toxicity. Dysregulation of histone acetylation, involving CBP, a neuroprotective transcription factor with histone acetyltransferase activity, has been found in Huntington's disease (HD), Alzheimer's disease (AD), and Rubinstein-Taybi syndrome (T. Abel et al., Curr. Opin. in Pharmacol. 2008, 8(1), 57-64). In a cellular model of AD, cell death was accompanied by loss of CBP function and histone deacetylation. The mutant HD protein, htt, interacts with CBP, inhibiting the HAT activity and causing cell death. Treatment with an HDACI helps to restore histone acetylation, protecting against neurodegeneration and improving motor performance in a mouse model of HD (C. Rouaux et al., Biochem. Pharmacol. 2004, 68(6), 1157-1164).

Various studies directed to the application of HDACIs in the context of CNS disorders have implicated the class II HDACs, particularly HDAC6, as potential therapeutic targets. One investigation revealed that inhibition of HDAC6 could be beneficial as a treatment for HD, a disease for which no pharmacological treatment is available. The mutant htt protein found in HD disrupts intracellular transport of the pro-survival and pro-growth nerve factor, BDNF, along the microtubule network, causing neuronal toxicity. Inhibition of HDAC6 promotes transport of BDNF by promoting tubulin hyperacetylation. TSA (trichostatin A), a nonselective HDAC inhibitor, was found to facilitate transport and release of BNDF-containing vesicles (J. P. Dompierre et al., J Neurosci 2007, 27(13), 3571-3583). These results provide a biological basis for the identification and development of HDACIs, and particularly HDAC6 selective inhibitors, as a treatment for HD and other neurodegenerative disorders.

HDACIs prevent or delay neuronal dysfunction and death in in vitro and in vivo models thereby indicating that HDACIs are broadly neuroprotective. For example, HDACIs have shown therapeutic efficacy in the polyglutamine-expansion disorder Huntington's disease. While the neuroprotective mechanisms of the HDACIs in rodent models are not yet understood, it is clear that HDACIs induce the expression of certain genes that confer neuroprotection. The upregulation of HSP-70 and Bcl-2 through the inhibition of HDAC has been observed in the cortex and striatum of rats after focal cerebral ischemia. HSP-70 expression has been found to result in neuroprotection in a number of disease models including Alzheimer's disease (AD), Parkinson's disease (PD), and Huntington's disease (HD). In addition, HDAC6 inhibition leads to the acetylation of peroxiredoxin and increases its antioxidant activity which may contribute to the neuroprotective effects of these compounds (R. B. Parmigiana et al., PNAS 2008).

Studies also provide good evidence that HDACI-induced p21cip1/waf1 expression may play a significant role in HDACI-mediated neuroprotection. It recently was reported that p21cip1/waf1 overexpression protects neurons from oxidative stress-induced death, that p21cip1/waf1 is induced in the rodent brain by HDAC inhibition, and that homozygous loss of p21cip1/waf1 exacerbates damage in a mouse MCAO/reperfusion model of ischemic stroke. In a similar study, the HDAC inhibitor TSA was shown to increase gelsolin expression in neurons, and that gelsolin expression is necessary for neuroprotection in an oxygen/glucose deprivation model of neurodegeneration and a mouse MCAO/reperfusion model of ischemic stroke.

Alternatively, unrelated to histone acetylation and gene upregulation, proteins such as α-tubulin and HSP90 are targets for acetylation and become acetylated when HDACs are inhibited. In tumor cells, the acetylation of HSP90 has been shown to decrease the ability of HSP90 to interact with certain client proteins and thereby abrogate chaperone function. With regard to stroke and traumatic brain injury (TBI), as well as several other neurodegenerative diseases, the inhibition of HSP90 is predicted to have a positive effect on neuronal survival. Indeed, the pharmacological HSP90 inhibitor, Geldanamycin, and its analogs have been shown to be neuroprotective in a number of stroke models. HSP90 inhibition and the consequent release of heat-shock factor (HSF) to the nucleus may also, in part, explain an upregulation of HSP70 in the brain during focal ischemia and HDACI treatment.

In addition, HDACIs are useful in the treatment of cancers. For example, histone acetylation and deacetylation play important roles in chromatin folding and maintenance (Kornberg et al., Bjorklund et al., Cell, 1999, 96:759-767; Struhl et al., Cell, 1998, 94:1-4). Acetylated chromatin is more open and has been implicated in the increased radiation sensitivities observed in some cell types (Oleinick et al., Int. J. Radiat. Biol. 1994, 66:523-529). Furthermore, certain radiation-resistant human cancer cells treated with the HDACI inhibitor TSA were sensitized to the damaging effects of ionizing radiation. Thus, HDACIs appear useful as radiation sensitizing agents.

WO 2008/055068, designating the U.S. and incorporated herein in its entirety, discloses numerous diseases and conditions treatable by HDACIs, including the underlying science and reasoning supporting such treatments.

HDAC6 therefore has emerged as an attractive target for drug development and research. (C. M. Grozinger et al., Proc. Natl. Acad. Sci. USA 1999, 96, 4868-73; and C. Boyault et al., Oncogene 2007, 26, 5468-76.) Presently, HDAC6 inhibition is believed to offer potential therapies for autoimmunity, cancer, and many neurodegenerative conditions. (S. Minucci et al., Nat. Rev. Cancer. 2006, 6, 38-51; L. Wang et al., Nat. Rev. Drug Discov. 2009, 8, 969-81; J.

P. Dompierre et al., J. Neurosci. 2007, 27, 3571-83; and A. G. Kazantsev et al., Nat. Rev. Drug Discov. 2008, 7, 854-68.) Selective inhibition of HDAC6 by small molecule or genetic tools has been demonstrated to promote survival and re-growth of neurons following injury, offering the possibility for pharmacological intervention in both CNS injury and neurodegenerative conditions. (M. A. Rivieccio et al., Proc. Natl. Acad. Sci. USA 2009, 106, 19599-604.) Unlike other histone deacetylases, inhibition of HDAC6 does not appear to be associated with any toxicity, making it an excellent drug target. (O. Witt et al., Cancer Lett 2009, 277, 8-21.) Tubacin, an HDAC6 selective inhibitor, used in models of disease, has helped to validate, in part, HDAC6 as a drug target, but its non-drug-like structure, high lipophilicity (ClogP=6.36 (KOWWIN)) and tedious synthesis make it more useful as a research tool than a drug. (S. Haggarty et al., Proc. Natl. Acad. Sci. USA 2003, 100, 4389-94.) Other compounds also have a modest preference for inhibiting HDAC6. (S. Schafer et al., ChemMedChem 2009, 4, 283-90; Y. Itoh et al., J. Med. Chem. 2007, 50, 5425-38; and S. Manku et al., Bioorg. Med. Chem. Lett. 2009, 19, 1866-70.)

In summary, extensive evidence supports a therapeutic role for HDACIs in the treatment of a variety of conditions and diseases, such as cancers and CNS diseases and degenerations. However, despite exhibiting overall beneficial effects, like beneficial neuroprotective effects, for example, HDACIs known to date have little specificity with regard to HDAC inhibition, and therefore inhibit all zinc-dependent histone deacetylases. It is still unknown which is (are) the salient HDAC(s) that mediate(s) neuroprotection when inhibited. Emerging evidence suggests that at least some of the HDAC isozymes are absolutely required for the maintenance and survival of neurons, e.g., HDAC1. Additionally, adverse side effect issues have been noted with nonspecific HDAC inhibition. Thus, the clinical efficacy of present-day nonspecific HDACIs for stroke, neurodegenerative disorders, neurological diseases, and other diseases and conditions ultimately may be limited. It is important therefore to design, synthesize, and test compounds capable of serving as potent, and preferably isozyme-selective, HDACIs that are able to ameliorate the effects of neurological disease, neurodegenerative disorder, traumatic brain injury, cancer, inflammation, malaria, autoimmune diseases, immunosuppressive therapy, and other conditions and diseases mediated by HDACs.

An important advance in the art would be the discovery of HDACIs, and particularly selective HDAC6 inhibitors, that are useful in the treatment of diseases wherein HDAC inhibition provides a benefit, such as cancers, neurological diseases, traumatic brain injury, neurodegenerative disorders and other peripheral neuropathies, stroke, hypertension, malaria, allograft rejection, rheumatoid arthritis, and inflammations. Accordingly, a significant need exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention relates to HDACIs, pharmaceutical compositions comprising the HDACIs, and methods of treating diseases and conditions wherein inhibition of HDAC provides a benefit, such as a cancer, a neurological disease, a neurodegenerative disorder, a peripheral neuropathy, stroke, hypertension, an inflammation, traumatic brain injury, rheumatoid arthritis, allograft rejection, autoimmune diseases, and malaria, comprising administering a therapeutically effective amount of an HDACI to an individual in need thereof. The present invention also relates to a method of increasing the sensitivity of a cancer cell to radiotherapy and/or chemotherapy. The present invention also allows for the use of these HDACIs inhibitors in combination with other drugs and/or therapeutic approaches. In some embodiments, the present HDACIs exhibit selectivity for particular HDAC isozymes, such as HDAC6, over other HDAC isozymes.

More particularly, the present invention relates to HDACIs having a structural formula:

Cap-L-M wherein Cap is selected from the group consisting of (a)

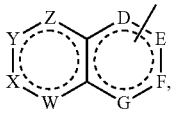

wherein ring

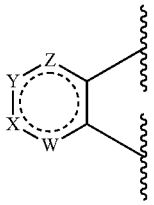

is an aliphatic or aromatic five or six membered ring,

W, X, Y, and Z independently are selected from the group consisting of null, $C(R^1)_2$, O, S, and $NR^1$, ring

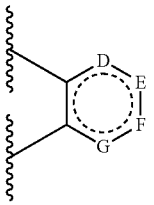

is an aliphatic or aromatic five or six membered ring,

D, E, F, and G independently are selected from the group consisting of null, $C(R^1)_2$, O, S, and $NR^1$, $R^1$, independently, is selected from the group consisting of null, hydrogen, $C_{1-6}$alkyl, $C_{1-6}$heteroalkyl, $C_{2-6}$alkenyl, $C_{1-6}$perfluoroalkyl, $C_{1-6}$ perfluoroalkoxy, aryl, heteroaryl, $C_{3-10}$cycloalkyl, $C_{3-10}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

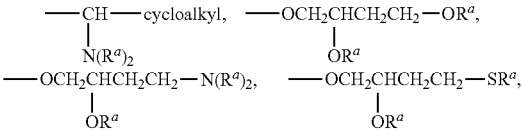

$OR^a$, halo, $N(R^a)_2$, $SR^a$, $SOR^a$, $SO_2R^a$, CN, $C(=O)R^a$, $CF_3$, $OCF_3$, $NO_2$, $OC(=O)R^a$, $SO_2N(R^a)_2$, $OSO_2CF_3$, C(=O)

$OR^a$, $C(=O)N(R^a)_2$, $C_{1-6}alkyleneN(R^a)_2$, $C_{1-6}alkyleneC(=O)R^a$, $C_{1-6}alkyleneOR^a$, $C_{1-6}alkyleneSR^a$, $C_{1-6}alkyleneNR^aSO_2R^a$, $C_{1-6}alkyleneSOR^a$, $C_{1-6}alkyleneCN$, $C_{1-6}heteroalkyleneCN$, $C_{1-6}alkyleneC(=O)OR^a$, $C_{1-6}alkyleneOC(=O)N(R^a)_2$, $C_{1-6}alkyleneNR^aC(=O)OR^a$, $C_{1-6}alkyleneNR^aC(=O)R^a$, $C_{1-6}alkylene\ C(=O)N(R^a)_2$, $C_{1-6}alkyleneOC_{1-6}alkyleneC(=O)OR^a$, $C(=O)NR^aSO_2R^a$, $C(=O)C_{1-6}alkylenearyl$, $C(=O)NR^aC_{1-6}alkyleneOR^a$, $OC_{1-6}alkyleneC(=O)OR^a$, $OC_{1-6}alkyleneN(R^a)_2$, $OC_{1-6}alkyleneOR^a$, $OC_{1-6}alkyleneNR^aC(=O)OR^a$, $NR^aC_{1-6}alkyleneN(R^a)_2$, $NR^aC(=O)R^a$, $NR^aC(=O)N(R^a)_2$, $N(SO_2C_{1-6}alkyl)_2$, and $NR^a(SO_2C_{1-6}alkyl)$, and $R^a$, independently, is selected from the group consisting of hydrogen, $C_{1-6}alkyl$, $C_{1-6}heteroalkyl$, $C_{1-6}alkyleneNH_2$, $C_{1-6}alkyleneNH(C_{1-6}alkyl)$, $C_{1-6}alkyleneN(C_{1-6}alkyl)_2$, $C_{1-6}alkyleneNH(C_{1-6}alkyl)_2$, $C_{1-6}alkyleneNHC(=O)(C_{1-6}alkyl)$, $C_{1-6}alkyleneC(=O)NH_2$, $C_{1-6}alkyleneOH$, $C_{1-6}alkyleneCN$, $C_{1-6}heteroalkyleneCN$, $C_{1-6}alkyleneOC_{1-6}alkyl$, $C_{1-6}alkyleneSH$, $C_{1-6}alkyleneSC_{1-6}alkyl$, $C_{1-6}alkyleneNH(SO_2C_{1-6}alkyl)$, aryl, heteroaryl, $C_{3-8}cycloalkyl$, and $C_{3-10}heterocycloalkyl$, (b)

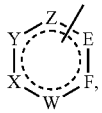

wherein ring

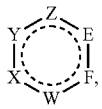

is an aliphatic or aromatic five or six membered ring,

E, F, W, X, Y, Z, $R^1$, and $R^a$ are as defined above, and (c)

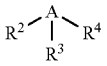

wherein A is C, N, O, S, B, or P, and L is attached to A, $R^2$, $R^3$ and $R^4$ independently are selected from the group consisting of null, hydrogen, $C_{1-6}alkyl$, $C_{1-6}heteroalkyl$, $C_{2-6}alkenyl$, $C_{1-6}perfluoroalkyl$, $C_{1-6}perfluoroalkoxy$, aryl, heteroaryl, $C_{3-10}cycloalkyl$, $C_{3-8}heterocycloalkyl$, $C_{1-6}alkylenearyl$, $C_{1-6}alkyleneheteroaryl$, $C_{1-6}alkyleneheterocycloalkyl$, $C_{1-6}alkylenecycloalkyl$,

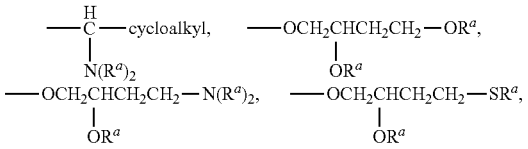

$OR^a$, halo, $N(R^a)_2$, $SR^a$, $SOR^a$, $SO_2R^a$, CN, $C(=O)R^a$, $OC(=O)R^a$, $C(=O)OR^a$, $C_{1-6}alkyleneN(R^a)_2$, $C_{1-6}alkyleneOR^a$, $C_{1-6}alkyleneSR^a$, $C_{1-6}alkyleneC(=O)OR^a$, $C(=O)N(R^a)_2$, $C(=O)NR^aC_{1-6}alkyleneOR^a$, $OC_{1-6}alkyleneC(=O)OR^a$, $OC_{1-6}alkyleneN(R^a)_2$, $OC_{1-6}alkyleneOR^a$, $OC_{1-6}alkyleneNR^aC(=O)OR^a$, $NR^aC_{1-6}alkyleneN(R^a)_2$, $NR^aC(=O)R^a$, $NR^aC(=O)N(R^a)_2$, $N(SO_2C_{1-6}alkyl)_2$, $NR^a(SO_2C_{1-6}alkyl)$, nitro, and $SO_2N(R^a)^2$, and $R^a$ is defined above;

L is selected from the group consisting of null, $C_{1-8}alkylene$, $R^a$ substituted $C_{1-8}alkylene$, $NR^a$, C(=O), aryl, C(=O)aryl, $C(=O)C_{1-6}alkylene$, $C_{1-8}alkyleneNR^a$, $C_{1-6}alkylenearyleneC_{1-6}alkylene$, $C_{2-6}alkenylene$, $C_{4-8}alkdienylene$, $C_{1-6}alkylenearylene$, $C_{1-6}alkyleneheteroarylene$, $R^a$ substituted $C_{1-6}alkyleneheteroarylene$, and $C_{2-6}alkenylenearyleneC_{1-6}alkylene$, and $R^a$ is defined above;

M is selected from the group consisting of $—C(=O)N(R^b)OH$, $—O(CH_2)_{1-6}C(=O)N(R^b)OR^b$, $—N(R^b)(CH_2)_{1-6}C(=O)N(R^b)OR^b$, $—N(R^b)(CH_2)_{1-6}C(=O)N(R^b)OR^b$, $arylC(=O)NHOH$, $—N(OH)C(=O)R^b$, $heteroarylC(=O)NHOH$, $—C_{3-6}cycloalkylN—C(=O)CH_2SH$, $—B(OR^b)_2$, $—SO_2NHR^b$, $—NHSO_2NHR^b$, $—NHSO_2C_{1-6}alkyl$, $—SO_2C_{1-6}alkyl$, $—SR^c$,

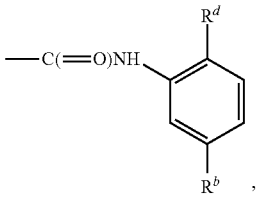

$—C(=O)R^e$, $—P(=O)(OR^f)_2$, $—NH—P(=O)(OR^f)_2$,

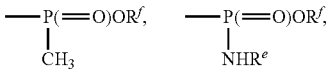

$—C(=O)(C(R^b)^2)_{1-6}SH$, $—C(=O)C(=O)NHR^b$, $—C(=O)NHN(R^b)_2$, $—C(=O)NH(CH_2)_{1-3}N(R^b)_2$,

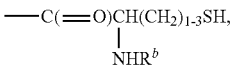

$—S—(C=O)C_{1-6}alkyl$, $C_{3-10}heterocycloalkyl$ optionally substituted with oxo (=O), thioxo (=S), or both, aryl optionally substituted with one or more of $C_{1-6}alkyl$, $—C(=O)R^d$, $—NH_2$, and —SH, heteroaryl optionally substituted with $—NH_2$, —SH, or both,

—N(H)C(=O)SH, $—NHC(=O)NHR^d$, $—NHC(=O)CH_2R^d$,

—NHC(=O)$(CH_2)_{1-6}$SH,
—NHC(=O)$CH_2$Hal,
—NHC(=S)NHR$^d$,
—NHC(=S)$CH_2$R$^d$,
—C(=S)NHR$^d$,
—C(=S)$CH_2$R$^d$,
—NHC(=S)$CH_2$R$^d$,
—NHC(=S)$CH_2$Hal, and
—(C=O)$C_{1-6}$alkyl;

R$^b$, independently, is selected from the group consisting of hydrogen, (C=O)$CH_3$, $C_{1-6}$alkyl, $CF_3$, $CH_2F$, and aryl, or two R$^b$ groups are taken together with the carbon to which they attached to form a $C_{3-8}$cycloalkyl group;

R$^c$ is selected from hydrogen or (C=O)$CH_3$;

R$^d$ is $NH_2$ or OH;

R$^e$ is selected from the group consisting of OH, N(R$^b$)$^2$, NH($OCH_3$), N($CH_3$)OH, $C_{1-6}$alkyl, $CF_3$, aryl, heteroaryl, $C_{3-8}$cycloalkyl, $NHSO_2CH_3$, $NHSO_2CF_3$, and $C_{1-6}$haloalkyl;

R$^f$ independently is hydrogen, methyl, or ethyl; and

Hal is halo, or a pharmaceutically acceptable salt, hydrate, prodrug thereof.

In another embodiment, the present invention provides a method of treating a condition or disease by administering a therapeutically effective amount of a present HDACI to an individual in need thereof. The disease or condition of interest is treatable by inhibition of HDAC, for example, a cancer, a neurodegenerative disorder, a traumatic brain injury, a neurological disease, peripheral neuropathy, an inflammation, stroke, hypertension, an autoimmune disease, allograft rejection, and malaria.

The present HDACIs contain, but are not limited to, a bidentate chelate as the zinc binding group (ZBG). Preferably, a present HDACI contains a relatively short linker group between the ZBG and the aromatic surface recognition group, e.g., contains a 0 to 5 carbon atom chain. The surface recognition group is a bicyclic, monocyclic, or acyclic moiety, such as indolyl, i.e.,

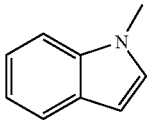

i.e., pyridinyl, i.e.,

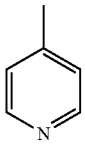

or phenyl, i.e.,

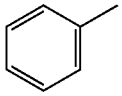

It has been found that a degree of isoform selectivity for an HDACI can be achieved by manipulating the surface recognition group in concert with the ZBG. In particular, a combination of steric and electronic properties of the surface recognition group modulates the ability of the compounds to target different isoforms via interactions with an HDAC surface. Such considerations led to the present HDACIs having a surface recognition group that exhibits selectivity in the inhibition of HDAC6.

Another embodiment of the present invention provides a method of treating a cancer comprising administering to an individual in need thereof, such as a human, a therapeutically effective amount of a present HDACI. A present HDACI can be administered as the sole anticancer therapy, or in conjunction with a therapeutically effective amount of a second anticancer agent, such as radiation and/or chemotherapy.

Another embodiment of the present invention provides a method of increasing the sensitivity of a cancer cell to the cytotoxic effects of radiotherapy and/or chemotherapy comprising contacting the cell with an effective amount of a present HDACI. In certain embodiments, the cell is an in vivo cell.

In another embodiment, the present invention provides a method of treating a neurological disease comprising administering to an individual in need thereof, such as a human, a therapeutically effective amount of a present HDACI. The present invention also relates to a method of treating neurodegenerative disorders, peripheral neuropathies, and traumatic brain injuries comprising administering a therapeutically effective amount of a present HDACI to an individual in need thereof. In each embodiment, a present HDACI can be the sole therapeutic agent or can be administered with additional therapeutic agents known to treat the disease or condition of interest.

The present invention also provides a method of treating malaria and other parasitic infections comprising administering a therapeutically effective amount of a present HDACI to an individual in need thereof. In certain embodiments, the individual is a human. In certain embodiments, said method further comprises optionally coadministering a second antimalarial compound (e.g., chloroquine).

In yet another embodiment, the present invention provides a method of inducing immunosuppression in an individual comprising administration of a therapeutically effective amount of a present HDACI to an individual in need thereof, for example, an individual receiving a transplant. This method further comprises optionally coadministering a second immunosuppressant (e.g., cyclosporin) or therapeutic agent.

In still another embodiment, the present invention provides a method of treating inflammatory diseases and conditions, e.g., arthritis and rheumatic diseases, comprising administration of a therapeutically effective amount of a present HDACI to an individual in need thereof. The method further contemplates optional coadministration of a second anti-inflammatory drug or therapeutic agent.

In another embodiment, the present invention also provides a pharmaceutical composition comprising a present HDACI and a pharmaceutically acceptable excipient.

Another embodiment of the present invention is to utilize a present HDACI and an optional second therapeutically active agent in a method of treating an individual for a disease or condition wherein inhibition of HDAC provides a benefit.

In a further embodiment, the invention provides for use of a composition comprising a present HDACI and an optional second therapeutic agent for the manufacture of a medicament for treating a disease or condition of interest, e.g., a cancer, neurodegeneration, or autoimmunity.

Still another embodiment of the present invention is to provide a kit for human pharmaceutical use comprising (a) a container, (b1) a packaged composition comprising a present HDACI, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

A present HDACI and the second therapeutic agent can be administered together as a single-unit dose or separately as multi-unit doses, wherein a present HDACI is administered before the second therapeutic agent, or vice versa. It is envisioned that one or more dose of a present HDACI and/or one or more dose of a second therapeutic agent can be administered.

In one embodiment, a present HDACI and a second therapeutic agent are administered simultaneously. In related embodiments, a present HDACI and second therapeutic agent are administered from a single composition or from separate compositions. Ina further embodiment, a present HDACI and a second therapeutic agent are administered sequentially. A present HDACI can be administered in an amount of about 0.005 to about 500 milligrams per dose, about 0.05 to about 250 milligrams per dose, or about 0.5 to about 100 milligrams per dose.

Compounds of the invention inhibit HDAC and are useful research tools for in vitro study of histone deacetylases and their role in biological processes.

These and other novel aspects of the present invention will become apparent from the following detailed description of the preferred embodiments.

DETAILED DESCRIPTION OF THE PREFERRED EMBODIMENTS

Figure 1:
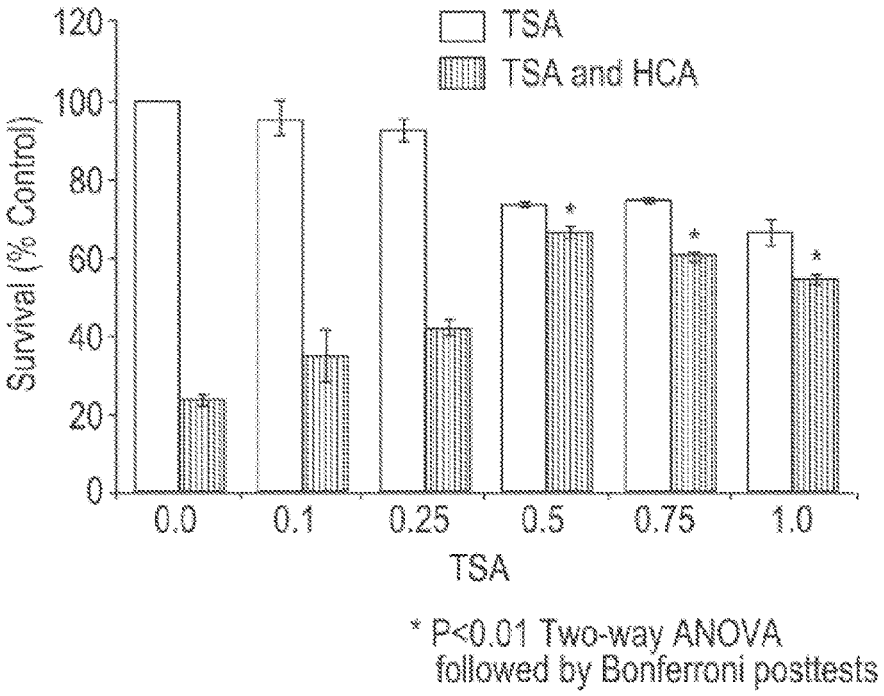
FIG. 1 (PRIOR ART)
FIG. 1 contains bar graphs of concentrations of TSA vs. survival (% control) for the HCA oxidative stress assay.

The present invention is directed to novel HDACIs and their use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria. The present HDACIs also increase the sensitivity of a cancer cell to the cytotoxic effects of radiotherapy and/or chemotherapy. In some embodiments, the present HDACIs selectively inhibit HDAC6 over other HDAC isozymes.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "a disease or condition wherein inhibition of HDAC provides a benefit" pertains to a condition in which HDAC and/or the action of HDAC is important or necessary, e.g., for the onset, progress, expression of that disease or condition, or a disease or a condition which is known to be treated by an HDAC inhibitor (such as, e.g., TSA, pivalolyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hematopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC for any particular cell type, for example, by assays which conveniently can be used to assess the activity of particular compounds.

The term "second therapeutic agent" refers to a therapeutic agent different from a present HDACI and that is known to treat the disease or condition of interest. For example, when a cancer is the disease or condition of interest, the second therapeutic agent can be a known chemotherapeutic drug, like taxol, or radiation, for example.

The term "HDAC" refers to a family of enzymes that remove acetyl groups from a protein, for example, the ϵ-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

HDAC inhibitors (HDACIs) typically contain three structural elements which are analogous to the structure of acetyllysine. These three structural elements are a zinc binding group (M), which is responsible for chelation of zinc in the active site, a linker region (L), which binds to the hydrophobic channel that connects the active site to the outer enzyme surface, and a capping group (Cap), which interacts with residues at the outer enzyme surface.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling in the target cells; and/or relieve, to some extent, one or more of the symptoms associated with the cancer. To extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present HDACI can be administered at the same time or sequentially in any order at different points in time as a second therapeutic agent. A present HDACI and the second therapeutic agent can be administered separately, in any appropriate form and by any suitable route. When a present HDACI and the second therapeutic agent are not administered concurrently, it is understood that they can be administered in any order to a subject in need thereof. For example, a present HDACI can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present HDACI and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

In particular, the present invention is directed to HDACIs, compositions comprising a present HDACI, and therapeutic uses of the HDACIs of the following structural formula:

Cap-L-M wherein Cap is selected from the group consisting of (a)

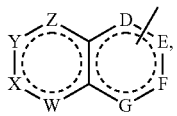

wherein ring

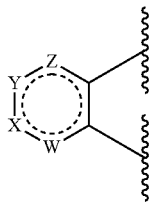

is an aliphatic or aromatic five or six membered ring,

W, X, Y, and Z independently are selected from the group consisting of null, $C(R^1)_2$, O, S, and $NR^1$, ring

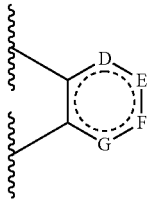

is an aliphatic or aromatic five or six membered ring,

D, E, F, and G independently are selected from the group consisting of null, $C(R^1)_2$, O, S, and $NR^1$, $R^1$, independently, is selected from the group consisting of null, hydrogen, $C_{1-6}$alkyl, $C_{1-6}$heteroalkyl, $C_{2-6}$alkenyl, $C_{1-6}$perfluoroalkyl, $C_{1-6}$perfluoroalkoxy, aryl, heteroaryl, $C_{3-10}$cycloalkyl, $C_{3-10}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

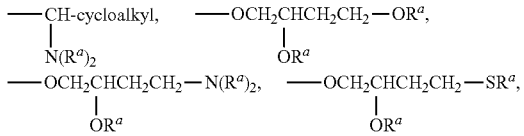

$OR^a$, halo, $N(R^a)_2$, $SR^a$, $SOR^a$, $SO_2R^a$, CN, $C(=O)R^a$, $CF_3$, $OCF_3$, $NO_2$, $OC(=O)R^a$, $SO_2N(R^a)_2$, $OSO_2CF_3$, $C(=O)OR^a$, $C(=O)N(R^a)_2$, $C_{1-6}$alkyleneN$(R^a)_2$, $C_{1-6}$alkyleneC$(=O)R^a$, $C_{1-6}$alkyleneOR$^a$, $C_{1-6}$alkyleneSR$^a$, $C_{1-6}$alkyleneNR$^a$SO$_2$R$^a$, $C_{1-6}$alkyleneSOR$^a$, $C_{1-6}$alkyleneCN, $C_{1-6}$heteroalkyleneCN, $C_{1-6}$alkyleneC$(=O)OR^a$, $C_{1-6}$alkyleneOC$(=O)N(R^a)_2$, $C_{1-6}$alkyleneNR$^a$C$(=O)OR^a$, $C_{1-6}$alkyleneNR$^a$C$(=O)R^a$, $C_{1-6}$alkylene C$(=O)N(R^a)_2$, $C_{1-6}$alkyleneOC$_{1-6}$alkyleneC$(=O)OR^a$, $C(=O)NR^aSO_2R^a$, $C(=O)C_{1-6}$alkylenearyl, $C(=O)NR^aC_{1-6}$alkyleneOR$^a$, OC$_{1-6}$alkyleneC$(=O)OR^a$, OC$_{1-6}$alkyleneN$(R^a)_2$, OC$_{1-6}$alkyleneOR$^a$, OC$_{1-6}$alkyleneNR$^a$C$(=O)OR^a$, NR$^a$C$_{1-6}$alkyleneN$(R^a)_2$, NR$^a$C$(=O)R^a$, NR$^a$C$(=O)N(R^a)_2$, N$(SO_2C_{1-6}$alkyl$)_2$, and NR$^a$($SO_2C_{1-6}$alkyl), and $R^a$, independently, is selected from the group consisting of hydrogen, $C_{1-6}$alkyl, $C_{1-6}$heteroalkyl, $C_{1-6}$alkyleneNH$_2$, $C_{1-6}$alkyleneNH($C_{1-6}$alkyl), $C_{1-6}$alkyleneN($C_{1-6}$alkyl)$_2$, $C_{1-6}$alkyleneNH($C_{1-6}$alkyl)$_2$, $C_{1-6}$alkyleneNHC$(=O)(C_{1-6}$alkyl), $C_{1-6}$alkyleneC$(=O)NH_2$, $C_{1-6}$alkyleneOH, $C_{1-6}$alkyleneCN, $C_{1-6}$heteroalkyleneCN, $C_{1-6}$alkyleneOC$_{1-6}$ alkyl, $C_{1-6}$alkyleneSH, $C_{1-6}$alkyleneSC$_{1-6}$alkyl, $C_{1-6}$alkyleneNH($SO_2C_{1-6}$alkyl), aryl, heteroaryl, $C_{3-8}$cycloalkyl, and $C_{3-10}$heterocycloalkyl, (b)

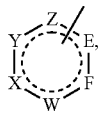

wherein ring

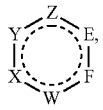

is an aliphatic or aromatic five or six membered ring,

E, F, W, X, Y, Z, $R^1$, and $R^a$ are as defined above, and (c)

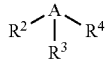

wherein A is C, N, O, S, B, or P, and L is attached to A, $R^2$, $R^3$ and $R^4$ independently are selected from the group consisting of null, hydrogen, $C_{1-6}$alkyl, $C_{1-6}$heteroalkyl, $C_{2-6}$alkenyl, $C_{1-6}$perfluoroalkyl, $C_{1-6}$perfluoroalkoxy, aryl, heteroaryl, $C_{3-10}$cycloalkyl, $C_{3-8}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

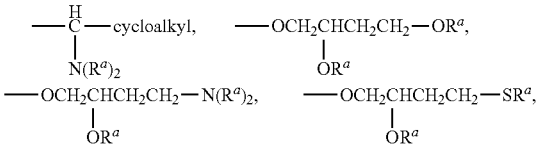

$OR^a$, halo, $N(R^a)_2$, $SR^a$, $SOR^a$, $SO_2R^a$, CN, $C(=O)R^a$, $OC(=O)R^a$, $C(=O)OR^a$, $C_{1-6}$alkylerleN$(R^a)_2$, $C_{1-6}$alkyleneOR$^a$, $C_{1-6}$alkyleneSR$^a$, $C_{1-6}$alkyleneC$(=O)OR^a$, $C(=O)N(R^a)_2$, $C(=O)NR^aC_{1-6}$alkyleneOR$^a$, OC$_{1-6}$alkyleneC$(=O)OR^a$, OC$_{1-6}$alkyleneN$(R^a)_2$, OC$_{1-6}$alkyleneOR$^a$, OC$_{1-6}$alkyleneNR$^a$C$(=O)OR^a$, NR$^a$C$_{1-6}$alkyleneN$(R^a)_2$, NR$^a$C$(=O)R^a$, NR$^a$C$(=O)N(R^a)_2$, N$(SO_2C_{1-6}$alkyl$)_2$, NR$^a$($SO_2C_{1-6}$alkyl), nitro, and $SO_2N(R^a)^2$, and $R^a$ is defined above;

L is selected from the group consisting of null, $C_{1-8}$alkylene, $R^a$ substituted $C_{1-8}$alkylene, NR$^a$, C(=O), aryl, C(=O)aryl, C(=O)C$_{1-6}$alkylene, $C_{1-8}$alkyleneNR$^a$, $C_{1-6}$alkylenearyleneC$_{1-6}$alkylene, $C_{2-6}$alkenylene, $C_{4-8}$alkdienylene, $C_{1-6}$alkylenearylene, $C_{1-6}$alkyleneheteroarylene, $R^a$ substituted $C_{1-6}$alkyleneheteroarylene, and $C_{2-6}$alkenylenearyleneC$_{1-6}$alkylene, and $R^a$ is defined above;

M is selected from the group consisting of —C(=O)N$(R^b)$OH,

—O$(CH_2)_{1-6}$C(=O)N$(R^b)OR^b$,

—N$(R^b)(CH_2)_{1-6}$C(=O)N$(R^b)OR^b$,

—N$(R^b)(CH_2)_{1-6}$C(=O)N$(R^b)OR^b$, arylC(=O)NHOH,

—N(OH)C(=O)R$^b$, heteroarylC(=O)NHOH,

—$C_{3-6}$cycloalkylN—C(=O)CH$_2$SH,

—B$(OR^b)_2$,

—SO$_2$NHR$^b$,

—NHSO$_2$NHR$^b$,

—NHSO$_2$C$_{1-6}$alkyl,

—SO$_2$C$_{1-6}$alkyl,

—SR$^c$,

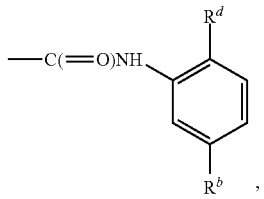

—C(=O)R$_e$,

—P(=O)(OR$^f$)$_2$,

—NH—P(=O)(OR$^f$)$_2$,

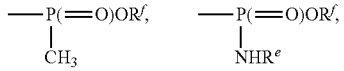

—C(=O)(C(R$^b$)$^2$)$_{1-6}$SH,

—C(=O)C(=O)NHR$^b$,

—C(=O)NHN$(R^b)_2$,

—C(=O)NH$(CH_2)_{1-3}$N$(R^b)_2$,

—C(═O)CH(NHR$^b$)(CH$_2$)$_{1-3}$SH,

—S—(C═O)C$_{1-6}$alkyl,

C$_{3-10}$heterocycloalkyl optionally substituted with oxo (═O), thioxo (═S), or both, aryl optionally substituted with one or more of C$_{1-6}$alkyl, —C(═O)R$^d$, —NH$_2$, and —SH, heteroaryl optionally substituted with —NH$_2$, —SH, or both,

—N(H)C(═O)SH,

—NHC(═O)NHR$^d$,

—NHC(═O)CH$_2$R$^d$,

—NHC(═O)(CH$_2$)$_{1-6}$SH,

—NHC(═O)CH$_2$Hal,

—NHC(═S)NHR$^d$,

—NHC(═S)CH$_2$R$^d$,

—C(═S)NHR$^d$,

—C(═S)CH$_2$R$^d$,

—NHC(═S)CH$_2$R$^d$,

—NHC(═S)CH$_2$Hal, and

—(C═O)C$_{1-6}$alkyl;

R$^b$, independently, is selected from the group consisting of hydrogen, (C═O)CH$_3$, C$_{1-6}$alkyl, CF$_3$, CH$_2$F, and aryl, or two R$^b$ groups are taken together with the carbon to which they attached to form a C$_{3-8}$cycloalkyl group;

R$^c$ is selected from hydrogen or (C═O)CH$_3$;

R$^d$ is NH$_2$ or OH;

R$^e$ is selected from the group consisting of OH, N(R$^b$)$^2$, NH(OCH$_3$), N(CH$_3$)OH, C$_{1-6}$alkyl, CF$_3$, aryl, heteroaryl, C$_{3-8}$cycloalkyl, NHSO$_2$CH$_3$, NHSO$_2$CF$_3$, and C$_{1-6}$haloalkyl;

R$^f$ independently is hydrogen, methyl, or ethyl; and

Hal is halo, or a pharmaceutically acceptable salt, hydrate, or prodrug thereof.

Compounds of the present invention inhibit HDAC and are useful in the treatment of a variety of diseases and conditions. In particular, the present HDACIs are used in methods of treating a disease or condition wherein inhibition of HDAC provides a benefit, for example, cancers, neurological diseases, neurodegenerative conditions, peripheral neuropathies, autoimmune diseases, inflammatory diseases and conditions, stroke, hypertension, traumatic brain injury, autism, and malaria. The methods comprise administering a therapeutically effective amount of a present HDACI to an individual in need thereof.

The present methods also encompass administering a second therapeutic agent to the individual in addition to a present HDACI. The second therapeutic agent is selected from agents, such as drugs and adjuvants, known as useful in treating the disease or condition afflicting the individual, e.g., a chemotherapeutic agent and/or radiation known as useful in treating a particular cancer.

As used herein, the term "alkyl" refers to straight chained and branched saturated hydrocarbon groups, nonlimiting examples of which include methyl, ethyl, and straight chain and branched propyl, butyl, pentyl, hexyl, heptyl, and octyl groups containing the indicated number of carbon atoms. The term C$_n$ means the alkyl group has "n" carbon atoms.

The term "alkylene" refers to a bidentate moiety obtained by removing two hydrogen atoms from an alkane. An "alkylene" is positioned between two other chemical groups and serves to connect them. An example of an alkylene group is —(CH$_2$)$_n$—. An alkyl, e.g., methyl, or alkylene, e.g., —CH$_2$CH$_2$—, group can be substituted, independently, with one or more of halo, trifluoromethyl, trifluoromethoxy, hydroxy, alkoxy, nitro, cyano, alkylamino, and amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkdienylene" is defined identically as "alkenylene" except the group contains two carbon-carbon double bonds, either conjugated or non-conjugated.

The term "heteroalkyl" refers to an alkyl group having one or more, and typically one to three, heteroatoms in the carbon chain of the alkyl group. The heteroatoms, independently, are selected from O, S, and NR, wherein R is hydrogen, alkyl, cycloalkyl, heterocycloalkyl, aryl, and heteroaryl. A term such as "C$_{1-6}$heteroalkyl" means that the group contains 1 to 6 carbon atoms in addition to the heteroatoms.

The term "perfluoroalkyl" is defined as an alkyl group wherein all hydrogen atoms are replaced by fluorine atoms.

As used herein, the term "halo" and "Hal" are defined as fluoro, chloro, bromo, and iodo.

The term "hydroxy" is defined as —OH.

The term "alkoxy" is defined as —OR, wherein R is alkyl. The term "perfluoroalkoxy" is defined as an alkoxy group wherein all hydrogen atoms are replaced by fluorine atoms.

The term "amino" is defined as —NR$_2$, wherein each R group, independently, is hydrogen, alkyl, cycloalkyl, heterocycloalkyl, C$_{1-3}$alkylenearyl, heteroaryl, or aryl, or both R groups are taken together with the N to which they are attached to form a 4 to 8 membered ring.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

The term "Ac" is defined as —C(═O)CH$_3$.

The term "tBu" is defined as tertiary butyl, i.e. —C(CH$_3$)$_3$.

The term "Boc" is defined as tert-butoxycarbonyl.

As used herein, compounds such as

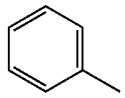

is an abbreviation for

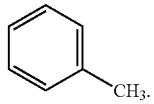

In addition, compounds such as

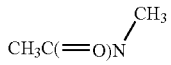

is an abbreviation for

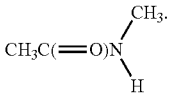

As used herein, groups such as $C_{1-3}$alkylphenyl means a $C_{1-3}$alkyl group bonded to a phenyl ring, for example,

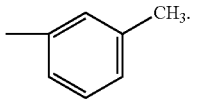

Groups such as $C_{1-3}$alkylenephenyl means a phenyl group bonded to a $C_{1-3}$alkylene group, for example,

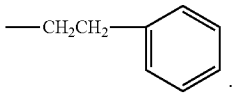

As used herein, the term "aryl" refers to a monocyclic aromatic group, e.g., phenyl. Unless otherwise indicated, an aryl group can be unsubstituted or substituted with one or more, and in particular one to five, groups independently selected from, for example, halo, alkyl, alkenyl, —$OCF_3$, —$NO_2$, —CN, —NC, —OH, alkoxy, amino, alkylamino, —$CO_2H$, —$CO_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Exemplary aryl groups include, but are not limited to, phenyl, chlorophenyl, methylphenyl, methoxyphenyl, trifluoromethylphenyl, nitrophenyl, 2,4-methoxychlorophenyl, and the like.

The term "arylene" refers to a bidentate aryl group that bonds to two other groups and serves to connect these groups, e.g.,

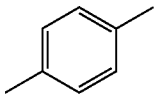

The term "$C_{1-4}$alkylenearyleneC$_{1-4}$alkylene" means

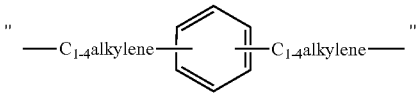

and serves to connect two other groups.

The term "$C_{1-6}$alkylenearylene" means

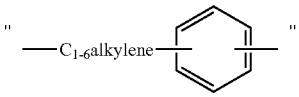

and serves to connect two other groups.

The term "$C_{2-6}$alkenylenearyleneC$_{1-4}$alkylene" means

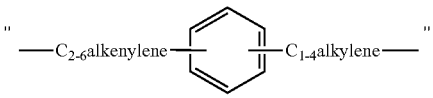

and serves to connect two other groups.

As used herein, the term "heteroaryl" refers to a monocyclic ring system containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, alkylamino, —$CO_2H$, —$CO_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Examples of heteroaryl groups include, but are not limited to, thienyl, furyl, oxazolyl, thiophenyl, triazolyl, isothiazolyl, isoxazolyl, imidazolyl, pyrimidinyl, thiazolyl, thiadiazolyl, pyridinyl, pyridazinyl, pyrazolyl, pyrazinyl, tetrazolyl, oxazolyl, pyrrolyl, and triazinyl.

As used herein, the term "$C_{3-8}$cycloalkyl" means a monocyclic aliphatic ring containing three to eight carbon atoms, either saturated or unsaturated.

As used herein, the term "heterocycloalkyl" means a monocyclic or a bicyclic aliphatic ring containing 3 to 10 total atoms, either saturated or unsaturated, of which one to five of the atoms are independently selected from nitrogen, oxygen, and sulfur and the remaining atoms are carbon.

In accordance with the present invention, bicyclic ring system

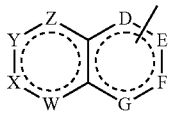

can be, for example, a residue of:

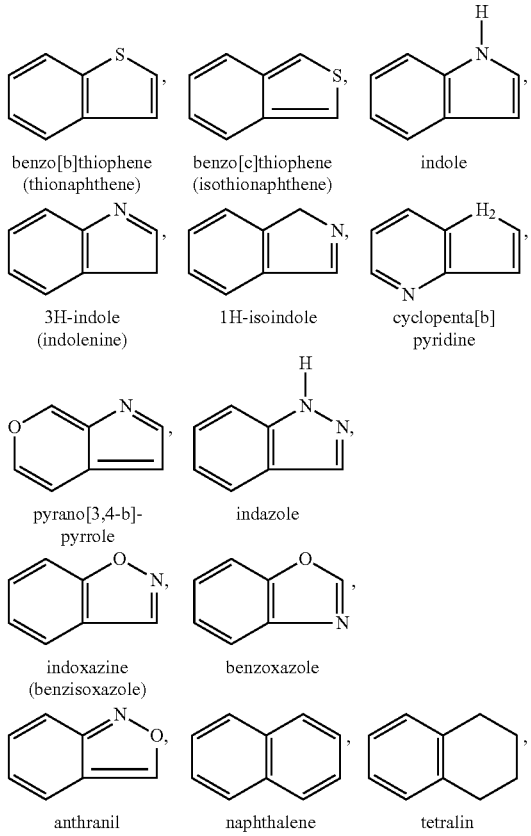

-continued

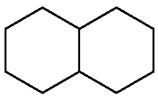

decalin (bicyclo[4,4,0]-decane)

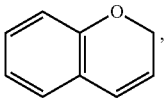

2H-1-benzopyran (2H-chromene)

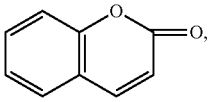

coumarin (1,2-benzopyrone)

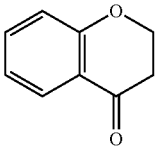

coumarin-4-one (1,4-benzopyrone)

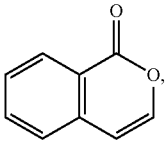

isochromen-1-one (isocoumarin)

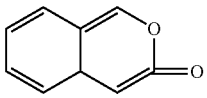

isochromen-3-one

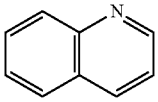

quinoline

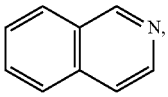

isoquinoline

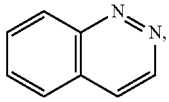

cinnoline

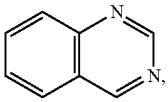

quinazoline

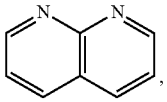

naphthyridine

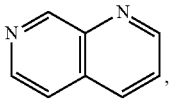

pyrido[3,4-b]-pyridine

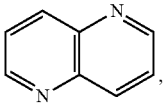

pyrido[3,2-b]-pyridine

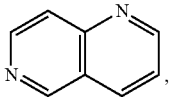

pyrido[4,3-b]-pyridine

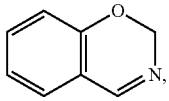

2H-1,3-benzoxazine

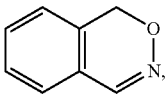

1H-2,3-benzoxazine

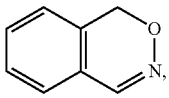

4H-3,1-benzoxazine

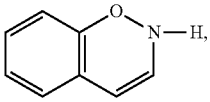

2H-1,2-benzoxazine

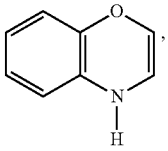

4H-1,4-benzoxazine

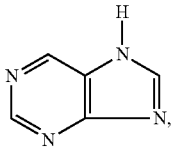

purine

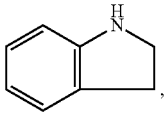

indoline

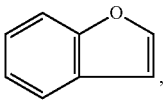

benzo(b)furan

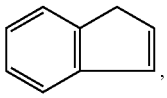

indene

-continued

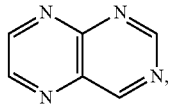

pteridine

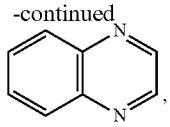

quinoxaline

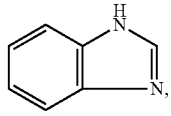

benzimidazole

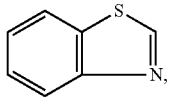

benzthiazole and

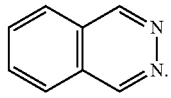

phthalzine

The linker L can be attached to any atom D, E, F, G, W, X, Y, or Z, and in some preferred embodiments the linker L is attached to a nitrogen atom of the bicyclic ring system.

In accordance with the present invention, ring

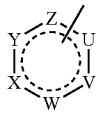

is a five- or six-membered, aliphatic or aromatic ring. For example, the ring can be

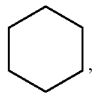

cyclohexyl

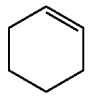

cyclohexenyl

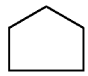

cyclopentyl

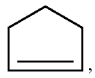

cyclopentenyl

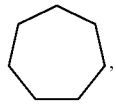

cycloheptyl

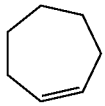

cycloheptenyl

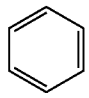

phenyl

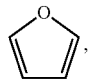

furanyl

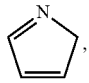

2H-pyrrolyl

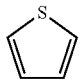

thienyl

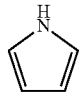

pyrrolyl

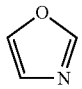

oxazolyl

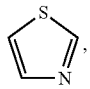

thiazolyl

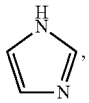

imidazolyl

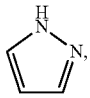

pyrazolyl

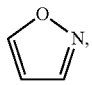

isoxazolyl

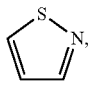

isothiazolyl

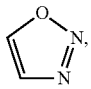

1,2,3-oxadiazolyl

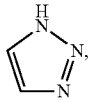

1,2,3-triazolyl

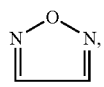

1,2,5-oxadiazolyl

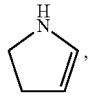

2-pyrrolinyl

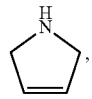

3-pyrrolinyl

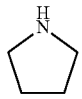

pyrrolidinyl

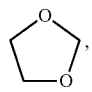

1,3-dioxolanyl

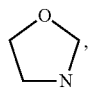

oxazolyl

-continued

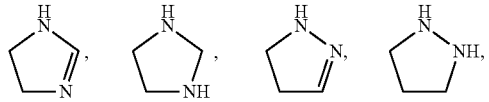

2-imidazolinyl, imidazolidinyl, 2-pyrazolinyl, pyrazolidinyl

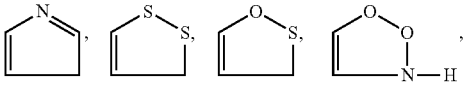

3H-pyrrolyl, 1,3-dithiolyl, 3H-1,2-oxathiolyl, 3H-1,2,3-dioxazolyl

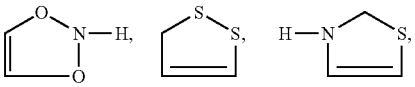

1,3,2-dioxazolyl, 1,2-diothiolyl, 5H-1,2,5-oxathiazolyl

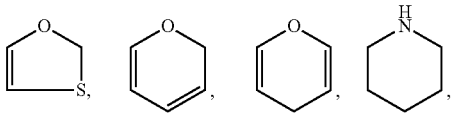

1,3-oxathiolyl, 2H-pyranyl, 4H-pyranyl, piperidinyl

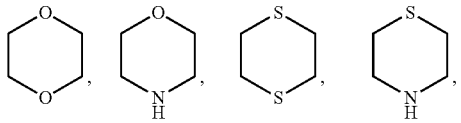

1,4-dioxanyl, morpholinyl, 1,4-dithianyl, thiomorpholinyl

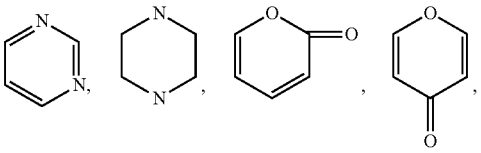

pyrimidinyl, piperazinyl, 2-pyronyl, 4-pyronyl

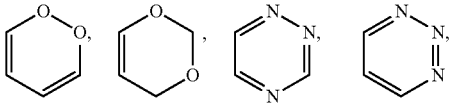

1,2-dioxinyl, 1,3-dioxinyl, 1,2,4-triazinyl, 1,2,3-triazinyl

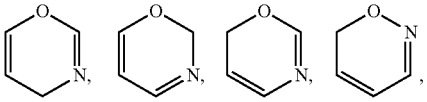

4H-1,3-oxazinyl, 2H-1,3-oxazinyl, 6H-1,3-oxazinyl, 6H-1,2-oxazinyl

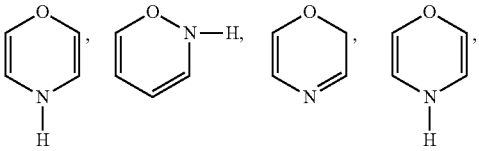

4H-1,4-oxazinyl, 2H-1,2-oxazinyl, 1,4-oxazinyl, p-isoxazinyl

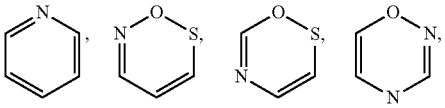

pyridinyl, 1,2,6-oxathiazinyl, 1,2,5-oxathiazinyl, 1,4,2-oxadiazinyl

-continued

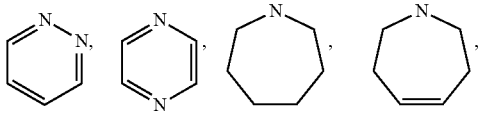

pyridazinyl, pyrazinyl, azacycloheptyl, azacycloheptenyl

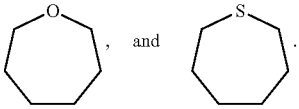

oxacycloheptyl and thiacycloheptyl

The linker L can be attached to any atom U, V, W, X, Y, or Z, and preferably is attached to a nitrogen or carbon atom of the ring.

In some embodiments, a bicyclic Cap group has a structure:

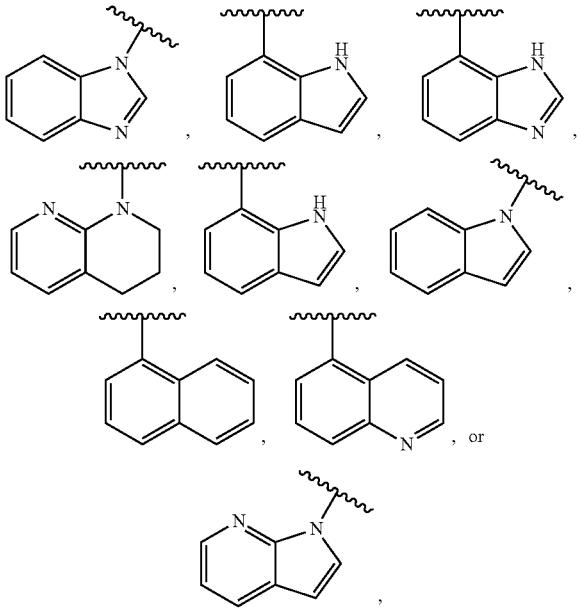

either unsubstituted or substituted with one or more $R^1$.

In some embodiments, a monocyclic Cap group has a structure:

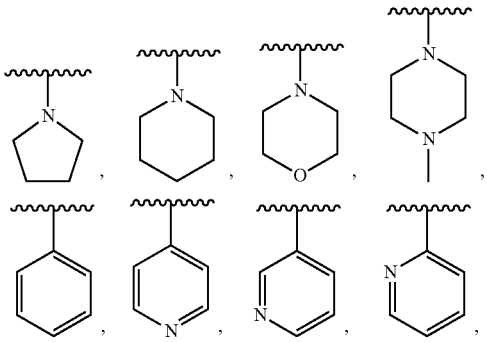

-continued

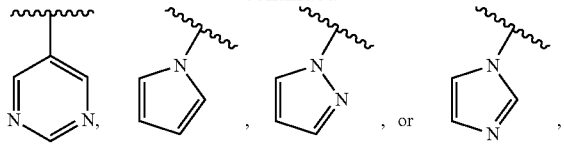

either unsubstituted or substituted with one or more $R^1$ group.

In some embodiments, an alicyclic Cap group has a structure wherein A is N, e.g.,

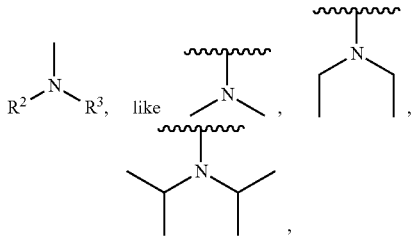

In some embodiments, $R^1$ substituents on the Cap group, if present at all, preferably are null, hydrogen, $OR^a$, halo, $C_{1-6}$alkyl, aryl, heterocycloalkyl, —$(CH_2)_{1-4}$heterocycloalkyl, —$(CH_2)_{1-4}N(R^a)_2$,

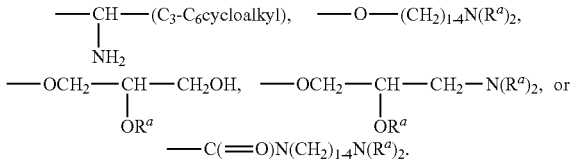

In some embodiments, $R^a$ is hydrogen, $C_{1-6}$alkyl, $C_{1-6}$heteroalkyl, and heteroaryl.

In other preferred embodiments, L is null, —$(CH_2)_{1-6}$—,

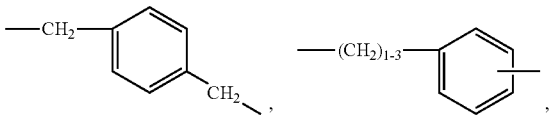

optionally substituted with halo, $CF_3$, or CN,

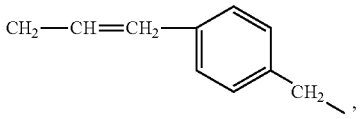

—$CH_2$—CH═CH—CH═CH—,

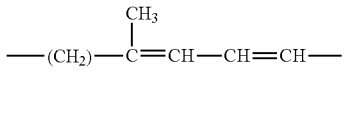

—$(CH_2)_2$—CH═CH—CH═$CH_2$—, —$(CH_2)_{0-6}$—NH—,

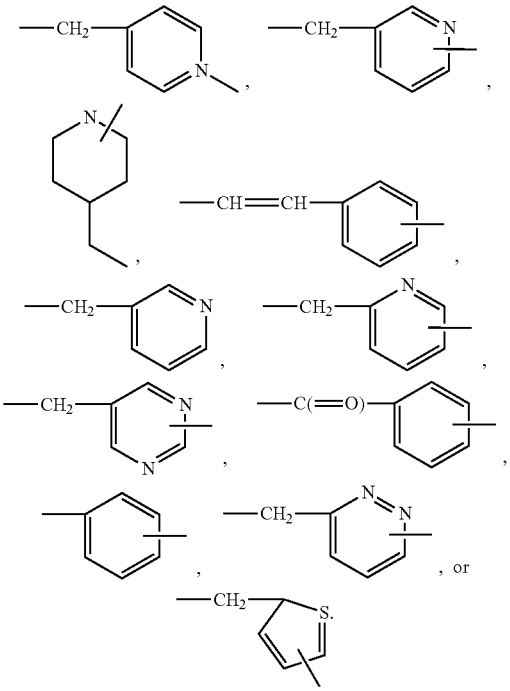

In still other preferred embodiments, M is

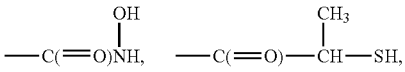

—C(═O)$CH_2$SH, —$CH_2$SH,

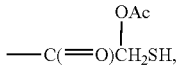

—SC(═O)tBu, —SC(═O)$CF_3$, —S$(CH_2)_{1-3}$C(═O)$CF_3$, —$CH_2$SAc,

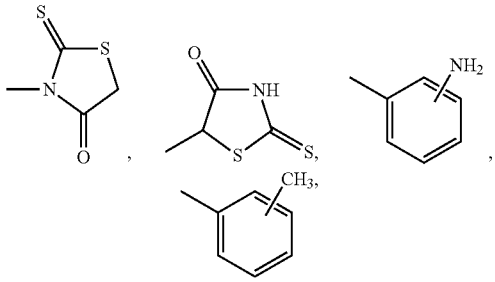

—NH—C(═O)$CH_2$SH,

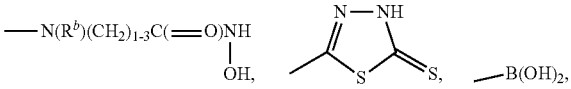

-continued

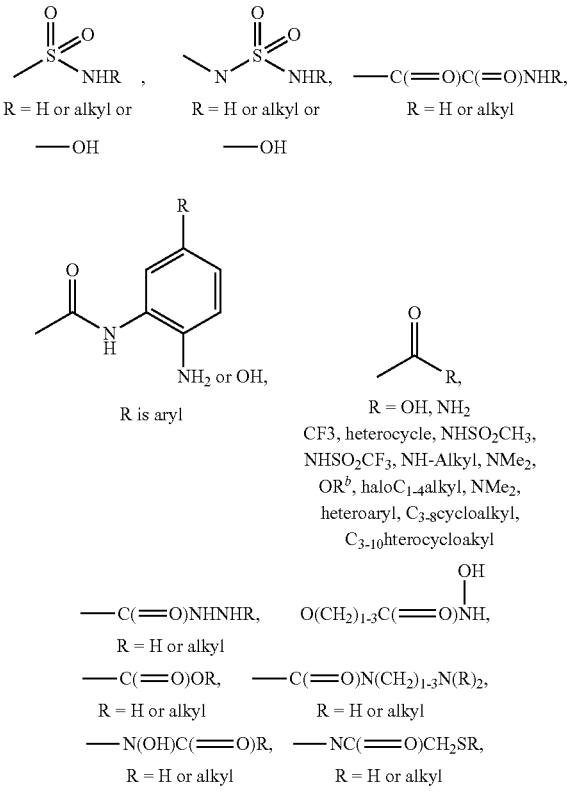

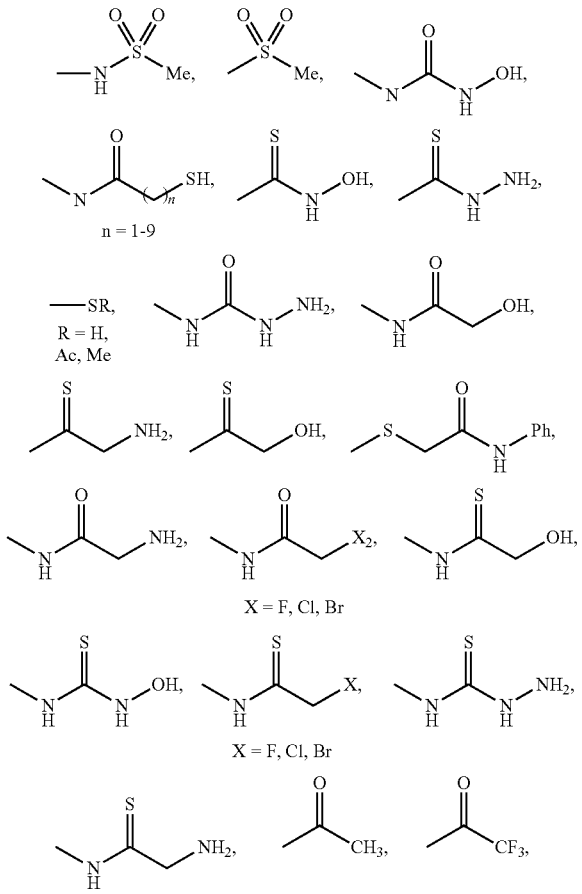

-continued

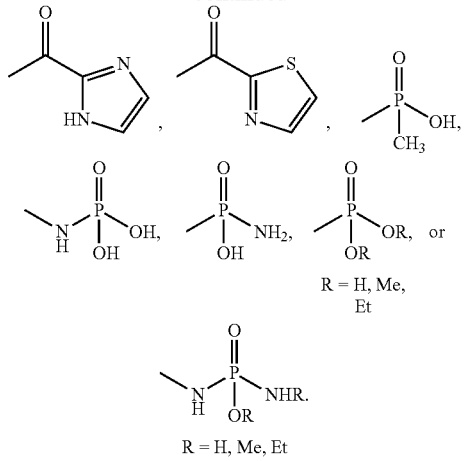

Additionally, salts, prodrugs, hydrates, isotopically labeled, fluorescently labeled and any other therapeutically or diagnostically relevant derivations of the present HDACIs also are included in the present invention and can be used in the methods disclosed herein. The present invention further includes all possible stereoisomers and geometric isomers of the present compounds. The present invention includes both racemic compounds and optically active isomers. When a present HDACI is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of a present compound is possible, the present invention is intended to include all tautomeric forms of the compounds.

Prodrugs of the present compounds also are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)). Specific prodrugs of HDACIs are discussed in WO 2008/055068, incorporated in its entirety herein by reference.

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the invention can exist as salts. Pharmaceutically acceptable salts of the present HDACIs often are preferred in the methods of the invention. As used herein, the term "pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include the present compounds as well as pharmaceutically acceptable salts, hydrates, or prodrugs thereof.

The present compounds also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., Clin. Cancer Res. (2001) 7:3229).

Specific compounds of the present invention include, but are not limited to,

12

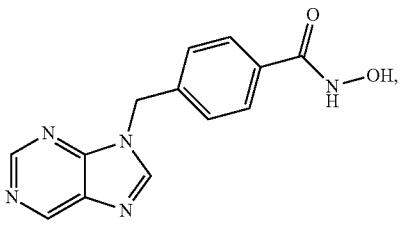

-continued

14

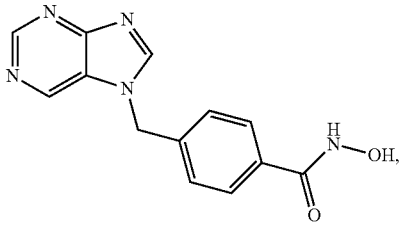

23

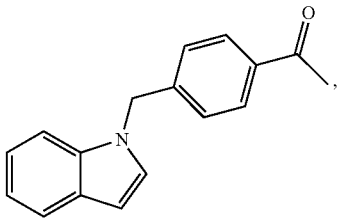

22

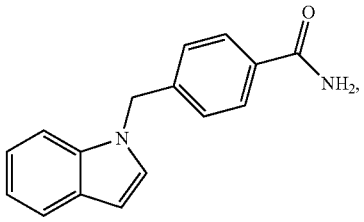

8

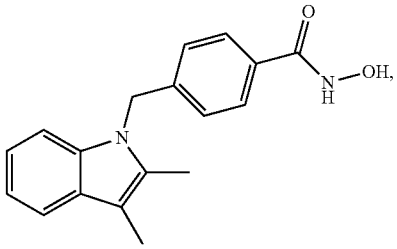

38

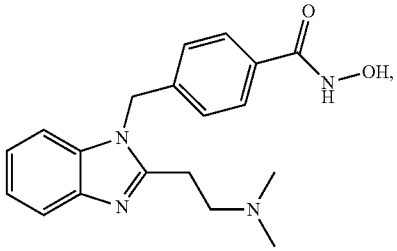

41

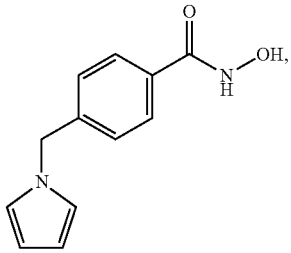

-continued
43
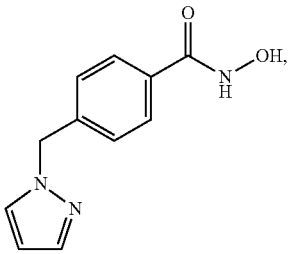
45
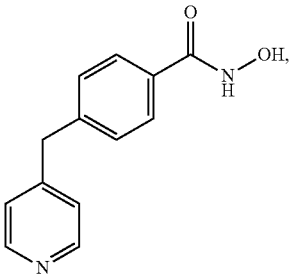
47
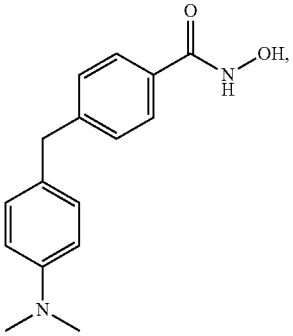
49
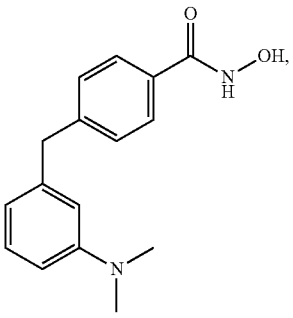
51
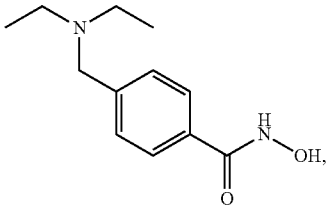
-continued
53
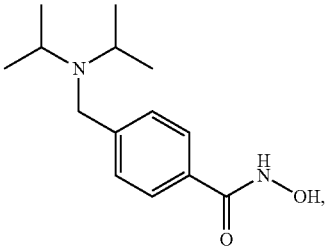
55
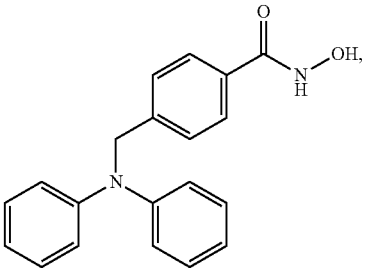
57
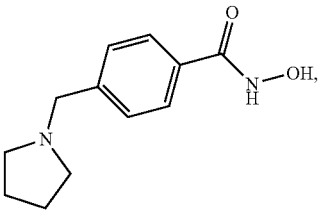
59
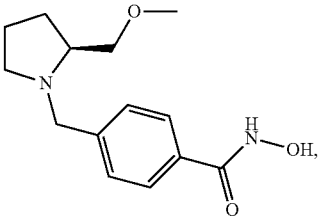
21
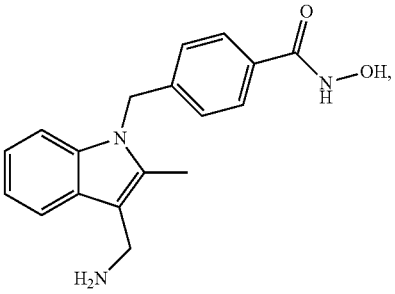

-continued

17

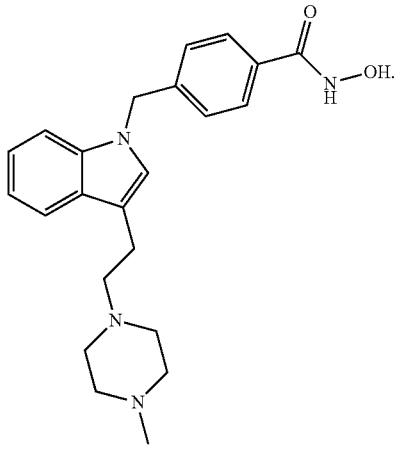

Synthetic Methods

The following synthetic schemes are representative of the reactions used to synthesize the present HDACIs. Modifications and alternate schemes to prepare HDACIs of the invention are readily within the capabilities of persons skilled in the art.

In the synthetic methods, the examples, and throughout the specification, the abbreviations have the following meanings:

| | |
|---|---|
| DMF | dimethylformamide |
| min | minutes |
| TLC | thin layer chromatography |
| $CH_2Cl_2$ | methylene chloride |
| MeOH | methanol |
| $Na_2SO_4$ | sodium sulfate |
| AcOH | acetic acid |
| MS | mass spectrometry |
| $Na_2CO_3$ | sodium carbonate |
| HPLC | high performance liquid chromatography |
| H or hrs | hours |
| $NaHCO_3$ | sodium bicarbonate |
| HCl | hydrochloric acid |
| g | gram |
| mol | mole |
| mmol | millimole |
| mL | milliliter |
| $H_2SO_4$ | sulfuric acid |
| NaH | sodium hydride |
| TMS | tetramethylsilane |
| TFA | trifluoroacetic acid |
| KOH | potassium hydroxide |
| $NH_4Cl$ | ammonium chloride |
| $NH_2OH$•HCl | hydroxylamine hydrochloride |
| NaOMe | sodium methoxide |
| $CD_3OD$ | deuterated methanol |
| M | molar |
| KOtBu | potassium tert-butoxide |
| DMSO | dimethyl sulfoxide |
| KOH | potassium hydroxide |
| $NaCNBH_3$ | sodium cyanoborohydroxide |
| N | normal |
| KI | potassium iodide |
| $SOCl_2$ | thionyl chloride |
| $CD_3CN$ | deuterated acetonitrile |
| RT | room temperature |
| DME | dimethyl ether |
| $ZnCl_2$ | zinc chloride |
| CuI | copper iodide |
| NMR | nuclear magnetic resonance spectrometry |
| EtOAc | ethyl acetate |

-continued

| | |
|---|---|
| THF | tetrahydrofuran |
| NaOH | sodium hydroxide |
| $PdCl_2(PPh)_3$ | dichloro-triphenylphosphino-palladium (II) |
| $Et_3N$ | triethylamine |
| $CDCl_3$ | deuterated chloroform |
| Hz | Hertz |

It should be understood that protecting groups can be utilized in accordance with general principles of synthetic organic chemistry to provide compounds of the present invention. Protecting group-forming reagents are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of the present invention not specifically exemplified herein can be prepared by persons skilled in the art.

Synthetic Methods and Procedures

Procedures

General Information for Synthetic Procedures: $^1$H NMR and $^{13}$C NMR spectra were obtained using a Bruker spectrometer with TMS as an internal standard. The following standard abbreviations indicating multiplicity were used: s=singlet, d=doublet, t=triplet, q=quartet, quint=quintet, m=multiplet, dd=double doublet, dt=double triplet, and br=broad. LRMS experiments were carried out using an Agilent 1100 series LC/MSD instrument with MeCN and $H_2O$ spiked with 0.1% formic acid as the mobile phase. HRMS experiments were carried out using a Shimadzu IT-TOF instrument with MeCN and $H_2O$ spiked with 0.1% formic acid as the mobile phase. Reaction progress was monitored by TLC using precoated silica gel plates (Merck silica gel 60 F254, 250 μm thickness). Automated column chromatography was performed using the CombiFlash Rf apparatus available from Teledyne ISCO and prepacked cartridges (25 or 50 g) loaded with Merck silica gel (40-60 mesh) along with the following conditions: Method 1: 100% hexane, 5 min; 0-50% EtOAc/hexane, 25 min; 50% EtOAc/hexane, 5 min. Method 2: 100% DCM, 5 min; 0-10% MeOH/DCM, 20 min, 10% MeOH/DCM, 5 min. Flow rate=30-40 mL/min (depending on cartridge size) with wavelength monitoring at 254 and 280 nm. Preparatory HPLC was carried out using a Shimadzu preparative liquid chromatograph with the following specifications: Column: ACE 5 AQ (150×21.2 mm) with 5 μm particle size. Method 1: 25-100% MeOH/$H_2O$, 30 min; 100% MeOH, 5 min; 100-25% MeOH/$H_2O$, 4 min; 25% MeOH/$H_2O$, 1 min. Method 2: 8-100% MeOH/$H_2O$, 30 min; 100% MeOH, 5 min; 100-8% MeOH/$H_2O$, 4 min; 8% MeOH/$H_2O$, 1 min. Flow rate=17 mL/min with wavelength monitoring at 254 and 280 nm. Both solvents were spiked with 0.05% TFA. Where applicable (unless otherwise specified), resin bound bicarbonate was used to neutralize the trifluoroacetic acid salts obtained during preparatory HPLC purification. Analytical HPLC was carried out using an Agilent 1100 series instrument with the following specifications: Column: Luna 5 μ C18(2) 100A (150×4.60 mm) with 5 μm particle size. Flow rate=1.4 mL/min with wavelength monitoring at 254 nm. Gradient: 10-100% MeOH/$H_2O$, 18 min; 100% MeOH, 3 min; 100-10% MeOH/$H_2O$, 3 min; 10% MeOH/$H_2O$, 5 min. Both solvents were spiked with 0.05% TFA.

A. General synthetic scheme for HDACI compounds containing a bicyclic Cap group:

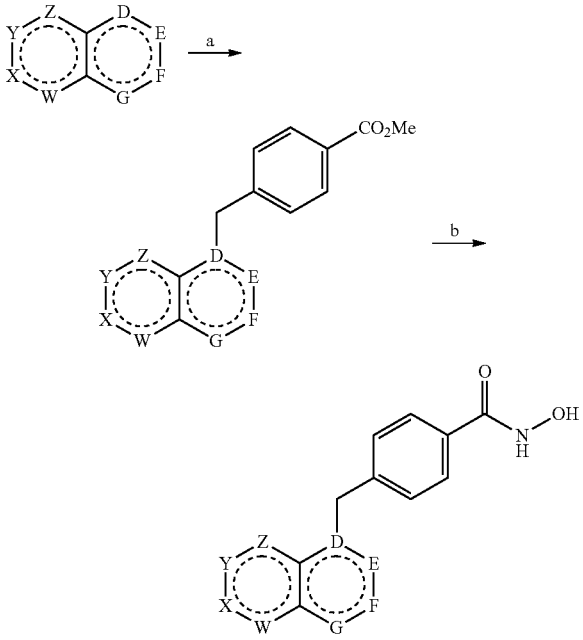

Reagents and conditions:
a) methyl 4-(bromomethyl)benzoate, KO$^t$Bu or NaH, DMF, 80° C., 2 h;
b) $NH_2OH$•HCl, NaOMe, MeOH, 0° C. to rt, 16 h.

B. General synthetic scheme for HDACI compound containing a five-membered monocyclic Cap group:

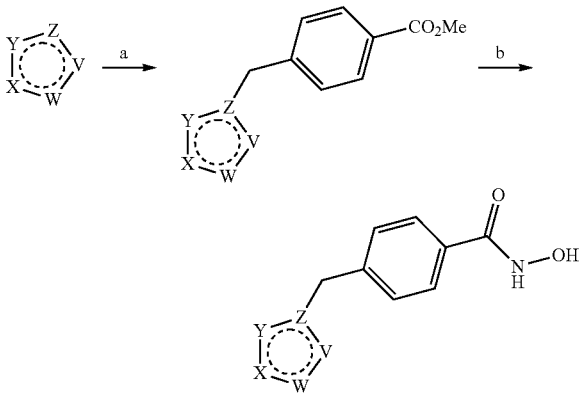

Reagents and conditions:
a) methyl 4-(bromomethyl)benzoate, KO$^t$Bu, DMF, 80° C., 2 h;
b) $NH_2OH$•HCl, NaOMe, MeOH, 0° C. to rt, 16 h.

C. General synthetic scheme for HDACI compounds containing a six-membered monocyclic Cap group:

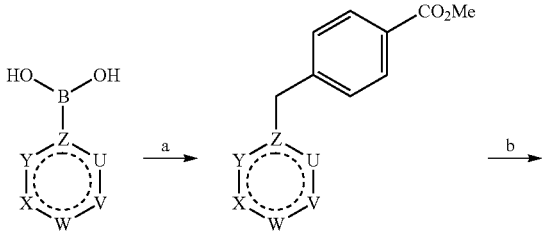

-continued

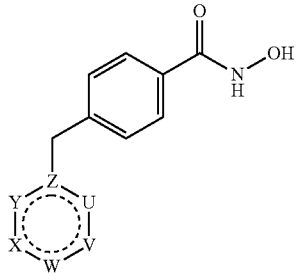

Reagents and conditions:
a) Tetrakis(triphenylphosphine)palladium(0), methyl 4-(bromomethyl)benzoate, $Na_2CO_3$, DME or diglyme, $H_2O$, 100° C., 4 h;
b) $NH_2OH$•HCl, NaOMe, MeOH, 0° C. to rt, 16 h.

D. General synthetic scheme for HDACI compounds containing an acyclic Cap group:

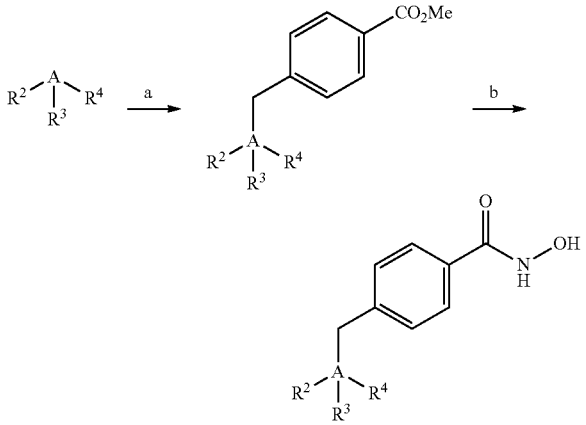

Reagents and conditions:
a) methyl 4-(bromomethyl)benzoate, KO$^t$Bu, DMF, 80° C., 2 h;
b) $NH_2OH$•HCl, NaOMe, MeOH, 0° C. to rt, 16 h.

General Procedure A: NaH (1 mol equiv) was dissolved in anhydrous DMF (5 mL/mmol) under argon and cooled to 0° C. To it was added the appropriate bicyclic Cap group (1 mol equiv) dissolved in anhydrous DMF (3 mL/mmol). The reaction was stirred for 15 min at 0° C. followed by the addition of methyl 4-(bromomethyl)benzoate (1 mol equiv) in anhydrous DMF (2 mL/mmol). The reaction was stirred for 2 h at 70° C. and then quenched by the addition of $H_2O$ (30 mL). The organic products were extracted with EtOAc (3×30 mL), washed with $H_2O$ (2×30 mL), brine (15 mL), dried over $Na_2SO_4$, filtered and concentrated in vacuo.

General Procedure B: The appropriate ester was dissolved/suspended in MeOH (3 mL/mmol) and added to a mixture of $NH_2OH.HCl$ (6 mol equiv) in MeOH (3 mL/mmol) which was followed by the addition of NaOMe (8 mol equiv of a 25% solution in MeOH). The mixture was stirred for 2 h at 0° C. followed by stirring for 22 h at RT. When the reaction was complete as evidenced by TLC, the reaction was quenched by the addition of trifluoroacetic acid (5 mol equiv of a 10% solution in DCM), filtered, and the filter cake was washed with additional MeOH (5-15 mL). The combined filtrate and wash were then concentrated in vacuo to yield the crude product which was dissolved in DMF and purified by preparatory HPLC.

General Procedure C: To a round bottom flask charged with methyl 4-(bromomethyl)benzoate (1 mol equiv) in DMF (4 mL/mmol) was added the appropriate 2-subsitituted benzimidazole (1 mol equiv) and $K_2CO_3$ (2 mol equiv) in succession. The resulting mixture was allowed to stir at 80° C. for 2-16 hrs and the reaction was monitored by TLC. Upon completion, the reaction was quenched with $H_2O$ (20 mL) and extracted with EtOAc (3×20 mL). The combined organic extracts were washed with $H_2O$ (2×15 mL), brine (15 mL), dried over $Na_2SO_4$, filtered and concentrated in vacuo.

General Procedure D: Solid NaOH (8 mol equiv) was dissolved in a 50% aq. solution of $NH_2OH$ (~50 mol equiv) at 0° C. Then, a solution of the appropriate ester (1 mol equiv) in THF/MeOH (9:9 mL/mmol) was added dropwise to the aforementioned, vigorously stirred hydroxylamine solution. Upon complete addition, the ice bath was removed and the reation was allowed to stir 15 min. The reaction was quenched with AcOH (10 mol equiv) and concentrated in vacuo to yield the crude product which was dissolved in DMF and purified by preparatory HPLC.

General Procedure E: The appropriate boronic acid (1 mol equiv), methyl 4-(bromomethyl)benzoate (1.2 mol equiv), tetrakis(triphenylphosphine)Pd(0) (0.02 mol equiv), and $K_2CO_3$ (2.1 mol equiv) were placed in a dry, sealed tube under Ar atmosphere. Diglyme (4 mL/mmol) and $H_2O$ (2 mL/mmol) were added through a rubber septa which was immediately replaced by the screw on cap. The reaction was heated to 100° C. and stirred for 4 h. Then, the reaction was diluted with $H_2O$ (20 mL) and the organic products were extracted with DCM (3×15 mL), washed with brine (15 mL), dried over $Na_2SO_4$, filtered and concentrated in vacuo.

An example of a present HDACI having a bicyclic Cap group is prepared as follows (see also General Synthetic Scheme A):

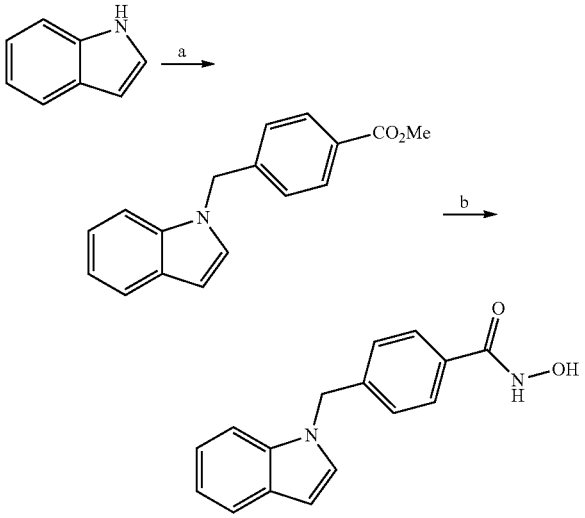

Reagents and conditions:
a) methyl 4-(bromomethyl)benzoate, NaH, DMF, 80° C., 2 h;
b) $NH_2OH \cdot HCl$, NaOMe, MeOH, 0° C. to rt, 16 h.

Examples of bicyclic Cap groups include, but are not limited to:

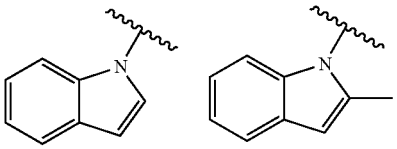

-continued

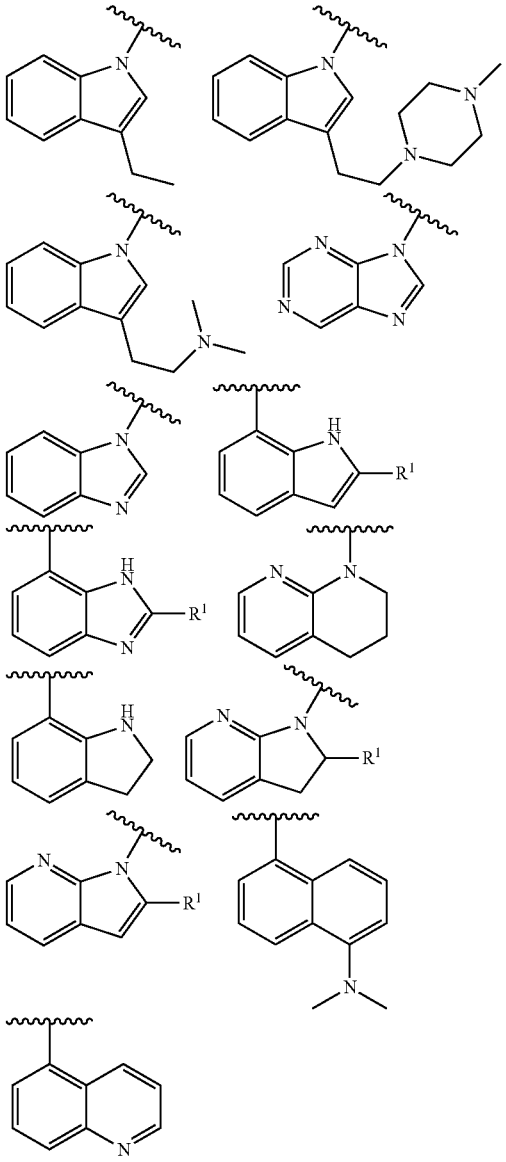

HDACIs having a bicyclic Cap group:

Methyl 4-((1H-indol-1-yl)methyl)benzoate (1)

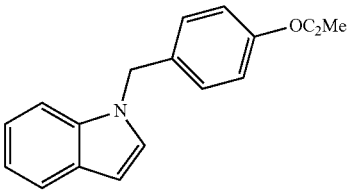

The title compound was prepared from 1H-indole (0.500 g, 4.27 mmol) according to General Procedure A and purified using automated column chromatography method 1. The product was isolated as a white solid (0.860 g, 76%). $^1H$ NMR (400 MHz, $CDCl_3$): δ 8.05 (d, J=8.23 Hz, 2H), 7.79 (d, J=6.9 Hz, 1H), 7.24 (m, 6H), 6.70 (d, J=3.05 (d, J=3.05 Hz, 1H), 5.35 (s, 2H), 3.97 (s, 3H). $^{13}C$ NMR (100 MHz, $CDCl_3$): δ 166.7, 142.9, 136.3, 130.1, 129.6, 128.9, 128.4, 126.7, 122.0, 121.2, 119.9, 109.7, 102.2, 52.2, 49.8. ESI- HRMS: calc. for $C_{17}H_{15}NO_2$: $[M+H]^+$=266.1176 m/z, found: $[M+H]^+$=266.1182 m/z.

4-((1H-Indol-1-yl)methyl)-N-hydroxybenzamide (2)

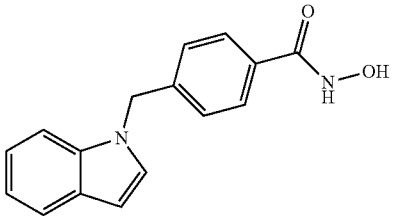

The title compound was synthesized from methyl 4-((1H-indol-1-yl)methyl)benzoate 1 (0.840 g, 3.17 mmol) according to General Procedure B (prep. HPLC method 1) and isolated as a white solid (0.443 g, 53%). $^1$H NMR (400 MHz, DMSO-$d_6$): δ 11.14 (S, 1H), 9.01 (br, 1H), 7.67 (d, J=8.1 Hz, 2H), 7.56 (d, J=7.77 Hz, 1H), 7.52 (d, J=3.1 Hz, 1H), 7.42 (d, J=8.1 Hz, 1H), 7.23 (d, J=8.1 Hz, 2H), 7.09 (t, J=7.2 Hz, 1H), 7.02 (t, J=7.5 Hz, 1H), 6.50 (d, J=3.0 Hz, 1H), 5.48 (s, 2H). $^{13}$C NMR (100 MHz, DMSO-$d_6$): δ 164.4, 141.9, 136.1, 132.3, 129.6, 128.7, 127.6, 127.3, 121.7, 120.9, 119.6, 110.5, 101.6, 49.2. ESI-HRMS: calc. for $C_{16}H_{14}N_2O_2$: $[M+H]^+$=267.1128 m/z, found: $[M+H]^+$=267.1137 m/z.

Methyl 4-((2-methyl-1H-indol-1-yl)methyl)benzoate (3)

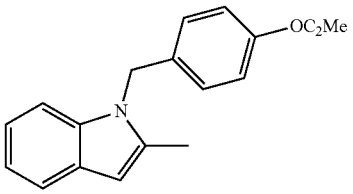

The title compound was prepared from 2-methyl-1H-indole (2.00 g, 15.3 mmol) according to General Procedure A and purified using automated column chromatography method 1. The product was isolated as a white solid (2.87 g, 67%). $^1$H NMR (400 MHz, DMSO-$d_6$): δ 7.89 (d, J=8.0 Hz, 2H), 7.48 (d, J=7.6 Hz, 1H), 7.33 (d, J=7.6 Hz, 1H), 7.09 (d, J=8.0 Hz, 2H), 7.01 (m, 2H), 6.32 (s, 1H), 5.49 (s, 2H), 3.81 (s, 3H), 2.34 (s, 3H). $^{13}$C NMR (100 MHz, DMSO-$d_6$): δ 166.4, 144.5, 137.2, 137.1, 130.0, 128.9, 128.2, 126.8, 120.9, 119.8, 119.7, 109.9, 100.7, 52.5, 45.9, 12.8.

N-Hydroxy-4-((2-methyl-1H-indol-1-yl)methyl) benzamide (4)

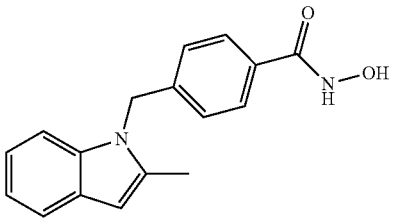

The title compound was synthesized from methyl 4-((2-methyl-1H-indol-1-yl)methyl)benzoate 3 (0.259 g, 0.937 mmol) according to General Procedure B (prep. HPLC method 1) and isolated as a light brown solid (86 mg, 33%). $^1$H NMR (400 MHz, DMSO-$d_6$): δ 11.13 (s, 1H), 8.96 (br, 1H), 7.65 (d, J=8.2 Hz, 2H), 7.46 (d, J=7.1 Hz, 1H), 7.33 (d, J=7.5 Hz, 1H), 7.00 (m, 4H), 6.31 (s, 1H), 5.45 (s, 2H), 2.36 (s, 3H). $^{13}$C NMR (100 MHz, DMSO-$d_6$): δ 166.0, 142.5, 136.6, 136.0, 128.9, 127.9, 127.0, 126.1, 120.6, 119.5, 119.4, 108.6, 100.5, 45.7, 12.3. ESI-HRMS: calc. for $C_{17}H_{16}N_2O_2$: $[M+H]^+$=281.1285 m/z, found: $[M+H]^+$=281.1283 m/z.

Methyl 4-((3-methyl-1H-indol-1-yl)methyl)benzoate (5)

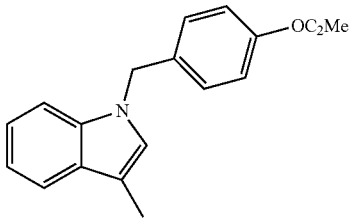

The title compound was prepared from 3-methyl-1H-indole (0.500 g, 3.81 mmol) according to General Procedure A and purified using automated column chromatography method 1. The product was isolated as a white solid (0.668 g, 63%). $^1$H NMR (400 MHz, $CDCl_3$): δ 8.04 (d, J=7.9 Hz, 2H), 7.72 (d, J=7.4 Hz, 1H), 7.24 (m, 5H), 6.94 (s, 1H), 5.31 (s, 2H), 3.97 (s, 3H), 2.46 (s, 3H). $^{13}$C NMR (100 MHz, $CDCl_3$): δ 166.7, 143.1, 136.5, 130.0, 129.4, 129.0, 126.6, 125.7, 1221.8, 119.1, 119.0, 109.3, 71.8, 52.1, 49.5, 9.6. ESI-HRMS: calc. for $C_{18}H_{17}NO_2$: $[M+H]^+$=280.1332 m/z, found: $[M+H]^+$=280.1322 m/z.

N-Hydroxy-4-((3-methyl-1H-indol-1-yl)methyl) benzamide (6)

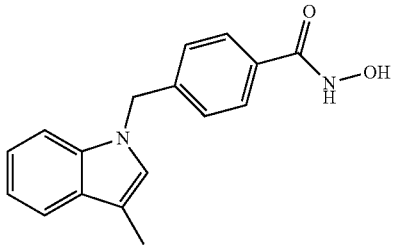

The title compound was synthesized from methyl 4-((3-methyl-1H-indol-1-yl)methyl)benzoate 5 (0.200 g, 0.716 mmol) according to General Procedure B (prep. HPLC method 1) and isolated as a white solid (0.108 g, 54%). $^1$H NMR (400 MHz, DMSO-$d_6$): δ 11.13 (s, 1H), 8.99 (s, 1H), 7.66 (d, J=8.4 Hz, 2H), 7.50 (d, J=8.0 Hz, 1H), 7.37 (d, J=8.0 Hz, 1H), 7.23 (m, 3H), 7.06 (td, J=8.0, 1.2 Hz, 1H), 7.03 (td, J=7.6, 0.8 Hz, 1H), 5.39 (s, 2H), 2.27 (s, 3H). $^{13}$C NMR (100 MHz, DMSO-$d_6$): δ 166.48, 142.50, 136.57, 131.08, 128.99, 126.97, 126.49, 125.78, 121.15, 118.39, 118.35, 110.36, 109.09, 48.62, 8.25. ESI-HRMS: calc. for $C_{17}H_{16}N_2O_2$: $[M+H]^+$=279.1139 m/z, found: $[M+H]^+$=279.1144 m/z.

Methyl 4-((2,3-dimethyl-1H-indol-1-yl)methyl)benzoate (7)

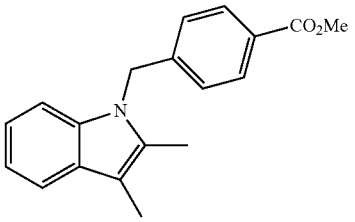

The title compound was prepared from 2,3-dimethyl-1H-indole (0.500 g, 3.44 mmol) according to General Procedure A and purified using automated column chromatography method 1. The product was isolated as a viscous yellow oil (0.652 g, 65%). $^1$H NMR (400 MHz, $CDCl_3$): δ 7.95 (d, J=8.3 Hz, 2H), 7.57 (dd, J=3.1 Hz, 2.2 Hz, 1H), 7.16 (m, 3H), 7.04 (d, J=8.2 Hz, 2H), 5.36 (s, 2H), 3.91 (s, 3H), 2.32 (s, 3H), 2.29 (s, 3H). $^{13}$C NMR (100 MHz, $CDCl_3$): δ 166.8, 143.5, 136.3, 132.2, 130.1, 129.2, 128.7, 126.0, 121.0, 119.1, 118.1, 108.6, 107.4, 52.1, 46.4, 10.1, 8.9. ESI-HRMS: calc. for $C_{19}H_{19}NO_2$: $[M+H]^+$=294.1489 m/z, found: $[M+H]^+$=294.1503 m/z.

4-((2,3-Dimethyl-1H-indol-1-yl)methyl)-N-hydroxybenzamide (8)

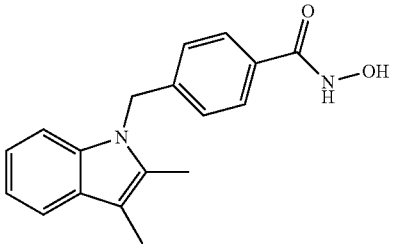

The title compound was synthesized from methyl 4-((2,3dimethyl-1H-indol-1-yl)methyl)benzoate 7 (0.632 g, 2.15 mmol) according to General Procedure B (prep. HPLC method 1) and isolated as a white solid (0.487 g, 77%). $^1$H NMR (400 MHz, DMSO-$d_6$): δ 11.13 (s, 1H), 9.00 (br, 1H), 7.66 (d, J=8.2 Hz, 2H), 7.45 (d, J=6.9 Hz, 1H), 7.32 (d, J=7.3 Hz, 1H), 7.01 (m, 4H), 5.43 (s, 2H), 2.27 (s, 3H), 2.22 (s, 3H). $^{13}$C NMR (100 MHz, DMSO-$d_6$): δ 164.4, 142.4, 136.4, 133.0, 132.1, 128.6, 127.6, 126.5, 120.9, 119.0, 118.1, 109.6, 106.5, 45.9, 10.3, 9.2. ESI-HRMS: calc. for $C_{18}H_{18}N_2O_2$: $[M+H]^+$=295.1441 m/z, found: $[M+H]^+$=295.1453 m/z.

Methyl 4-((3-benzyl-1H-indol-1-yl)methyl)benzoate (9)

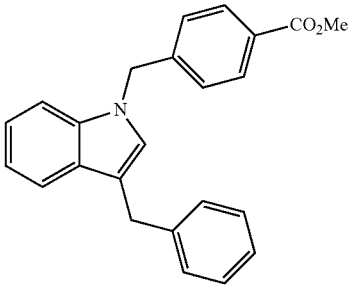

To a solution of methyl 4-((1H-indol-1-yl)methyl)benzoate 1 (0.250 g, 0.94 mmol) and benzaldehyde (96 μL, 0.94 mmol) in DCM (10 mL) at 0° C. was added $SiEt_3H$ (0.45 mL, 2.83 mmol) followed by trifluoroacetic acid (0.14 mL, 1.88 mmol). The reaction was stirred at 0° C. for 1 h. The reaction was then adjusted to pH 10 with 2 N NaOH and the organic products were extracted with DCM (3×15 mL). The combined organic fractions were washed with brine (15 mL), dried with $Na_2SO_4$, filtered and concentrated in vacuo. The title compound was isolated using automated column chromatography method 1 (0.262 g, 78%). $^1$H NMR (400 MHz, $CDCl_3$): δ 7.97 (d, J=8.0 Hz, 2H), 7.56 (d, J=8.0 Hz, 1H), 7.32-7.27 (m, 4H), 7.23-7.10 (m, 6H), 6.87 (s, 1H), 5.33 (s, 2H), 4.15 (s, 2H), 3.91 (s, 3H). $^{13}$C NMR (100 MHz, $CDCl_3$): δ 166.8, 143.0, 141.2, 136.8, 130.1, 129.5, 128.7, 128.4, 128.3, 126.6, 126.5, 126.0, 122.1, 119.5, 119.3, 115.4, 109.6, 52.2, 49.7, 31.6.

4-((3-Benzyl-1H-indol-1-yl)methyl)-N-hydroxybenzamide (10)

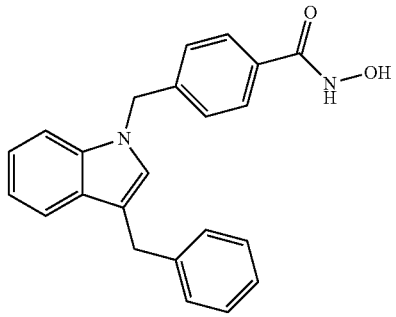

The title compound was synthesized from methyl 4-(3-benzyl-1H-indol-1-yl)methyl)benzoate 9 (0.200 g, 0.563 mmol) according to General Procedure B (prep. HPLC method 1) and isolated as a white solid (80 mg, 40%). $^1$H NMR (400 MHz, DMSO-$d_6$): δ 11.20 (br, 1H), 7.67 (d, J=8.2 Hz, 2H), 7.45 (d, J=7.9 Hz, 1H), 7.36 (d, J=8.2 Hz, 1H), 7.27 (m, 6H), 7.15 (d, J=6.7 Hz, 1H), 7.07 (t, J=7.9 Hz, 1H), 6.96 (t, J=7.8 Hz, 1H), 5.40 (s, 2H), 4.05 (s, 2H). $^{13}$C NMR (100 MHz, MeOD): δ 164.48, 142.06, 141.91, 136.63, 132.18, 128.83, 128.68, 128.06, 127.57, 127.41, 127.29, 126.17, 121.83, 119.44, 119.19, 114.53, 110.45, 49.01, 31.30. ESI-HRMS: calc. for $C_{23}H_{20}N_2O_2$: $[M+H]^+$=357.1598 m/z, found: $[M+H]^+$=357.1597 m/z.

Methyl 4-((9H-purin-9-yl)methyl)benzoate (11)

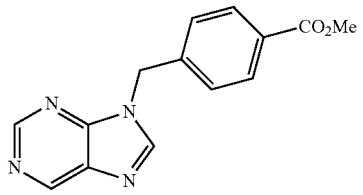

The title compound was prepared from 9H-purine (0.500 g, 3.81 mmol) according to General Procedure A (substituting KO$^t$Bu for NaH) and purified using automated column chromatography method 2. The pH was adjusted to 10 with 1 N NaOH prior to extraction with EtOAc. The product was isolated as a white solid (0.287 g, 64%). $^1$H NMR (400 MHz, DMSO-$d_6$): δ 9.20 (s, 1H), 8.94 (s, 1H), 8.78 (s, 1H), 7.92 (d, J=8.3 Hz, 2H), 7.44 (d, J=8.3 Hz, 2H), 5.62 (s, 2H), 3.82 (s, 3H). $^{13}$C NMR (100 MHz, DMSO-$d_6$): δ 165.9, 152.3, 151.2, 148.0, 147.2, 141.7, 133.7, 129.7, 129.2, 127.8, 52.2, 46.1. ESI-HRMS: calc. for $C_{14}H_{12}N_4O_2$: $[M+H]^+$=269.1033 m/z, found: $[M+H]^+$=269.1032 m/z.

4-((9H-Purin-9-yl)methyl)-N-hydroxybenzamide (12)

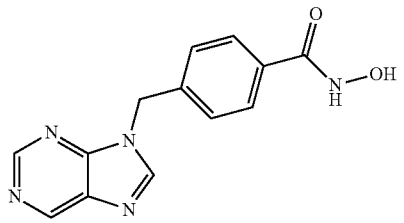

The title compound was synthesized from methyl 4-((9H-purin-9-yl)methyl)benzoate 11 (0.287 g, 1.07 mmol) according to General Procedure B (prep. HPLC method 2) and isolated as a white solid (288 mg, 45%). $^1$H NMR (400 MHz, DMSO-$d_6$): δ 11.18 (br, 1H), 9.20 (s, 1H), 8.95 (s, 1H), 8.78 (s, 1H), 7.71 (d, J=8.2 Hz, 2H), 7.40 (d, J=8.2 Hz, 2H), 5.58 (s, 2H), 3.73 (br, 1H). $^{13}$C NMR (100 MHz, DMSO-$d_6$): δ 164.2, 152.6, 151.5, 148.4, 147.5, 139.8, 134.0, 132.9, 128.0, 127.8, 46.5. ESI-HRMS: calc. for $C_{13}H_{11}N_5O_2$: $[M+H]^+$=270.0986 m/z, found: $[M+H]^+$=270.0992 m/z.

Methyl 4-((7H-purin-7-yl)methyl)benzoate (13)

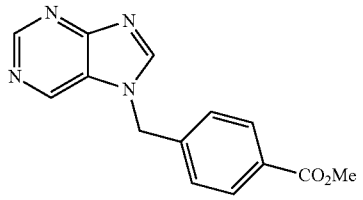

The title compound was prepared from 9H-purine (0.500 g, 3.81 mmol) according to General Procedure A (substituting KO$^t$Bu for NaH) and purified using automated column chromatography method 2. The pH was adjusted to 10 with 1 N NaOH prior to extraction with EtOAc. The product was isolated as a viscous yellow oil (0.108 g, 24%). $^1$H NMR (400 MHz, DMSO-$d_6$): δ 9.16 (s, 1H), 9.02 (s, 1H), 8.97 (s, 1H), 7.94 (d, J=8.2 Hz, 2H), 7.51 (d, J=8.2 Hz, 2H), 5.74 (s, 2H), 3.83 (s, 3H). $^{13}$C NMR (100 MHz, DMSO-$d_6$): δ 165.9, 160.4, 152.0, 150.2, 141.2, 140.6, 129.8, 129.5, 128.0, 125.0, 52.2, 48.4. ESI-HRMS: calc. for $C_{14}H_{12}N_4O_2$: $[M+H]^+$=269.1033 m/z, found: $[M+H]^+$=269.1036 m/z.

4-((7H-Purin-7-yl)methyl)-N-hydroxybenzamide (14)

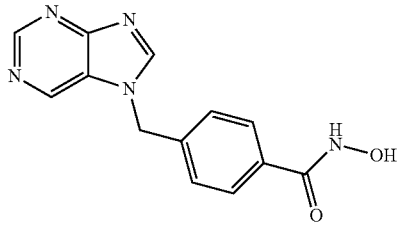

The title compound was synthesized from methyl 4-((7H-purin-7-yl)methyl)benzoate 13 (0.108 g, 0.40 mmol) according to General Procedure B (prep. HPLC method 2) and isolated as a white solid (50 mg, 46%). $^1$H NMR (400 MHz, DMSO-$d_6$): δ 11.21 (br, 1H), 9.16 (s, 1H), 9.00 (s, 1H), 8.95 (s, 1H), 7.73 (d, J=8.2 Hz, 2H), 7.47 (d, J=8.2 Hz, 2H), 6.75 (br, 1H), 5.68 (s, 2H). $^{13}$C NMR (100 MHz, DMSO-$d_6$): δ 164.1, 160.7, 152.5, 150.3, 141.2, 139.3, 133.1, 128.2, 127.9, 125.3, 48.8. ESI-HRMS: calc. for $C_{13}H_{11}N_5O_2$: $[M+H]^+$=270.0986 m/z, found: $[M+H]^+$=270.0984 m/z.

3-[2-(4-Methyl-piperazin-1-yl)-ethyl]-1H-indole (15)

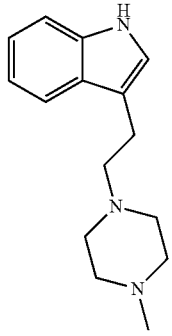

Tryptophol (0.500 g, 3.10 mmol) and $Et_3N$ (1 mL) were dissolved in DCM (2 mL) and then mesyl chloride (0.24 mL, 3.102 mmol) was added dropwise at RT. The reaction was stirred for 3 h and then volatiles were removed in vacuo. The crude mesylate was taken up in DCM (3 mL) and to it was added 1-methylpiperazine (1.72 mL, 15.5 mmol) and $Et_3N$ (1 mL). The reaction was heated to 40° C. and stirred overnight. After completion, the reaction mixture was poured into cold water, the pH was adjusted to 10 with 1 N NaOH and the organic products were extracted with DCM (3×15 mL). The combined organic extracts were washed with brine (15 mL), dried with $Na_2SO_4$, filtered and concentrated in vacuo. Automated column chromatography method 2 was used to isolate the title compound (0.42 g, 56%). $^1$H NMR (400 MHz, $CDCl_3$): δ 7.54 (d, J=7.8 Hz, 1H), 7.34 (d, J=8.1 Hz, 1H), 7.10 (t, J=7.1 Hz, 1H), 7.03 (t, J=7.3 Hz, 1H), 6.98 (s, 1H), 2.87 (t, J=7.8 Hz, 2H), 2.58 (t, J=5.9 Hz, 2H), 2.38 (br, 8H), 2.17 (s, 3H). $^{13}$C NMR (100 MHz, $CDCl_3$): δ 136.7, 127.4, 121.8, 121.0, 118.3, 118.0, 112.4, 111.0, 58.9, 54.1, 52.2, 44.6, 22.2. ESI-HRMS: calc. for $C_{15}H_{21}N_3$: $[M+H]^+$=244.1808 m/z, found: $[M+H]^+$=244.1797 m/z.

4-{3-[2-(4-Methyl-piperazin-1-yl)-ethyl]-indol-1-ylmethyl}-benzoic acid methyl ester (16)

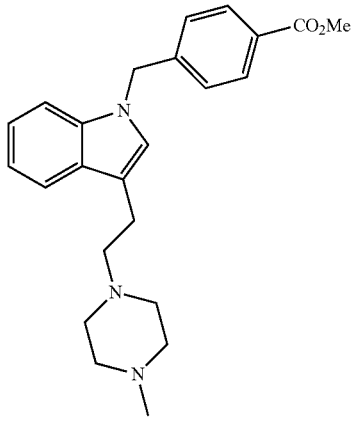

The title compound was prepared from 3-[2-(4-methyl-piperazin-1-yl)-ethyl]-1H-indole 15 (0.400 g, 1.64 mmol) according to General Procedure A (substituting KO'Bu for NaH). The pH was adjusted to 10 with 1 N NaOH prior to extraction with EtOAc. The product was purified via automated column chromatography method 2 (0.412 g, 64%). $^1$H NMR (400 MHz, $CDCl_3$): δ 7.79 (d, J=8.3 Hz, 2H), 7.56 (d, J=7.0 Hz, 1H), 7.04 (m, 6H), 5.14 (s, 2H), 3.76 (s, 3H), 2.90 (t, J=7.6 Hz, 2H), 2.63 (t, J=8.6 Hz, 2H), 2.46 (br, 8H), 2.23 (s, 3H). $^{13}$C NMR (100 MHz, $CDCl_3$): δ 166.2, 143.3, 136.2, 129.1, 128.6, 127.8, 126.1, 125.4, 121.2, 118.4, 118.2, 112.6, 109.1, 58.4, 53.8, 51.9, 50.8, 48.4, 44.3, 21.8. ESI-HRMS: calc. for $C_{24}H_{29}N_3O_2$: $[M+H]^+$=392.2333 m/z, found: $[M+H]^+$=392.2343 m/z.

N-Hydroxy-4-{3-[2-(4-methyl-piperazin-1-yl)ethyl]-indol-1-ylmethyl}-benzamide (17)

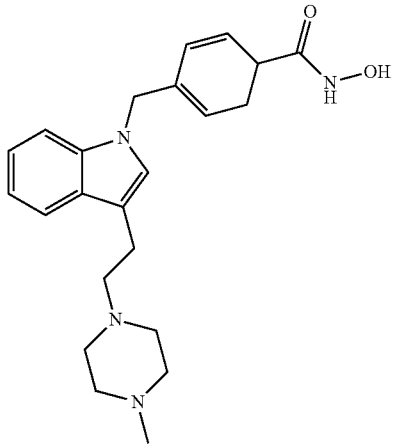

The title compound was synthesized from 4-{3-[2-(4-Methyl-piperazin-1-yl)-ethyl]-indol-1-ylmethyl}-benzoic acid methyl ester 16 (0.412 g, 1.05 mmol) according to General Procedure B (prep. HPLC method 2) and isolated as a white solid (0.265 g, 64%). $^1$H NMR (400 MHz, DMSO-$d_6$): δ 7.67 (d, J=7.8 Hz, 3H), 7.42 (m, 2H), 7.24 (d, J=7.9 Hz, 2H), 7.12 (t, J=7.2 Hz, 1H), 7.04 (t, J=7.4 Hz, 1H), 5.43 (s, 2H), 3.81 (m, 4H), 3.53 (br, 4H), 3.40 (br, 2H), 3.25 (br, 2H), 2.84 (s, 3H). $^{13}$C NMR (100 MHz, DMSO-$d_6$): δ 163.9, 141.4, 136.1, 131.9, 127.3, 127.2, 127.1, 127.0, 121.8, 119.0, 118.9, 110.3, 109.2, 55.6, 49.6, 48.7, 48.0, 42.2, 19.4. ESI-HRMS: calc. for $C_{23}H_{28}N_4O_2$: $[M+H]^+$=393.2285 m/z, found: $[M+H]^+$=393.2299 m/z.

2-(1H-Indol-3-yl)-N,N-dimethylethanamine

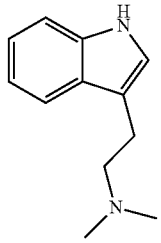

$^1$H NMR (400 MHz, $CDCl_3$): δ 8.68 (s, 1H), 7.63 (d, J=7.7 Hz, 1H), 7.35 (d, J=8.0 Hz, 1H), 7.21 (t, J=7.1 Hz, 1H), 7.14 (t, J=7.5 Hz, 1H), 6.97 (s, 1H), 3.00 (t, J=7.5 Hz, 2H), 2.72 (t, J=8.4 Hz, 2H), 2.40 (s, 6H).

Methyl 4-((3-(2-(dimethylamino)ethyl)-1H-indol-1-yl)methyl)benzoate (18)

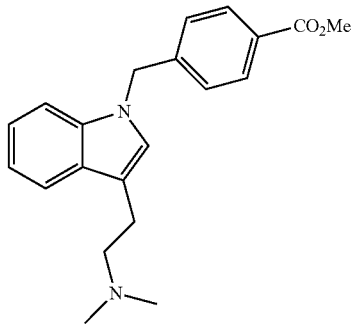

The title compound was prepared from 2-(1H-indol-3-yl)-N,N-dimethylethanamine (0.130 g, 0.69 mmol) according to General Procedure A. The pH was adjusted to 10 with 1 N NaOH prior to extraction with EtOAc. The product was purified via automated column chromatography method 2 (0.174 g, 61%). $^1$H NMR (400 MHz, $CDCl_3$): δ 7.97 (d, J=8.3 Hz, 2H), 7.65 (d, J=7.5 Hz, 1H), 7.17 (m, 5H), 6.99 (s, 1H), 5.34 (s, 2H), 3.91 (s, 3H), 3.04 (t, J=7.6 Hz, 2H), 2.75 (m, 2H), 2.43 (s, 6H).

4-((3-(2-(Dimethylamino)ethyl)-1H-indol-1-yl) methyl)-N-hydroxybenzamide (19)

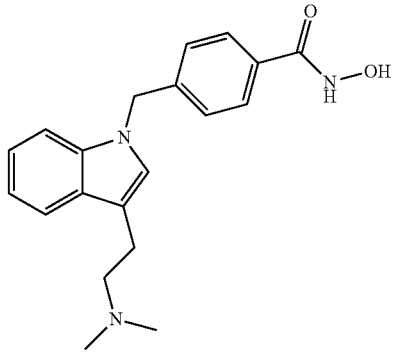

The title compound was synthesized from methyl 4-((3-(2-(dimethylamino)ethyl)-1H-indol-1-yl)methyl)benzoate 18 (0.412 g, 1.05 mmol) according to General Procedure B (prep. HPLC method 2) and isolated as a white solid (18 mg, 11%). $^1$H NMR (400 MHz, MeOD): δ 7.66 (m, 3H), 7.29 (m, 2H), 7.31 (d, J=8.0 Hz, 2H), 7.13 (m, 2H), 5.41 (s, 2H), 3.48 (t, J=7.4 Hz, 2H), 3.24 (t, J=8.3 Hz, 2H), 2.97 (s, 6H). $^{13}$C NMR (100 MHz, MeOD): δ 166.33, 141.99, 136.78, 131.29, 127.48, 127.05, 126.74, 126.65, 121.88, 119.23, 118.09, 109.73, 109.73, 108.70, 57.65, 48.90, 42.12, 20.35. ESI-HRMS: calc. for $C_{20}H_{23}N_3O_2$: $[M+H]^+$=338.1863 m/z, found: $[M+H]^+$=338.1865 m/z.

Methyl 4-((3-((dimethylamino)methyl)-2-methyl-1H-indol-1-yl)methyl)benzoate (20)

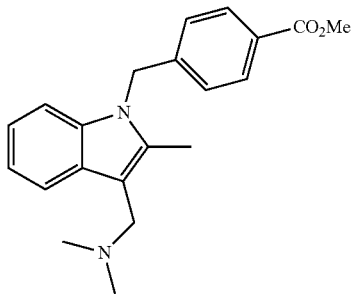

Methyl 4-((2-methyl-1H-indol-1-yl)methyl)benzoate 3 (0.500 g, 1.90 mmol) and dimethylformiminium chloride (0.200 g, 2.15 mmol) were heated to reflux in a solution of DCM (5 mL) and DMF (2 mL) for 20 h. The reaction was then cooled to RT and DCM (50 mL) was added along with sat. $NaHCO_3$ (20 mL). The organic fraction was isolated and the aqueous solution was further extracted with DCM (2×20 mL). The combined organic fractions were washed with $H_2O$ (20 mL), brine (20 mL), dried with $Na_2SO_4$ and concentrated in vacuo. The desired product was purified via automated column chromatography method 2 (0.221 g, 37%). $^1$H NMR (400 MHz, $CDCl_3$): δ 7.94 (d, J=8.1 Hz, 2H), 7.69 (m, 1H), 7.14 (m, 3H), 7.02 (d, J=8.0 Hz, 2H), 5.38 (s, 2H), 3.90 (s, 3H), 3.62 (s, 2H), 2.35 (s, 3H), 2.30 (s, 6H).

4-((3-((Dimethylamino)methyl)-2-methyl-1 H-indol-1-yl)methyl)-N-hydroxybenzamide (21)

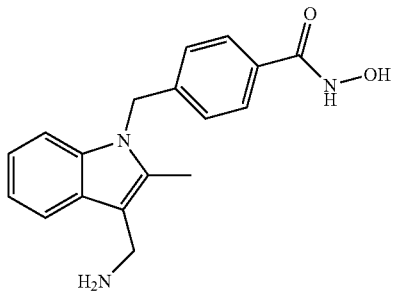

The title compound was synthesized from methyl 4-((3-((dimethylamino)methyl)-2-methyl-1H-indol-1-yl)methyl) benzoate 20 (0.124 g, 1.78 mmol) according to General Procedure B (prep. HPLC method 2) and isolated as a white solid (0.100 g, 80%). $^1$H NMR (400 MHz, MeOD): δ 7.72 (br, 1H), 7.68 (d, J=7.8 Hz, 2H), 7.38 (br, 1H), 7.21 (br, 2H), 7.08 (d, J=7.9 Hz, 2H), 5.56 (s, 2H), 4.57 (s, 2H), 2.91 (s, 6H), 2.48 (s, 3H).

4-((1H-Indol-1-yl)methyl)benzamide (22)

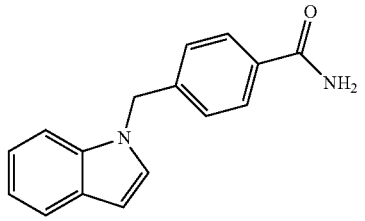

Methyl 4-((1H-indol-1-yl)methyl)benzoate 1 was dissolved in MeOH (10 mL) and to it was added a 30% solution of ammonium hydroxide (5 mL). The reaction was heated to reflux for 16 h after which it was cooled to RT and $H_2O$ (30 mL) was added. The organic products were extracted with EtOAc (3×15 mL), washed with brine (15 mL), dried with $Na_2SO_4$ and concentrated in vacuo. The crude product was dissolved in DMF and purified by preparatory HPLC method 1. The title compound was isolated as a white solid (37 mg, 13%). $^1$H NMR (400 MHz, MeOD): δ 7.79 (d, J=7.9 Hz, 2H), 7.58 (d, J=7.8 Hz, 1H), 7.29 (m, 2H), 7.19 (d, J=8.0 Hz, 2H), 7.11 (t, J=7.2 Hz, 1H), 7.04 (t, J=7.5 Hz, 1H), 6.53 (d, J=2.8 Hz, 1H), 5.47 (s, 2H). $^{13}$C NMR (100 MHz, MeOD): δ 170.59, 142.41, 136.24, 132.64, 128.93, 128.14, 127.57, 126.36, 121.13, 120.32, 118.99, 109.29, 101.14, 48.93. ESI-LRMS: $[M+H]^+$=251.1 m/z. ESI-HRMS: calc. for $C_{16}H_{14}N_2O$: $[M+H]^+$=251.1179 m/z, found: $[M+H]^+$=251.1179 m/z.

1-(4-((1H-Indol-1-yl)methyl)phenyl)ethanone (23)

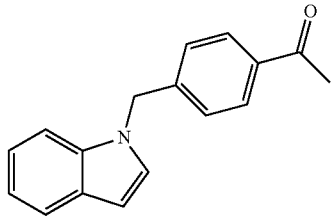

The title compound was prepared from 1H-indole (0.55 g, 4.69 mmol) and 1-(4-(bromomethyl)phenyl)ethanone (1.00 g, 4.69 mmol) following a procedure similar to General Procedure A. The title compound was purified using automated column chromatography method 1 (0.410 g, 35%). $^1$H NMR (400 MHz, $CDCl_3$): δ 7.90 (d, J=8.2 Hz, 2H), 7.69 (d, J=7.5 Hz, 1H), 7.21 (m, 6H), 6.61 (d, J=3.1 Hz, 1H), 5.41 (s, 2H), 2.58 (s, 3H). $^{13}$C NMR (100 MHz, MeOD): δ 198.58, 143.95, 136.22, 136.04, 128.94, 128.39, 128.17, 126.51, 121.19, 120.37, 119.06, 109.29, 101.24, 48.95, 25.23. ESI-HRMS: calc. for $C_{17}H_{15}NO$: $[M+H]^+$=250.1226 m/z, found: $[M+H]^+$=250.1232 m/z.

3-(1H-Indol-1-yl)propanamide (24)

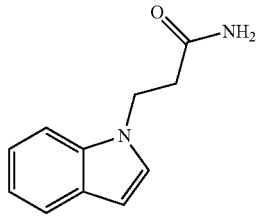

The title compound was prepared from 1H-indole (0.500 g, 4.27 mmol) and 3-bromopropanamide (0.650 g, 4.27 mmol) following a procedure similar to General Procedure A. The title compound was purified by preparatory HPLC method 1 and isolated as a white solid (0.339 g, 42%). $^1$H NMR (400 MHz, MeOD): δ 7.53 (d, J=7.9 Hz, 1H), 7.44 (d, J=8.3 Hz, 1H), 7.19 (d, J=2.9 Hz, 1H), 7.16 (t, J=7.5 Hz, 1H), 7.03 (t, J=7.4 Hz, 1H), 6.42 (d, J=2.8 Hz, 1H), 4.47 (t, J=6.8 Hz, 2H), 2.70 (t, J=6.8 Hz, 2H). $^{13}$C NMR (100 MHz, DMSO-$d_6$): δ 172.4, 135.9, 129.0, 128.6, 121.4, 120.8, 119.4, 110.2, 101.0, 42.3, 36.2. ESI-LRMS: $[M+H]^+$=189.1 m/z. ESI-HRMS: calc. for $C_{11}H_{12}N_2O_1$: $[M+H]^+$=189.1022 m/z, found: $[M+H]^+$=189.1030 m/z.

N-Hydroxy-3-(1H-indol-1-yl)propanamide (25)

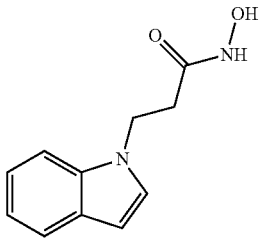

NaH (0.444 g, 11.1 mmol) was dissolved in anhydrous DMF (5 mL) under argon and cooled to 0° C. To it was added 1H-indole (1.00 g, 8.54 mmol) dissolved in anhydrous DMF (5 mL). The reaction was stirred for 15 min at 0° C. followed by the addition of ethyl 3-bromopropanoate (1.10 mL, 8.54 mmol). The reaction was then stirred for 3 h at 70° C. and then quenched by the addition of $H_2O$ (30 mL). The organic products were extracted with EtOAc (3×30 mL), washed with $H_2O$ (2×30 mL), brine (15 mL), dried with $Na_2SO_4$, filtered and concentrated in vacuo. The crude product was purified using automated column chromatography method 1 to yield ethyl 3-(1H-indol-1-yl)propanoate (0.759 g, 3.49 mmol). The title compound was then prepared from ethyl 3-(1H-indol-1yl)propanoate (0.486 g, 5.52 mmol) according to General Procedure B (prep. HPLC method 1) and isolated as a white solid (0.104 g, 23%). $^1$H NMR (400 MHz, MeOD): δ 7.53 (d, J=7.83 Hz, 1H), 7.42 (d, J=8.1 Hz, 1H), 7.16 (m, 2H), 7.02 (t, J=7.4 Hz, 1H), 6.41 (d, J=2.8 Hz, 1H), 4.48 (t, J=6.5 Hz, 2H), 2.56 (t, J=6.6 Hz, 2H). ESI-LRMS: $[M+H]^+$=205.1 m/z. ESI-HRMS: calc. for $C_{11}H_{12}N_2O_2$: $[M+H]^+$=205.0972 m/z, found: $[M+H]^+$=205.0971 m/z.

Methyl 4-((1H-benzo[d]imidazol-1-yl)methyl)benzoate (26)

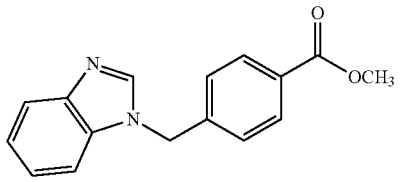

The title compound was prepared from 1H-benzo[d]imidazole (236 mg, 2.0 mmol) according to General Procedure C and purified using automated column chromatography method 2. The product was isolated as an off-white waxy solid (501 mg, 94%). $^1$H NMR (400 MHz, $CDCl_3$) δ 8.02-7.98 (m, 3H), 7.85 (d, J=7.6 Hz, 1H), 7.31-7.28 (m, 2H), 7.26-7.22 (m, 3H), 5.43 (s, 2H), 3.91 (s, 3H). $^{13}$C NMR (100 MHz, $CDCl_3$) δ 166.41, 143.95, 143.13, 140.46, 133.72, 130.28, 130.14, 126.81, 123.26, 122.43, 120.54, 109.83, 52.19, 48.45 ESI-LRMS: $[M+H]^+$=267 m/z.

4-((1H-Benzo[d]imidazol-1-yl)methyl)-N-hydroxybenzamide.TFA (27)

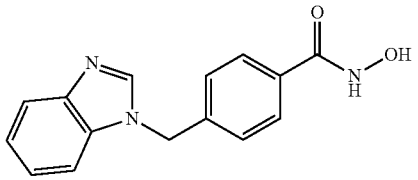

The title compound was synthesized from methyl 4-((1H-benzo[d]imidazol-1-yl)methyl)benzoate 26 (93 mg, 0.349 mmol) according to General Procedure D (prep. HPLC method 2) and isolated as a white solid (81 mg, 87%). $^1$H NMR (400 MHz, DMSO-$d_6$) δ 11.21 (br s, 1H), 9.35 (s, 1H), 7.83 (m, 1H), 7.74 (m, 3H), 7.47 (m, 4H). $^{13}$C NMR (100 MHz, DMSO-$d_6$) δ 163.59, 142.78, 138.12, 135.10, 131.65, 127.80, 127.41, 125.03, 116.58, 112.53, 48.64. ESI-LRMS: $[M+H]^+$=268 m/z. ESI-HRMS: calc. for $C_{15}H_{13}N_3O_2$: $[M+H]^+$=268.1081 m/z, found: $[M+H]^+$=268.1080 m/z.

N-(2-(1H-Indol-3-yl)ethyl)methanesulfonamide (28)

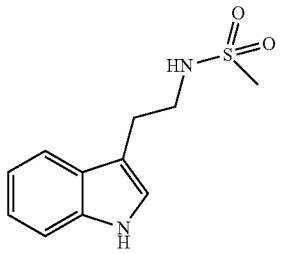

A round bottom flask charged with tryptamine (2.0 g, 12.5 mmol) in DCM (20 mL) was added $Et_3N$ (3.5 mL, 25 mmol) under an atmosphere of Ar and cooled to 0° C. The solution was then added mesyl chloride (1.5 mL, 18.7 mmol) and the resulting reaction mixture was stir to RT for 2 h. The reaction was quenched with water (20 mL) and extracted with DCM (3×20 mL). The combined organic extracts were washed with brine (30 mL), dried over $Na_2SO_4$ and concentrated in vacuo. The desired product was purified via automated column chromatography method 2 (2.1 g, 70%) and isolated as a brown oil. $^1$H NMR (400 MHz, MeOD) δ 7.55 (d, J=7.6 Hz, 1H), 7.33 (d, J=8.0 Hz, 1H), 7.08 (m, 2H), 7.01 (td, J=8.0, 0.8 Hz, 1H), 3.35 (t, J=7.2 Hz, 2H), 2.99 (t, J=7.2 Hz, 2H), 2.76 (s, 3H). $^{13}$C NMR (100 MHz, MeOD) δ 138.28, 128.77, 123.91, 122.54, 119.85, 119.34, 112.93, 112.43, 45.09, 40.02, 27.60.

Methyl 4-((3-(2-(methylsulfonamido)ethyl)-1H-indol-1-yl)methyl)benzoate (29)

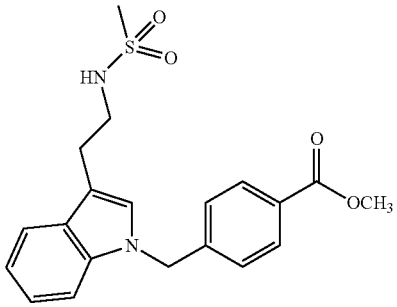

The title compound was prepared from N-(2-(1H-indol-3-yl)ethyl)methanesulfonamide 28 (300 mg, 1.26 mmol) according to General Procedure A (substituting KO$^t$Bu for NaH) and purified using automated column chromatography method 2. The product was isolated as a brown waxy solid (0.399 g, 82%). $^1$H NMR (400 MHz, $CDCl_3$) δ 8.20 (br s, 1 H), 8.01 (d, J=8.0 Hz, 2 H), 7.42 (m, 3 H), 7.33 (d, J=8.4 Hz, 1 H), 7.17 (t, J=7.6 Hz, 1 H), 7.08 (t, J=7.2 Hz, 1 H), 6.95 (d, J=1.6 Hz, 1 H), 4.45 (s, 2 H), 3.92 (s, 3 H), 3.49 (t, J=7.6 Hz, 2 H), 2.96 (t, J=7.6 Hz, 2 H), 2.74 (s, 3 H). $^{13}$C NMR (100 MHz, $CDCl_3$) δ 166.69, 141.53, 136.17, 129.95, 129.80, 126.96, 122.14, 122.13, 119.49, 118.40, 112.09, 111.27, 52.13, 51.23, 48.35, 38.90, 24.82. ESI-LRMS: $[M+H]^+$=386 m/z.

N-Hydroxy-4-((3-(2-(methylsulfonamido)ethyl)-1H-indol-1-yl)methyl)benzamide (30)

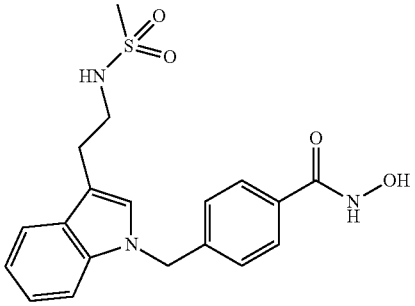

The title compound was synthesized from methyl 4-((3-(2-(methylsulfonamido)ethyl)-1H-indol-1-yl)methyl)benzoate 29 (155 mg, 0.401 mmol) according to General Procedure D (prep. HPLC method 2) and isolated as a beige solid (55 mg, 35%). $^1$H NMR (400 MHz, DMSO-$d_6$) δ 11.22 (br s, 1H), 10.82 (s, 1H), 7.87 (d, J=8.4 Hz, 2H), 7.48 (d, J=8.4 Hz, 2H), 7.31 (d, J=8.0 Hz, 1H), 7.11 (d, J=2.4 Hz, 1H), 7.05 (td, J=7.6, 0.8 Hz, 1H), 6.94 (td, J=7.6, 0.8 Hz, 1H), 4.48 (s, 2H), 3.35 (m, 2H), 2.97 (s, 3H), 2.84 (m, 2H). $^{13}$C NMR (100 MHz, DMSO-$d_6$) δ 164.00, 140.73, 136.15, 131.99, 128.01, 127.09, 126.84, 122.98, 121.00, 118.32, 118.07, 111.42, 110.70, 50.53, 48.42, 38.02, 24.48. LR-ESI MS (m/z): 388 $[M+H]^+$. ESI-HRMS: calc. for $C_{19}H_{21}N_3O_4S$: $[M+H]^+$=388.1326 m/z, found: $[M+H]^+$=388.1319 m/z.

Methyl 4-((2-methyl-1H-benzo[d]imidazol-1-yl)methyl)benzoate (31)

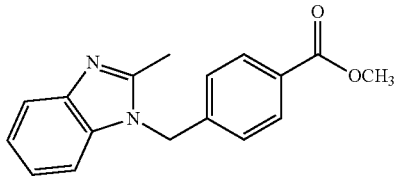

The title compound was prepared from 2-methyl-1H-benzo[d]imidazole (264 mg, 2.0 mmol) according to General Procedure C and purified using automated column chromatography method 2. The product was isolated as an off-white waxy solid (298 mg, 53%). $^1$H NMR (400 MHz, $CDCl_3$) δ 7.95 (d, J=8.4 Hz, 2H), 7.72 (d, J=8.0 Hz, 1H), 7.21 (m, 3H), 7.08 (d, J=8.4 Hz, 2H), 5.32 (s, 2H), 3.87 (s, 3H), 2.53 (s, 2H). $^{13}$C NMR (100 MHz, $CDCl_3$) δ 166.32, 151.60, 142.56, 140.77, 135.18, 130.18, 129.78, 126.04, 122.33, 122.08, 119.14, 109.06, 71.82, 52.06, 46.69, 13.81. ESI-LRMS: $[M+H]^+$=281 m/z.

N-hydroxy-4-((2-methyl-1H-benzo[d]imidazol-1-yl)methyl)benzamide (32)

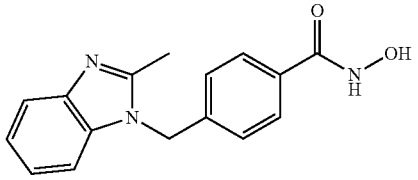

The title compound was synthesized from methyl 4-((2-methyl-1H-benzo[d]imidazol-1-yl)methyl)benzoate 31 (157 mg, 0.560) according to General Procedure D (prep. HPLC method 2) and isolated as an off-white solid (55 mg, 35%). $^1$H NMR (400 MHz, DMSO-$d_6$) δ 11.27 (br s, 1H), 7.74 (m, 3H), 7.69 (d, J=8.4 Hz, 1H), 7.44 (m, 2H), 7.34 (d, J=8.4 Hz, 2H), 5.72 (s, 2H), 2.80 (s, 3H). $^{13}$C NMR (100 MHz, DMSO-$d_6$) δ 164.05, 152.38, 138.48, 133.78, 133.10, 132.92, 127.90, 127.55, 125.24, 125.01, 115.64, 112.54, 47.33, 12.72. LR-ESI MS (m/z): 282 $[M+H]^+$. ESI-HRMS: calc. for $C_{16}H_{15}N_3O_2$: $[M+H]^+$=282.1237 m/z, found: $[M+H]^+$=282.1244 m/z.

tert-Butyl (3-(1H-benzo[d]imidazol-2-yl)propyl) carbamate (33)

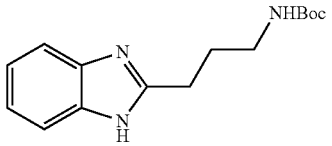

To a round bottom flask charged with 4-((tert-butoxycarbonyl)amino)butanoic acid (0.5 g, 2.46 mmol) in DCM (10 mL) was added $Et_3N$ (1.03 mL, 7.36 mmol), EDCI (706 mg, 2.46 mmol), DMAP (30 mg, 0.246 mmol) and allowed to stir overnight at RT. The reaction was quenched with water (10 mL) and extracted with DCM (2×10 mL). Combined organics washed with 10% citric acid (10 mL), brine (10 mL), dried over $Na_2SO_4$ and concentrated in vacuo. The crude material was dissolved in AcOH (7 mL) and stirred at 65° C. for 1 h. The mixture was diluted with saturated bicarbonate (15 mL) and extracted with DCM (2×15 mL), and again worked up in the above manner. The title compound was obtained as a white solid (433 mg, 64%) and used without further purification. $^1$H NMR (400 MHz, $CDCl_3$) δ 7.57 (m, 2H), 7.20 (m, 2H), (4.98 (s, 2H), 3.24 (m, 2H), 2.95 (m, 2H), 1.92 (m, 2H), 1.47 (s, 9H). ESI-LRMS: $[M+H]^+$=276 m/z.

Methyl 4-((2-(3-aminopropyl)-1H-benzo[d]imidazol-1-yl)methyl)benzoate (34)

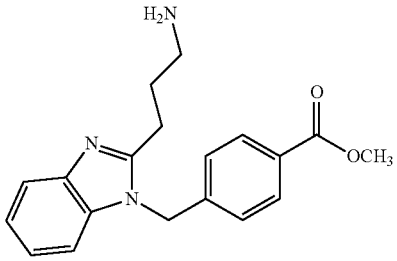

The title compound was prepared from tert-Butyl (3-(1H-benzo[d]imidazol-2-yl)propyl)carbamate 33 (433 mg, 1.57 mmol) using General Procedure C. The crude material was taken up into acetone (7 mL), added conc. HCl (3 equiv) and allowed to stir at 50° C. for 4 h. The reaction was quenched with saturated bicarbonate and worked up in the usual manner, affording the title compound as a viscous brown oil (458 (mg, 90%) used without further purification. $^1$H NMR (400 MHz, MeOD) δ 7.95 (m, 3H), 7.63 (d, J=7.6 Hz, 1H), 7.44 (d, J=8.0 Hz, 1H), 7.33 (m, 1H), 7.23 (m, 2H), 7.18 (m, 2H), 5.58 (s, 2H), 3.86 (m, 3H), 2.93 (t, J=7.6 Hz, 2H), 2.06 (t, J=7.6 Hz, 2H), 1.98 (m, 2H). ESI-LRMS: $[M+H]^+$=324 m/z.

Methyl 4-((2-(3-acetamidopropyl)-1H-benzo[d]imidazol-1-yl)methyl)benzoate (35)

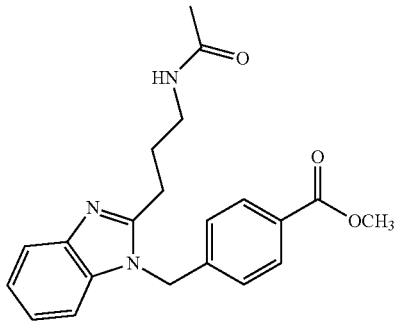

To a round bottom flask charged with methyl 4-((2-(3-aminopropyl)-1H-benzo[d]imidazol-1-yl)methyl)benzoate 34 (135 mg, 0.417 mmol) in DCM (5 mL) was added $Et_3N$ (0.076 mL, 0.543 mmol) and catalytic DMAP (5 mg, 0.042 mmol). The reaction was cooled to 0° C. and then $Ac_2O$ (0.051 mL, 0.543 mmol) was added dropwise. The resulting solution was allowed to warm to RT and stirred for 18 h after which the reaction was quenched with $H_2O$ (10 mL) and extracted with chloroform (3×10 mL). Combined extracts were washed with brine (20 mL), dried over $Na_2SO_4$ and concentrated in vacuo. The crude product was purified using automated column chromatography method 2 and isolated as a white, waxy solid (53 mg, 35%). $^1$H NMR (400 MHz, CDCl3) δ 7.96 (d, J=8.0 Hz, 2H), 7.73 (d, J=7.6 Hz, 1H), 7.24 (m, 3H), 7.07 (d, J=8.0 Hz, 2H), 6.73 (br s, 1H), 5.38 (s, 2H), 3.88 (s, 3H), 3.33 (m, 2H), 2.89 (t, J=7.2H, 2H), 2.05 (m, 2H), 1.86 (s, 3H). $^{13}$C NMR (100 MHz, $CDCl_3$) δ 170.44, 166.32, 154.48, 141.76, 140.60, 134.98, 130.26, 129.91, 126.00122.81, 122.49, 118.89, 109.42, 52.12, 46.60, 38.91, 26.42, 24.92, 22.97. ESI-LRMS: $[M+H]^+$=366 m/z.

4-((2-(3-Acetamidopropyl)-1H-benzo[d]imidazol-1-yl)methyl)-N-hydroxybenzamide.TFA (36)

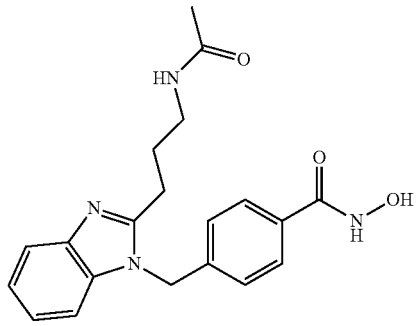

The title compound was synthesized from methyl 4-((2-(3-acetamidopropyl)-1H-benzo[d]imidazol-1-yl)methyl) benzoate 35 (53 mg, 0.145 mmol) according to General Procedure D (prep. HPLC method 2) and isolated as a white solid (36 mg, 52%). $^1$H NMR (400 MHz, DMSO-$d_6$) δ 8.01 (m, 1H), 7.78 (m, 4H), 7.52 (m, 2H), 7.33 (d, J=8.0 Hz, 2H), 5.78 (s, 2H), 3.18 (m, 4H), 1.92 (m, 2H), 1.78 (s, 3H). $^{13}$C NMR (100 MHz, DMSO-$d_6$) δ 169.12, 163.16, 157.65, 154.11, 137.32, 132.19, 131.80, 127.09, 126.62, 125.30, 124.98, 114.39, 112.34, 46.74, 37.29, 26.03, 22.62, 22.19. ESI-LRMS: $[M+H]^+$=367 m/z. ESI-HRMS: calc. for $C_{20}H_{22}N_4O_3$: $[M+H]^+$=367.1765 m/z, found: $[M+H]^+$=367.1757 m/z.

Methyl 4-((2-(2-(dimethylamino)ethyl)-1H-benzo[d]imidazol-1-yl)methyl)benzoate (37)

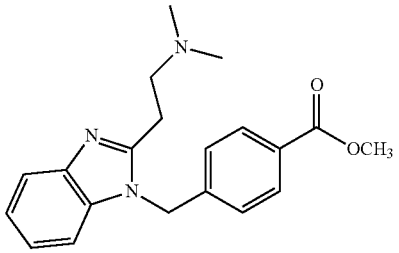

tert-Butyl 2-(1H-benzo[d]imidazol-2-yl)ethylcarbamate (390 mg, 1.70 mmol) was subjected to general procedure C to produce the ester intermediate methyl 4-((2-(2-(tert-butoxycarbonylamino)ethyl)-1H-benzo[d]imidazol-1-yl)methyl)benzoate. The crude material was dissolved in acetone (2 mL/mmol ester), conc. HCl (3 mol equiv) was added and then the reaction was stirred for 16 h. The precipitate was filtered, washed with acetone, dried, and used without further purification. The dihydrochloride intermediate (131 mg, 0.343 mmol) was dissolved in MeOH (3 mL) and cooled to 0° C. AcOH (0.100 μM) was added followed by $NaCNBH_3$ (43 mg, 0.686 mmol) under an atmosphere of Ar. Lastly, a solution of $CH_2O$ (0.1 mL, 37% wt soln) in MeOH (1 mL) was added dropwise. The resulting reaction mixture was allowed to stir 4.5 h to RT. The reaction was quenched with 1N HCl (10 mL) and extracted with EtOAc (3×10 mL). The aqueous layer was made basic with 2 N NaOH and again extracted with EtOAc (3×10 mL). The basic extraction was washed with brine (20 mL), dried over $Na_2SO_4$ and concentrated in vacuo. Material was purified via automated column chromatography method 2 to yield a white waxy solid (88 mg, 76%). $^1$H NMR (400 MHz, $CDCl_3$) δ 7.98 (d, J=8.4 Hz, 2H), 7.76 (J=8.0 Hz, 1H), 7.23 (m, 3H), 7.11 (d, J=8.4 Hz, 2H), 5.42 (s, 2H), 3.89 (s, 3H), 3.00 (t, J=7.6 Hz, 2H), 2.83 (t, J=7.6 Hz, 2H), 2.26 (s, 6H). $^{13}$C NMR (100 MHz, $CDCl_3$) δ 166.44, 153.45, 142.61, 140.99, 135.17, 130.26, 129.86, 126.10, 122.58, 122.25, 119.42, 109.27, 57.13, 52.15, 46.68, 45.29, 26.07. ESI-LRMS: $[M+H]^+$=338 m/z, $[M+Na]^+$=360 m/z.

4-((2-(2-(Dimethylamino)ethyl)-1H-benzo[d]imidazol-1-yl)methyl)-N-hydroxybenzamide (38)

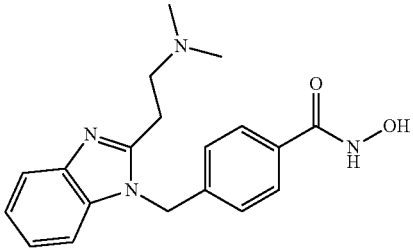

The title compound was synthesized from methyl 4-(2-(2-(dimethylamino)ethyl)-1H-benzo[d]imidazol-1-yl)methyl)benzoate 37 (88 mg, 0.261 mmol) according to General Procedure D (prep. HPLC method 2) and isolated as a white solid (53 mg, 60%). $^1$H NMR (400 MHz, DMSO-$d_6$) δ 7.68 (d, J=8.4 Hz, 2H), 7.58 (m, 1H), 7.42 (m, 1H), 7.16 (m, 4H), 5.55 (s, 2H), 2.96 (t, J=7.6 Hz, 2H), 2.64 (t, J=7.6 Hz, 2H), 2.13 (s, 6H). $^{13}$C NMR (100 MHz, DMSO-$d_6$) δ 163.65, 153.91, 142.34, 139.87, 135.25, 132.50, 127.17, 126.34, 121.77, 121.42, 118.47, 110.10, 56.75, 45.80, 44.98, 25.15. ESI-LRMS: $[M+H]^+$=339 m/z. ESI-HRMS: calc. for $C_{19}H_{22}N_4O_2$: $[M+H]^+$=339.1816 m/z, found: $[M+H]^+$=339.1811 m/z.

N-Hydroxy-4-((2-isopropyl-1H-benzo[d]imidazol-1-yl)methyl)benzamide (39)

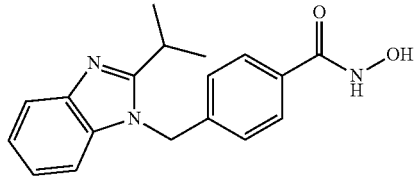

The title compound was synthesized by subjecting 2-isopropyl-1H-benzo[d]imidazole (209 mg, 1.30 mmol) to General Procedure C (automated column chromatography method 2) followed by General Procedure D (prep. HPLC method 2). The desired product was isolated as a white solid (23 mg, 25%). $^1$H NMR (400 MHz, DMSO-$d_6$) δ 11.95 (s, 1H), 9.01 (s, 1H), 7.68 (d, J=8.4 Hz, 2H), 7.60 (m, 1H), 7.40 (m, 1H), 7.16 (m, 2H), 7.10 (d, J=8.4 Hz, 2H), 5.57 (s, 2H), 3.25 (quint, J=6.8 Hz, 1H), 1.26 (s, 3H), 1.24 (s, 3H). $^{13}$C NMR (100 MHz, DMSO-$d_6$) δ 163.84, 159.85, 142.26, 140.43, 135.12, 131.98, 127.32, 126.20, 121.77, 121.44, 118.63, 110.20, 45.54, 25.71, 21.75 ESI-LRMS: $[M+H]^+$=310 m/z. ESI-HRMS: calc. for $C_{18}H_{19}N_3O_2$: $[M+H]^+$=310.1550 m/z, found: $[M+H]^+$=310.1563 m/z.

Two examples of present HDACIs having a monocyclic Cap group are prepared as follows (see also General Synthetic Schemes B and C):

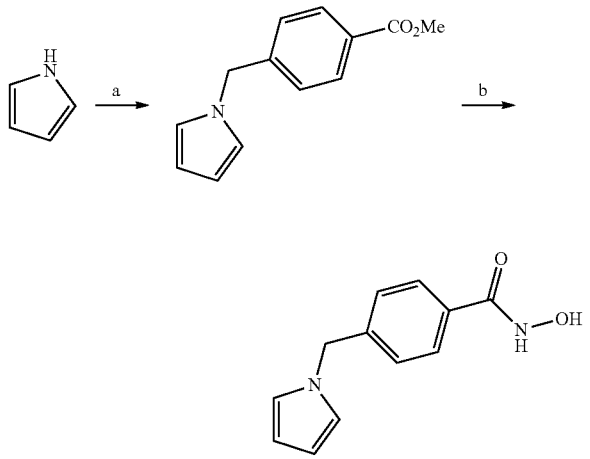

Reagents and conditions:

a) methyl 4-(bromomethyl)benzoate, KO$^t$Bu, DMF, 80° C., 2 h;

b) $NH_2OH$•HCl, NaOMe, MeOH, 0° C. to rt, 16 h.

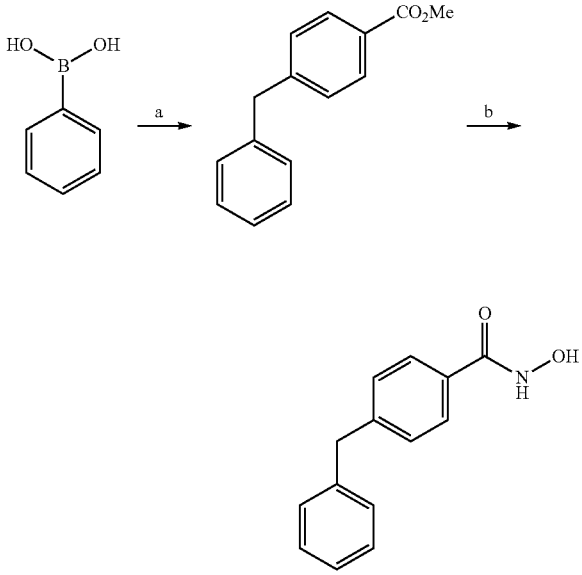

Reagents and conditions:
a) Tetrakis(triphenylphosphine)palladium(0), methyl 4-(bromomethyl)benzoate, $Na_2CO_3$, DME or diglyme, $H_2O$, 100° C., 4 h;
b) $NH_2OH{\bullet}HCl$, NaOMe, MeOH, 0° C. to rt, 16 h.

Examples of monocyclic Cap groups include, but are not limited to:

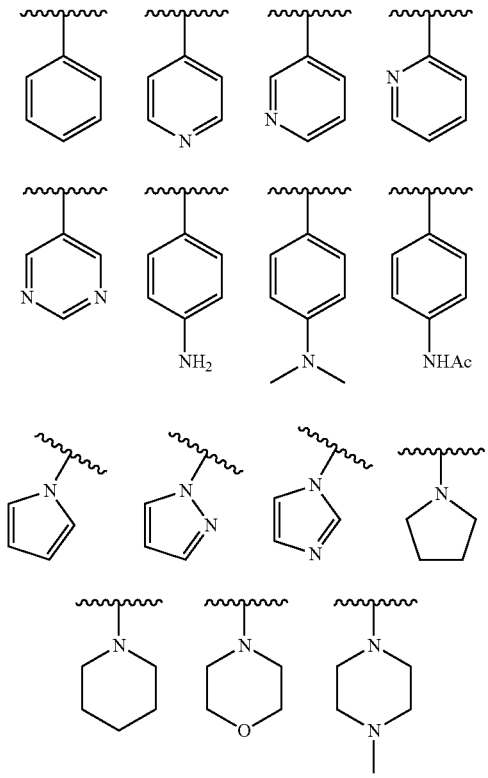

HDACIs having a five-membered or six-membered monocylic Cap group:

Methyl 4-((1H-pyrrol-1-yl)methyl)benzoate (40)

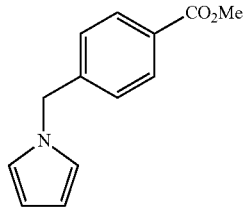

The title compound was prepared from 1H-pyrrole (0.150 g, 2.24 mmol) according to General Procedure A (substituting KO$^t$Bu for NaH) and purified using automated column chromatography method 1. The product was isolated as a clear viscous oil (0.432 g, 90%). $^1$H NMR (400 MHz, $CDCl_3$): δ 8.01 (d, J=8.3 Hz, 2H), 7.17 (d, J=8.3 Hz, 2H), 6.72 (t, J=2.0 Hz, 2H), 6.24 (t, J=2.1 Hz, 2H), 5.15 (s, 2H), 3.93 (s, 3H). $^{13}$C NMR (100 MHz, $CDCl_3$): δ 166.7, 143.4, 130.0, 129.5, 126.7, 121.2, 108.9, 53.0, 52.1.

4-((1H-Pyrrol-1-yl)methyl)-N-hydroxybenzamide (41)

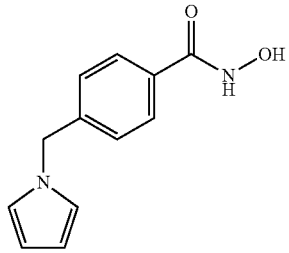

The title compound was synthesized from methyl 4-((1H-pyrrol-1-yl)methyl)benzoate 40 (0.400 g, 1.86 mmol) according to General Procedure B (prep. HPLC method 1) and isolated as a white solid (0.225 g, 56%). $^1$H NMR (400 MHz, MeOD): δ 7.70 (d, J=8.3 Hz, 2H), 7.20 (d, J=8.3 Hz, 2H), 6.73 (t, J=2.0 Hz, 2H), 6.11 (t, J=2.1 Hz, 2H), 5.17 (s, 2H). $^{13}$C NMR (100 MHz, MeOD): δ 166.4, 143.0, 131.2, 127.0, 126.6, 120.7, 108.0, 52.0. ESI-HRMS: calc. for $C_{12}H_{12}N_2O_2$: $[M+H]^+$=217.0972 m/z, found: $[M+H]^+$= 217.0975 m/z.

Methyl 4-((1H-pyrazol-1-yl)methyl)benzoate (42)

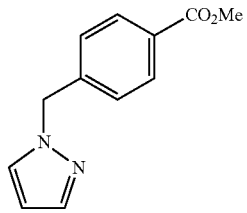

The title compound was prepared from 1H-pyrazole (0.150 g, 2.20 mmol) according to General Procedure A (substituting KO$^t$Bu for NaH) and purified using automated column chromatography method 1. The product was isolated as a viscous yellow oil (0.387 g, 81%). $^1$H NMR (400 MHz, $CDCl_3$): δ 7.99 (d, J=8.2 Hz, 2H), 7.56 (s, 1H), 7.41 (d, J=2.0 Hz, 1H), 7.20 (d, J=8.1 Hz, 2H), 6.30 (d, J=1.9 Hz, 1H), 5.36 (s, 2H), 3.88 (s, 3H). $^{13}$C NMR (100 MHz, $CDCl_3$): δ 166.2, 141.5, 139.5, 129.7, 129.4, 129.1, 126.9, 105.9, 55.0, 51.7. ESI-HRMS: calc. for $C_{12}H_{12}N_2O_2$: $[M+H]^+$=217.0972 m/z, found: $[M+H]^+$=217.0969 m/z.

4-((1H-Pyrazol-1-yl)methyl)-N-hydroxybenzamide (43)

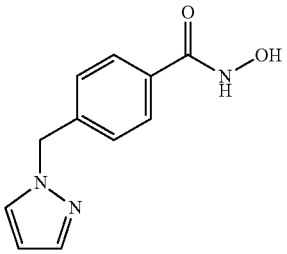

The title compound was synthesized from methyl 44(1H-pyrazol-1-yl)methyl)benzoate 42 (0.387 g, 1.79 mmol) according to General Procedure B (prep. HPLC method 1) and isolated as a white solid (0.251 g, 65%). $^1$H NMR (400 MHz, MeOD): δ 7.74 (m, 3H), 7.55 (d, J=1.5 Hz, 1H), 7.27 (d, J=8.4 Hz, 2H), 6.37 (t, J=2.1 Hz, 1H), 5.43 (s, 2H). $^{13}$C NMR (100 MHz, MeOD): δ 166.3, 140.9, 139.3, 131.7, 130.5, 127.1, 127.0, 105.7, 54.3. ESI-HRMS: calc. for $C_{11}H_{11}N_3O_2$: $[M+H]^+$=218.0924 m/z, found: $[M+H]^+$=218.0917 m/z.

Methyl 4-(pyridin-4-ylmethyl)benzoate (44)

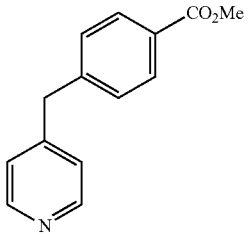

The title compound was prepared from pyridin-4-ylboronic acid (0.123 g, 1.00 mmol) according to General Procedure E and purified using automated column chromatography method 2 (20 mg, 9%). $^1$H NMR (400 MHz, MeOD): δ 8.59 (d, J=6.6 Hz, 2H), 7.86 (d, J=8.3 Hz, 2H), 7.78 (d, J=6.6 Hz, 2H), 7.28 (d, J=8.3 Hz, 2H), 4.26 (s, 2H), 3.74 (s, 3H). $^{13}$C NMR (100 MHz, $CDCl_3$): δ 166.7, 162.3, 142.4, 141.2, 129.9, 129.3, 129.1, 127.2, 51.3, 40.8. ESI-LRMS: $[M+H]^+$=228 m/z.

N-Hydroxy-4-(pyridin-4-ylmethyl)benzamide (45)

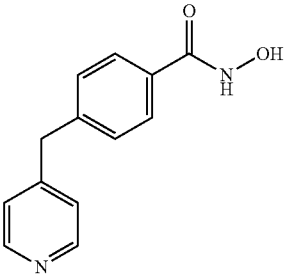

The title compound was synthesized from methyl 4-(pyridin-4-ylmethyl)benzoate 44 (0.020 g, 0.09 mmol) according to General Procedure B (prep. HPLC method 2) and isolated as a white solid (5 mg, 25%). $^1$H NMR (400 MHz, MeOD): δ 8.74 (d, J=6.4 Hz, 2H), 7.93 (d, J=6.3 Hz, 2H), 7.78 (d, J=8.2 Hz, 2H), 7.43 (d, J=8.1 Hz, 2H), 4.41 (s, 2H). $^{13}$C NMR (100 MHz, MeOD): δ 166.1, 162.4, 141.4, 140.8, 131.3, 129.3, 127.5, 127.1, 40.7. ESI-HRMS: calc. for $C_{13}H_{12}N_2O_2$: $[M+H]^+$=229.0972 m/z, found: $[M+H]^+$=229.0966 m/z.

Methyl 4-(4-(dimethylamino)benzyl)benzoate (46)

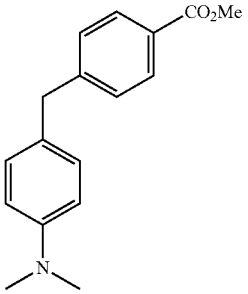

The title compound was prepared from 4-(dimethylamino)phenylboronic acid (0.165 g, 1.00 mmol) according to General Procedure E and purified using automated column chromatography method 2. The product was isolated as an orange oil (0.211 g, 78%). $^1$H NMR (400 MHz, MeOD): δ 7.93 (d, J=8.4 Hz, 2H), 7.59 (d, J=8.7 Hz, 2H), 7.45 (d, J=8.7 Hz, 2H), 7.33 (d, J=8.4 Hz, 2H), 4.10 (s, 2H), 3.87 (s, 3H), 3.28 (s, 6H). $^{13}$C NMR (100 MHz, $CDCl_3$): δ 166.9, 146.0, 142.8, 141.3, 130.6, 129.5, 128.7, 128.1, 120.3, 51.2, 45.6, 40.5. ESI-LRMS: $[M+H]^+$=270 m/z.

4-(4-(Dimethylamino)benzyl)-N-hydroxybenzamide (47)

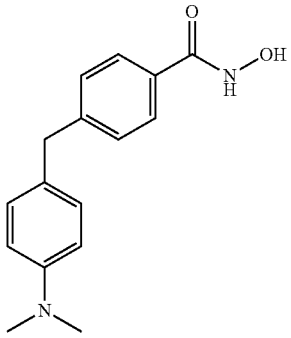

The title compound was synthesized from methyl 4-(4-(dimethylamino)benzyl)benzoate 46 (0.211 g, 0.78 mmol) according to General Procedure B (prep. HPLC method 2) and isolated as a white solid (0.140 g, 66%). $^1$H NMR (400 MHz, MeOD): δ 7.69 (d, J=8.2 Hz, 2H), 7.53 (d, J=8.6 Hz, 2H), 7.42 (d, J=8.56, 2H), 7.31 (d, J=8.1 Hz, 2H), 4.09 (s, 2H), 3.25 (s, 6H). $^{13}$C NMR (100 MHz, MeOD): δ 166.6, 144.5, 142.3, 141.7, 130.5, 130.2, 128.8, 127.1, 119.8, 45.3, 40.4. ESI-HRMS: calc. for $C_{16}H_{18}N_2O_2$: $[M+H]^+$=271.1441 m/z, found: $[M+H]^+$=271.1448 m/z.

Methyl 4-(3-(dimethylamino)benzyl)benzoate (48)

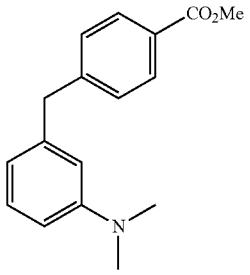

The title compound was prepared from 3-(dimethylamino)phenylboronic acid (0.165 g, 1.00 mmol) according to General Procedure E and purified using automated column chromatography method 2. The product was isolated as a clear oil (0.254 g, 94%). $^1$H NMR (400 MHz, $CDCl_3$): δ 7.99 (d, J=8.1 Hz, 2H), 7.30 (m, 6H), 4.08 (s, 2H), 3.91 (s, 3H), 3.15 (s, 6H). $^{13}$C NMR (100 MHz, $CDCl_3$): δ 166.9, 144.9, 144.5, 143.1, 130.6, 130.0, 128.9, 128.8, 128.6, 119.9, 117.5, 52.1, 45.6, 41.6. ESI-LRMS: $[M+H]^+$=270 m/z.

4-(3-(Dimethylamino)benzyl)-N-hydroxybenzamide (49)

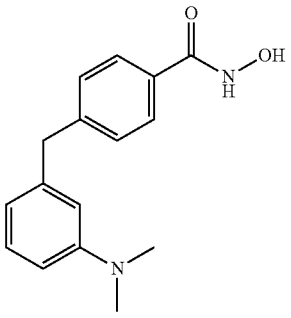

The title compound was synthesized from methyl 4-(3-(dimethylamino)benzyl)benzoate 48 (0.254 g, 0.94 mmol) according to General Procedure B (prep. HPLC method 2) and isolated as a white solid (0.117 g, 46%). $^1$H NMR (400 MHZ, $CDCl_3$): δ 7.70 (d, J=8.2 Hz, 2H), 7.50 (m, 3H), 7.35 (m, 3H), 4.12 (s, 2H), 3.27 (s, 6H). $^{13}$C NMR (100 MHZ, $CDCl_3$): δ 166.6, 144.3, 143.7, 143.6, 130.4, 130.2, 129.7, 128.8, 127.1, 120.2, 117.5, 45.4, 40.7. ESI-HRMS: calc. for $C_{16}H_{18}N_2O_2$: $[M+H]^+$=271.1450 m/z, found: $[M+H]^+$=271.1450 m/z.

An example of a present HDACI having an acyclic Cap group is prepared as follows (see also General Synthetic Scheme D):

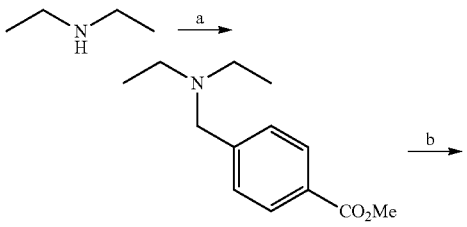

-continued

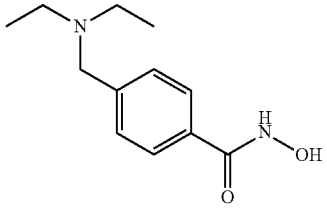

Reagents and conditions:
a) methyl 4-(bromomethyl)benzoate, KO$^t$Bu, DMF, 80° C., 2 h;
b) $NH_2OH$•HCl, NaOMe, MeOH, 0° C. to rt, 16 h.

Examples of acyclic Cap groups include, but are not limited to:

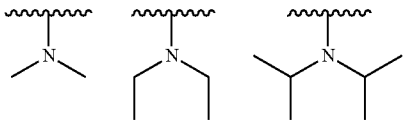

HDACI compounds having an acyclic Cap group:

Methyl 4-((diethylamino)methyl)benzoate (50)

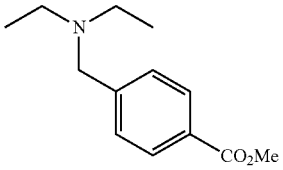

The title compound was prepared from diethylamine (0.350 g, 4.79 mmol) according to General Procedure A (substituting KO$^t$Bu for NaH). The pH was adjusted to 10 with 2 N NaOH prior to extraction with EtOAc. The product was isolated as a yellow oil and did not require further purification (0.790 g, 75%). $^1$H NMR (400 MHz, MeOD): δ 8.14 (d, J=8.2 Hz, 2H), 7.66 (d, J=8.2 Hz, 2H), 4.44 (s, 2H), 3.95 (s, 3H), 3.25 (m, 4H), 1.37 (t, J=7.3 Hz, 6H). $^{13}$C NMR (100 MHz, DMSO-$d_6$): δ 166.2, 135.9, 131.8, 130.9, 130.0, 54.8, 52.8, 46.6, 8.8. ESI-HRMS: calc. for $C_{13}H_{19}NO_2$: $[M+H]^+$=222.1489 m/z, found: $[M+H]^+$=222.1485 m/z.

4-((Diethylamino)methyl)-N-hydroxybenzamide (51)

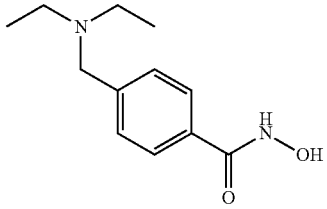

The title compound was synthesized from methyl 4-((diethylamino)methyl)benzoate 50 (0.518 g, 2.34 mmol) according to General Procedure B (prep. HPLC method 2) and isolated as a viscous, yellow oil (0.448 g, 56%). $^1$H NMR (400 MHz, MeOD): δ 7.72 (d, J=8.2 Hz, 2H), 7.42 (d, J=8.1 Hz, 2H), 3.65 (s, 2H), 2.55 (q, J=7.2 Hz, 4H), 1.08 (t, J=5.0 Hz, 6H). $^{13}$C NMR (100 MHz, MeOD): δ 166.3, 139.5, 131.9, 129.7, 127.0, 56.1, 46.4, 9.3. ESI-HRMS: calc. for $C_{12}H_{18}N_2O_2$: $[M+H]^+$=223.1441 m/z, found: $[M+H]^+$=223.1441 m/z.

Methyl 4-((diisopropylamino)methyl)benzoate (52)

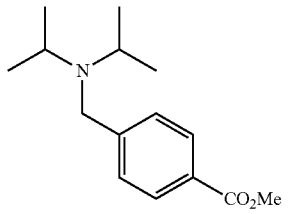

The title compound was prepared from diisopropylamine (0.500 g, 4.94 mmol) according to General Procedure A (substituting KO$^t$Bu for NaH). The pH was adjusted to 10 with 2 N NaOH prior to extraction with EtOAc. The product was isolated as a yellow oil and did not require further purification (1.10 g, 89%). $^1$H NMR (400 MHz, MeOD): δ 8.10 (d, J=8.4 Hz, 2H), 7.71 (d, J=8.4 Hz, 2H), 4.51 (s, 2H), 3.93 (s, 3H), 3.85 (m, 2H), 1.46 (dd, J=6.1 Hz, J=12.5 Hz, 12H). $^{13}$C NMR (100 MHz, MeOD): δ 165.9, 135.9, 130.6, 130.1, 129.4, 54.8, 51.1, 49.4, 17.2, 16.3. ESI-HRMS: calc. for $C_{15}H_{23}NO_2$: $[M+H]^+$=250.1802 m/z, found: $[M+H]^+$=250.1800 m/z.

4-((Diisopropylamino)methyl)-N-hydroxybenzamide (53)

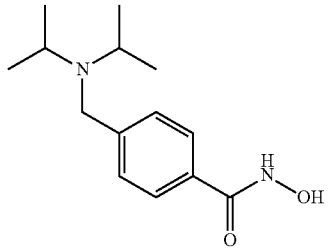

The title compound was synthesized from methyl 4-((diisopropylamino)methyl)benzoate 52 (0.750 g, 3.0 mmol) according to General Procedure B (prep. HPLC method 2) and isolated as a viscous, light-yellow oil (0.324 g, 42%). $^1$H NMR (400 MHz, MeOD): δ 7.84 (d, J=8.2 Hz, 2H), 7.67 (d, J=8.2 Hz, 2H), 4.48 (s, 2H), 3.84 (m, 2H), 1.47 (br, 12H). $^{13}$C NMR (100 MHz, MeOD): δ 165.6, 134.7, 133.2, 130.5, 127.5, 55.1, 49.7, 17.5, 16.8. ESI-HRMS: calc. for $C_{14}H_{22}N_2O_2$: $[M+H]^+$=251.1754 m/z, found: $[M+H]^+$=251.1744 m/z.

Methyl 4-((diphenylamino)methyl)benzoate (54)

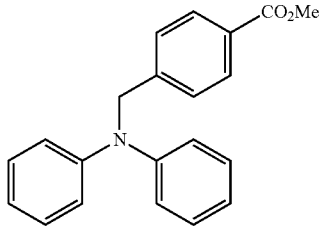

NaH (0.220 g, 5.54 mmol) was dissolved in anhydrous DMF (2 mL) under argon and cooled to 0° C. To it was added diphenylamine (0.0.750 g, 4.43 mmol) dissolved in anhydrous DMF (2 mL). The reaction was stirred for 15 min at 0° C. followed by the addition of methyl 4-(bromomethyl) benzoate (1.02 g, 4.43 mmol) in anhydrous DMF (2 mL). The reaction was stirred for 2 h at 60° C. and then quenched by the addition of $H_2O$ (20 mL). The organic products were extracted with EtOAc (3×30 mL), washed with $H_2O$ (2×30 mL), brine (15 mL), dried with $Na_2SO_4$, filtered and concentrated in vacuo. The title compound was purified using automated column chromatography method 1 (0.746 g, 53%). $^1$H NMR (400 MHz, $CDCl_3$): δ 8.00 (d, J=8.2 Hz, 2H), 7.45 (d, J=7.7 Hz, 2H), 7.27 (m, 4H), 7.07 (d, J=7.9 Hz, 4H), 6.98 (t, J=7.3 Hz, 2H), 5.06 (s, 2H), 3.92 (s, 3H). $^{13}$C NMR (100 MHz, $CDCl_3$): δ 166.9, 147.8, 144.8, 130.0, 129.4, 128.9, 126.5, 121.7, 120.7, 56.3, 52.0. ESI-LRMS: $[M+H]^+$=318 m/z.

4-((Diphenylamino)methyl)-N-hydroxybenzamide (55)

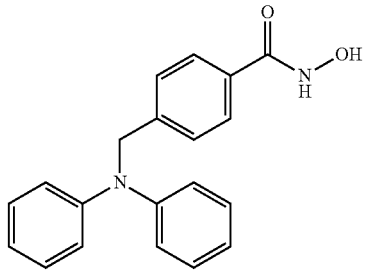

The title compound was synthesized from methyl 4-((diphenylamino)methyl)benzoate 54 (0.200 g, 0.33 mmol) according to General Procedure B (prep. HPLC method 2) and isolated as a white solid (27 mg, 13%). $^1$H NMR (400 MHz, MeOD): δ 7.69 (d, J=8.0 Hz, 2H), 7.47 (d, J=8.0 Hz, 2H), 7.23 (t, J=7.6 Hz, 4H), 7.05 (d, J=8.0 Hz, 4H), 6.93 (t, J=7.5 Hz, 2H), 5.07 (s, 2H). $^{13}$C NMR (100 MHz, DMSO-$d_6$): δ 164.5, 147.8, 143.0, 131.8, 129.8, 127.5, 126.9, 121.7, 120.7, 55.5. ESI-HRMS: calc. for $C_{20}H_{18}N_2O_2$: $[M+H]^+$=319.1441 m/z, found: $[M+H]^+$=319.1447 m/z.

Methyl 4-(pyrrolidin-1-ylmethyl)benzoate (56)

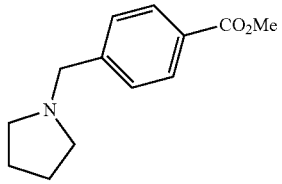

Pyrrolidine (0.12 mL, 1.52 mmol), methyl 4-formylbenzoate (0.250 g, 1.52 mmol), $NaBH(OAc)_3$ (0.52 g, 2.4 mmol) and 5 Å molecular sieves were dissolved in 1,2-dichloroethane (5 mL) under Ar atmosphere and stirred for 24 h at RT. Then, the reaction was diluted with 2 N NaOH (30 mL) and extracted with EtOAc (3×20 mL). The combined organic fractions were washed with brine (15 mL), dried over $Na_2SO_4$, filtered and concentrated in vacuo. The crude product was purified via automated column chromatography (50-100% EtOAc/hexane, 25 g cartridge) to yield the title compound as a clear oil (0.166 g, 50%). $^1$H NMR (400 MHz, $CDCl_3$): δ 8.00 (d, J=8.0 Hz, 2H), 7.43 (d, J=8.0 Hz, 2H), 3.92 (s, 3H), 3.69 (s, 2H), 2.54 (br, 4H), 1.81 (t, J=3.2 Hz, 4H).

N-Hydroxy-4-(pyrrolidin-1-ylmethyl)benzamide.TFA (57)

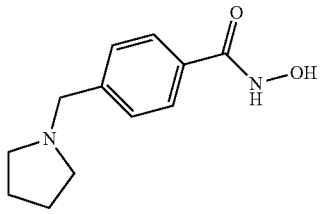

The title compound was synthesized from methyl 4-(pyrrolidin-1-ylmethyl)benzoate 56 (0.120 g, 0.55 mmol) according to General Procedure B (prep. HPLC method 2) and isolated as the trifluoroacetic acid salt (38 mg, 21%). $^1$H NMR (400 MHz, DMSO-$d_6$): δ 11.33 (s, 1H), 10.69 (br, 1H), 9.15 (br, 1H), 7.81 (d, J=8.0 Hz, 2H), 7.58 (d, J=8.0 Hz, 2H), 4.39 (s, 2H), 3.22 (br, 4H), 1.94 (br, 4H). $^{13}$C NMR (100 MHz, MeOD): δ 165.61, 134.17, 133.62, 130.29, 127.62, 57.21, 53.60, 22.37. ESI-HRMS: calc. for $C_{12}H_{16}N_2O_2$: $[M+H]^+$=221.1285 m/z, found: $[M+H]^+$=221.1286 m/z.

(S)-Methyl 4-((2-(methoxymethyl)pyrrolidin-1-yl)methyl)benzoate (58)

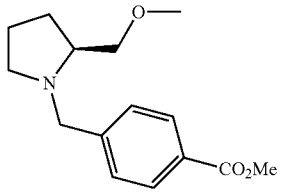

The title compound was synthesized from (S)-2-(methoxymethyl)pyrrolidine (0.175 g, 1.52 mmol) according to a procedure similar to that used for compound 56. $^1$H NMR (400 MHz, $CDCl_3$): δ 7.99 (d, J=8.4 Hz, 2H), 7.42 (d, J=8.0 Hz, 2H), 4.17 (d, J=13.6 Hz, 1H), 3.92 (s, 3H), 3.45 (m, 2H), 3.35 (m, 4H), 2.92 (m, 1H), 2.74 (m, 1H), 2.21 (m, 1H), 1.95 (m, 1H), 1.69 (m, 3H).

(S)-N-Hydroxy-4-((2-(methoxymethyl)pyrrolidin-1-yl)methyl)benzamide.TFA (59)

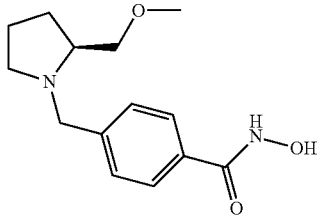

The title compound was synthesized from (S)-methyl 4-((2-(methoxymethyl)pyrrolidin-1-yl)methyl)benzoate 58 (0.120 g, 0.46 mmol) according to General Procedure B (prep. HPLC method 2) and isolated as the trifluoroacetic acid salt (23 mg, 13%). $^1$H NMR (400 MHz, MeOD): δ 7.87 (d, J=8.0 Hz, 2H), 7.64 (d, J=8.0 Hz, 2H), 4.67 (d, J=12.8 Hz, 1H), 4.35 (d, J=12.8 Hz, 1H), 3.85 (br, 1 H), 3.60 (d, J=4.8 Hz, 2H), 3.42 (br, 4H), 3.32 (m, 1H), 2.30 (m, 1H), 2.15 (m, 1H), 1.95 (m, 2H). $^{13}$C NMR (100 MHz, MeOD): δ 165.55, 133.74, 130.81, 127.55, 69.86, 67.00, 58.08, 57.75, 54.48, 26.03, 21.81. ESI-HRMS: calc. for $C_{14}H_{20}N_2O_3$: $[M+H]^+$=265.1547 m/z, found: $[M+H]^+$=265.1550 m/z.

(R)-Methyl 4-((2-(methoxymethyl)pyrrolidin-1-yl)methyl)benzoate (60)

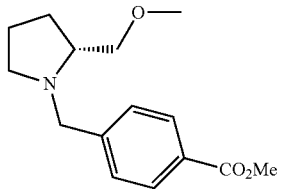

The title compound was synthesized from (R)-2-(methoxymethyl)pyrrolidine (0.175 g, 1.52 mmol) according to a procedure similar to that used for compound 56. $^1$H NMR (400 MHz, $CDCl_3$): δ 7.98 (d, J=8.0 Hz, 2H), 7.41 (d, J=8.0 Hz, 2H), 4.16 (d, J=13.6 Hz, 1H), 3.91 (s, 3H), 3.42 (m, 2H), 3.33 (m, 4H), 2.92 (m, 1H), 2.73 (m, 1H), 2.19 (m, 1H), 1.93 (m, 1H), 1.70 (m, 3H). $^{13}$C NMR (100 MHz, $CDCl_3$): δ 166.7, 144.7, 129.1, 128.4, 128.3, 76.0, 62.8, 58.9, 58.7, 54.2, 51.6, 28.0, 22.4. ESI-LRMS: $[M+H]^+$=264 m/z.

(R)—N-Hydroxy-4-(2-(methoxymethyl)pyrrolidin-1-yl)methyl)benzamide.TFA (61)

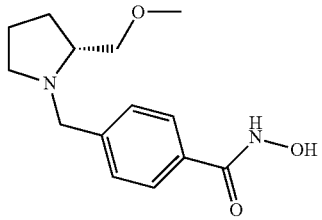

The title compound was synthesized from (R)-methyl 4-((2-(methoxymethyl)pyrrolidin-1-yl)methyl)benzoate 60 (0.120 g, 0.46 mmol) according to General Procedure B (prep. HPLC method 2) and isolated as the trifluoroacetic acid salt (21 mg, 12%). $^1$H NMR (400 MHz, DMSO-$d_6$): δ 11.23 (s, 1H), 9.87 (br, 1H), 9.02 (br, 1H), 7.71 (d, J=8.4 Hz, 2H), 7.49 (d, J=8.0 Hz, 2H), 4.45 (d, J=12.8 Hz, 1H), 4.20 (m, 1H), 3.62 (br, 1H), 3.47 (m, 1H), 3.39 (m, 1H), 3.17 (s, 4H), 3.08 (br, 1H), 2.05 (m, 1H), 1.87 (m, 1H), 1.736 (m, 1H), 1.63 (m, 1H). $^{13}$C NMR (100 MHz, DMSO-$d_6$): δ 163.85, 134.05, 131.35, 127.68, 70.70, 66.37, 58.91, 57.36, 54.37, 26.59, 22.16. ESI-HRMS: calc. for $C_{14}H_{20}N_2O_3$: $[M+H]^+$=265.1547 m/z, found: $[M+H]^+$=265.1551 m/z.

The effectiveness, or potency, of a present HDACI with respect to inhibiting the activity of an HDAC is measured by an $IC_{50}$ value. The quantitative $IC_{50}$ value indicates the concentration of a particular compound that is needed to inhibit the activity of an enzyme by 50% in vitro. Stated alternatively, the $IC_{50}$ value is the half maximal (50%) inhibitory concentration of a compound tested using a specific enzyme, e.g., HDAC, of interest. The smaller the $IC_{50}$ value, the more potent the inhibiting action of the compound because a lower concentration of the compound is needed to inhibit enzyme activity by 50%.

In preferred embodiments, a present HDACI inhibits HDAC enzymatic activity by about at least 50%, preferably at least about 75%, at least 90%, at least 95%, or at least 99%.

Compounds of the present invention were tested for $IC_{50}$ values against both HDAC6 and HDAC1. In some embodiments, a present compound also was tested against HDAC1, 2, 3, 4, 5, 8, 10, and 11. The tested compounds showed a range of $IC_{50}$ values vs. HDAC6 of about 1 nm to greater than 30 μm, and a range of $IC_{50}$ values vs. HDAC1 of about 91 nm to greater than 30 μm. Therefore, in some embodiments, a present HDACI is a selective HDAC6 inhibitor which, because of a low affinity for other HDAC isozymes, e.g., HDAC1, give rise to fewer side effects than compounds that are non-selective HDAC inhibitors.

In some embodiments, the present HDACIs interact with and reduce the activity of all histone deacetylases in a cell. In some preferred embodiments, the present HDACIs interact with and reduce the activity of fewer than all histone deacetylases in the cell. In certain preferred embodiments, the present HDACIs interact with and reduce the activity of one histone deacetylase (e.g., HDAC-6), but do not substantially interact with or reduce the activities of other histone deacetylases (e.g., HDAC-1, HDAC-2, HDAC-3, HDAC-4, HDAC-5, HDAC-7, HDAC-8, HDAC-9, HDAC-10, and HDAC-11).

The present invention therefore provides HDACIs for the treatment of a variety of diseases and conditions wherein inhibition of HDAC has a beneficial effect. Preferably, a present HDACI is selective for HDAC6 over the other HDAC isozymes by a factor of at least 2, at least 5, at least 10, at least 20, at least 50, at least 100, at least 500, at least 1000, at least 2000, at least 3000, and preferably up to about 4000. For example, in various embodiments, a present HDACI exhibits an $IC_{50}$ value versus HDAC6 that is about 350 or about 1000 times less than the $IC_{50}$ value vs. HDAC1, i.e., a selectivity ratio (HDAC1 $IC_{50}$/HDAC6 $IC_{50}$) of about 350 or about 1000.

Other assays also showed a selectivity of a present HDACI for HDAC6 over HDAC1, 2, 3, 4, 5, 8, 10, and 11 of about 1000.

The $IC_{50}$ values for compounds of structural formula (I) vs. HDAC1 and HDAC6 were determined as follows:

The HDAC1, 2, 4, 5, 6, 7, 8, 9, 10, and 11 assays used isolated recombinant human protein; HDAC3/NcoR2 complex was used for the HDAC3 assay. Substrate for HDAC1, 2, 3, 6, 10, and 11 assays is a fluorogenic peptide from p53 residues 379-382 (RHKKAc); substrate for HDAC8 is fluorogenic diacyl peptide based on residues 379-382 of p53 ($RHK_{Ac}K_{Ac}$). Acetyl-Lys(trifluoroacetyl)-AMC substrate was used for HDAC4, 5, 7, and 9 assays. Compounds were dissolved in DMSO and tested in 10-dose $IC_{50}$ mode with 3-fold serial dilution starting at 30 μM. Control Compound Trichostatin A (TSA) was tested in a 10-dose $IC_{50}$ with 3-fold serial dilution starting at 5 μM. $IC_{50}$ values were extracted by curve-fitting the dose/response slopes. Assays were performed in duplicate and $IC_{50}$ values are an average of data from both experiments.

Materials

Human HDAC1 (GenBank Accession No. NM_004964): Full length with C-terminal GST tag, MW=79.9 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >10% by SDS-PAGE. Specific Activity is 20 U/μg, where one U=1 pmol/min under assay condition of 25 mM Tris/Cl, pH8.0, 137 mM NaCl, 2.7 mM KCl, 1 mM $MgCl_2$, 0.1 mg/ml BSA, 100 μM HDAC substrate, and 13.2 ng/μl HDAC1, incubation for 30 min at 30° C.

Human HDAC6 (GenBank Accession No. BC069243): Full length with N-terminal GST tag, MW=159 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >90% by SDS-PAGE. Specific Activity is 50 U/μg, where one U=1 pmol/min under assay condition of 25 mM Tris/Cl, pH8.0, 137 mM NaCl, 2.7 mM KCl, 1 mM $MgCl_2$, and 0.1 mg/ml BSA, 30 μM HDAC substrate, and 5 ng/μl HDAC6, incubation for 60 min at 30° C.

Substrate for HDAC1 and HDAC6: Acetylated peptide substrate for HDAC, based on residues 379-382 of p53 (Arg-His-Lys-Lys(Ac)), a site of regulatory acetylation by the p300 and CBP acetyltransferases (lysines 381, 382)1-6, is the best for HDAC from among a panel of substrates patterned on p53, histone H3 and histone H4 acetylation sites 7.

References: W. Gu et al., Cell (1997) 90 595; K. Sakaguchi et al., Genes Dev., (1998) 12 2831; L. Liu et al., Mol. Cell. Biol., (1999) 19 1202; A. Ito et al., EMBO J., (2001) 20 1331; N. A. Barley et al., Mol. Cell, (2001) 8 1243; and A. Ito et al., EMBO J., (2002) 21 6236.

Reaction Buffer: 50 mM Tris-HCl, pH 8.0, 137 mM NaCl, 2.7 mM KCl, 1 mM $MgCl_2$, 1 mg/ml BSA.

Assay Conditions

HDAC1: 75 nM HDAC1 and 50 μM HDAC substrate are in the reaction buffer and 1% DMSO final. Incubate for 2 hours at 30° C.

HDAC6: 12.6 nM HDAC6 and 50 μM HDAC substrate are in the reaction buffer and 1% DMSO final. Incubate for 2 hours at 30° C.

$IC_{50}$ Calculations

All $IC_{50}$ values are automatically calculated using the GraphPad Prism version 5 and Equation of Sigmoidal dose-response (variable slope):

Y=Bottom+(Top−Bottom)/(1+10^((Log EC50−X)*HillSlope)), where X is the logarithm of concentration, Y is the response, Y starts at Bottom and goes to Top with a sigmoid shape. In most cases, "Bottom" is set 0, and "Top" is set "less than 120%". This is identical to the "four parameter logistic equation". $IC_{50}$ curves also are drawn using the GraphPad Prism, and $IC_{50}$ values and Hill slopes are provided.

HDAC Activity Assays: HDAC assay is performed using fluorescently-labeled acetylated substrate, which comprises an acetylated lysine side chain. After incubation with HDAC, deacetylation of the substrate sensitizes the substrate such that, in a second step, treatment with the detection enzyme produces a fluorophore. HDACs 1 and 6 were expressed as full length fusion proteins. Purified proteins were incubated with 50 μM fluorescently-labeled acetylated peptide substrate and test compound for 2 hours at RT in HDAC assay buffer containing 50 mM Tris-HCl (pH 8.0), 137 mM NaCl, 2.7 mM KCl, 1 mM $MgCl_2$, 1% DMSO, and 1% BSA.

Reactions were terminated by the addition of the Developer after 2 hours, and the development of fluorescence signal, which was relative to the amount of deacetylated peptide, was monitored by time-course measurement of En Vision (PerkinElmer). The HDAC activity was estimated from the slope of time-course measurement of the fluorescence intensity. The slope of no-enzyme control (substrate alone) was served as background, and % Enzyme activity was calculated using background-subtracted slope of no inhibitor control (DMSO) as 100% activity.

To date, HDACIs have demonstrated a relatively non-specific inhibition of various HDAC isozymes. Most HDACI so far identified primarily inhibit HDAC 1, 2, 3, and 8, producing an antiproliferative phenotype which is useful for oncology applications, but not for the many non-oncology applications of HDACIs. (K. B. Glaser et al, Biochemical and biophysical research communications 2003, 310, 529-36.) The potential toxicities associated with the inhibition of certain HDAC isozymes can lead to additional difficulties for the clinical development of pan-HDAC, i.e., nonselective HDAC, inhibitors. Because the network of cellular effects mediated by acetylation is so vast and because inhibition of some HDAC isozymes may lead to undesirable side effects, HDAC isozyme selective inhibitors hold a greater therapeutic promise than their nonselective counterparts.

As illustrated below, many HDACIs of the present invention exhibit selective inhibition of HDAC6 compared to other HDAC isozymes.

TABLE 1

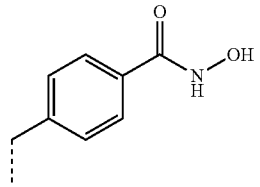

| Cap | HDAC Isoform $IC_{50}$ (μM) 1 | 2 | 3 | 4 | 5 | 6 | 7 | 8 | 9 | 10 | 11 | HDAC6 Selectivity (HDAC1/HDAC6) |
|---|---|---|---|---|---|---|---|---|---|---|---|---|
| 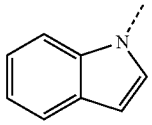 | 5.83 | 9.19 | | | | 0.00975 | | 0.417 | 8.16 | | | 598 |
| 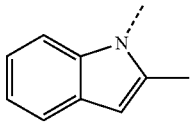 | 5.34 | 8.14 | | | | 0.00251 | | 0.397 | 18.3 | | | 2127 |
| 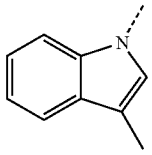 | 6.79 | 11.9 | | | | 0.00511 | | 0.911 | 14.5 | | | 1329 |
| 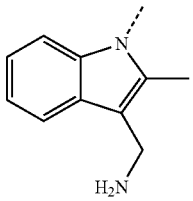 | 3.09 | | | | | 0.00146 | | | | | | 2116 |
| 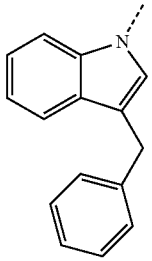 | 13.2 | | | | | 0.0293 | | 0.324 | | | | 451 |

TABLE 1-continued
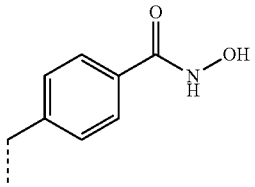
| Cap | HDAC Isoform $IC_{50}$ (μM) 1 | 2 | 3 | 4 | 5 | 6 | 7 | 8 | 9 | 10 | 11 | HDAC6 Selectivity (HDAC1/HDAC6) |
|---|---|---|---|---|---|---|---|---|---|---|---|---|
| 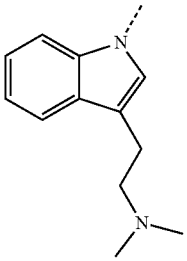 | 5.86 | | | | | 0.0125 | | 0.422 | | | | 469 |
| 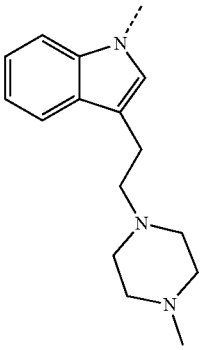 | 1.23 | | | | | 0.00294 | | 0.174 | | | | 418 |
| 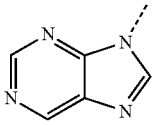 | 0.940 | | | | | 0.00348 | | | | | | 270 |
| 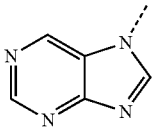 | 3.56 | | | | | 0.0142 | | | | | | 251 |
| 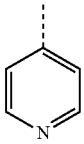 | 6.47 | | | | | 0.0358 | | | | | | 181 |
| 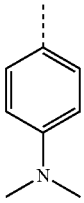 | 6.87 | | | | | 0.0119 | | | | | | 577 |

TABLE 1-continued
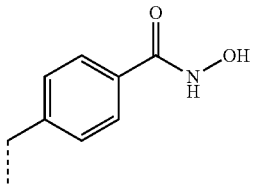
| Cap | HDAC Isoform $IC_{50}$ (μM) 1 | 2 | 3 | 4 | 5 | 6 | 7 | 8 | 9 | 10 | 11 | HDAC6 Selectivity (HDAC1/HDAC6) |
|---|---|---|---|---|---|---|---|---|---|---|---|---|
| 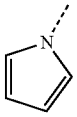 | 5.73 | | | | | 0.0313 | | | | | | 183 |
| 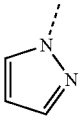 | 1.47 | | | | | 0.0109 | | | | | | 135 |
| 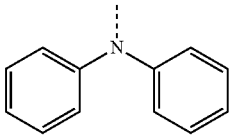 | 6.66 | | | | | 4.50 | | 2.38 | | | | 1.48 |
| 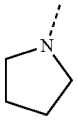 | 29.0 | | | | | 0.540 | | 1.20 | | | | 54 |
| 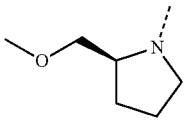 | 27.9 | | | | | 0.150 | | 1.82 | | | | 186 |
| 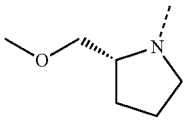 | >30 | | | | | 1.25 | | 5.59 | | | | >24 |
| 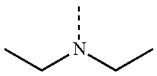 | >30 | | | | | 6.28 | | 9.43 | | | | >5 |
| 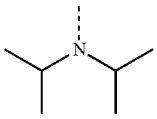 | 23.8 | | | | | 0.124 | | 1.92 | | | | 192 |

TABLE 2
HDAC inhibition data for inventive HDACIs and comparative HDAC inhibitors.
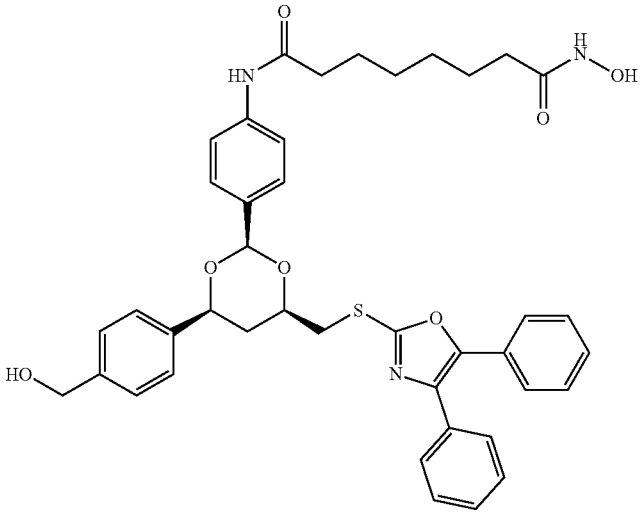
Tubacin
(Comparative)
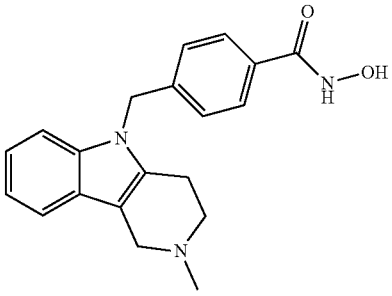
Tubastatin A
(Comparative)
| | HDAC Isoform $IC_{50}$ (μM) | | | | | | | | | | |
|---|---|---|---|---|---|---|---|---|---|---|---|
| Compound | 1 | 2 | 3 | 4 | 5 | 6 | 7 | 8 | 9 | 10 | 11 |
| Tubastatin A | 16.4 | >30 | >30 | >30 | >30 | 0.015 | >30 | 0.854 | >30 | >30 | >30 |
| Tubacin | 1.40 | 6.27 | 1.27 | 17.3 | 3.35 | 0.004 | 9.70 | 1.27 | 4.31 | 3.71 | 3.79 |
| Bicyclic | | | | | | | | | | | |
| 2 | 5.83 | 9.19 | | | | 0.00975 | | 0.417 | 8.16 | | |
| 4 | 5.34 | 8.14 | | | | 0.00251 | | 0.397 | 18.3 | | |
| 6 | 6.79 | 11.9 | | | | 0.00511 | | 0.911 | 14.5 | | |
| 8 | 12.2 | | | | | 0.00408 | | | | | |
| 10 | 13.2 | | | | | 0.0293 | | 0.324 | | | |
| 12 | 0.940 | | | | | 0.00348 | | | | | |
| 14 | 3.56 | | | | | 0.0142 | | | | | |
| 17 | 1.23 | | | | | 0.00294 | | 0.174 | | | |
| 19 | 5.86 | | | | | 0.0125 | | 0.422 | | | |
| 21 | 3.09 | | | | | 0.00146 | | | | | |
| 22 | >30 | | | | | >30 | | | | | |
| 23 | >30 | | | | | >30 | | | | | |
| 27 | 8.54 | | | | | 0.0294 | | | | | |
| 30 | 0.623 | | | | | 0.000170 | | | | | |
| 32 | 8.79 | | | | | 0.0092 | | | | | |
| 36 | 14.7 | | | | | 0.0470 | | | | | |
| 38 | 52.4 | | | | | 0.126 | | | | | |
| 39 | 27.7 | | | | | 0.0470 | | | | | |
| Monocyclic | | | | | | | | | | | |
| 41 | 5.73 | | | | | 0.0313 | | | | | |
| 43 | 1.47 | | | | | 0.0109 | | | | | |
| 45 | 6.47 | | | | | 0.0358 | | | | | |

TABLE 2-continued

| HDAC inhibition data for inventive HDACIs and comparative HDAC inhibitors. | | | |
|---|---|---|---|
| 47 | 6.87 | 0.0119 | |
| 49 | 12.2 | 0.0701 | |
| | | Acyclic | |
| 51 | >30 | 6.28 | 9.43 |
| 53 | 23.8 | 0.124 | 1.92 |
| 55 | 6.66 | 4.50 | 2.38 |
| 57 | 29.0 | 0.540 | 1.20 |
| 59 | 27.9 | 0.150 | 1.82 |
| 61 | >30 | 1.25 | 5.59 |

Assays values are an average of two experiments. ISOX was previously found to have a low picomolar $IC_{50}$ at HDAC6. When ISOX was tested in these assays, an HDAC6 $IC_{50}$ value of 2.4 nM was observed. After investigating the source of this discrepancy, it was found that lack of a detergent (Triton X100) in the original assay caused the anomalously high activity.

The present HDACIs demonstrate excellent HDAC6 potency and selectivity, often exhibiting an $IC_{50}$ of 1 to 5 nM at HDAC6 and 1000- to 2000-fold selectivity against HDAC1. For example, 4 demonstrated an $IC_{50}$ of 2.5 nM at HDAC6 and 2125-fold selectivity against HDAC1.

Ligand efficiency is an important metric to judge the value of potential drugs. Ligand efficiency was proposed after finding that the average molecular weight of successful drugs was lower than those at an early clinical phase, thereby establishing an association between lower molecular weight and a higher chance of clinical success. (C. Abad-Zapatero, et al., Drug discovery today. 10:464-9, 2005; M. C. Wenlock, et al., J Med. Chem. 46:1250-6, 2003). This observation led to the use of ligand efficiency values as an important value for determining lead and clinical candidate selection. Ligand efficiency relates binding free energy to the number of non-hydrogen atoms in the equation: $\Delta g = AG/N$, where N is the number of non-hydrogen atoms, and $\Delta g$ is ligand efficiency. A closely related value used in the analysis of deacetylase inhibitors is binding efficiency index, defined as BEI=pIC50/MW, MW (molecular weight) in kDa.

With the aim of improving ligand efficiency, cap group size was reduced while maintaining potency and selectivity. Table 3 shows that indole, 2-methylindole, and 3-methylindole cap groups had a potency at the target under 10 nM, while maintaining high HDAC6 selectivity. BEI was higher for the indole capped compounds compared to Tubastatin. Substitution at the indole 3' position with ethyldimethylamine or benzyl did not enhance potency at HDAC6 relative to the 2'-unsubstituted indole. Notably, the benzoyl substituted compound had very low activity at HDAC1, below the cutoff value for the assay. The importance of rigidity in the cap group also was investigated through synthesis of compound 55. The diphenylamine cap group of compound 55 is not locked in a planar conformation. The diphenylamine capped compound 55 in Table 3 was more potent and selective compared to an analogous carbazole compound.

Table 3 also shows that the indole and the diphenylamine cap had reduced HDAC8 activity relative to Tubastatin. For compounds to be especially useful as molecular probes of HDAC6 activity, the activity at HDAC8 should be minimized. The diphenylamine capped compound was greatly enhanced in this respect, with over 500-fold selectivity for HDAC6 vs HDAC8 Likewise, the 2-methyl and 3-methylindole cap groups had greater selectivity for HDAC6 over HDAC8 compared to Tubastatin.

TABLE 3

| HDAC6 Inhibitors Featuring an Indole Scaffold. | | | | |
|---|---|---|---|---|
| | HDAC1 $IC_{50}$ (μM) | HDAC6 $IC_{50}$ (μM) | HDAC8 $IC_{50}$ (μM) | BEI |
| Tubastatin | 16.4 ± 2.6 | 0.015 ± 0.001 | 0.854 ± 0.040 | 23.3 |
| 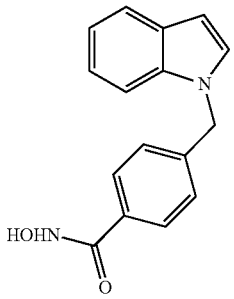 | 5.83 ± 0.70 | 0.0097 ± 0.0003 | 0.417 ± 0.040 | 30.1 |

2

TABLE 3-continued
HDAC6 Inhibitors Featuring an Indole Scaffold.
| | HDAC1 $IC_{50}$ (μM) | HDAC6 $IC_{50}$ (μM) | HDAC8 $IC_{50}$ (μM) | BEI |
|---|---|---|---|---|
| 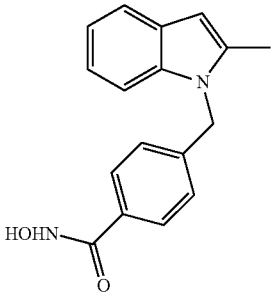 4 | 5.34 ± 0.16 | 0.0025 ± 0.0004 | 0.397 ± 0.099 | 30.7 |
| 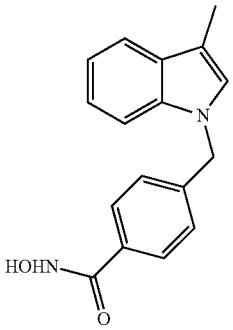 6 | 6.79 ± 0.29 | 0.0051 ± 0.0008 | 0.911 ± 0.042 | 29.6 |
| 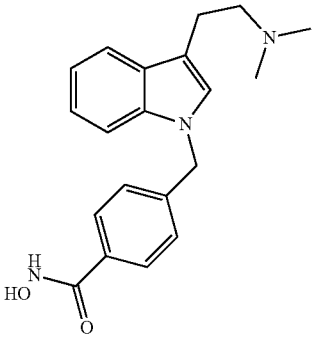 19 | 5.86 ± 1.19 | 0.013 ± 0.002 | 0.422 ± 0.044 | 23.4 |
| 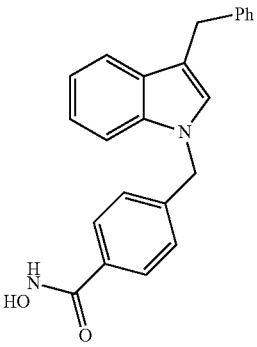 10 | >30 | 0.035 ± 0.003 | NT | 20.9 |

TABLE 3-continued

HDAC6 Inhibitors Featuring an Indole Scaffold.

| | HDAC1 $IC_{50}$ (μM) | HDAC6 $IC_{50}$ (μM) | HDAC8 $IC_{50}$ (μM) | BEI |
|---|---|---|---|---|
| 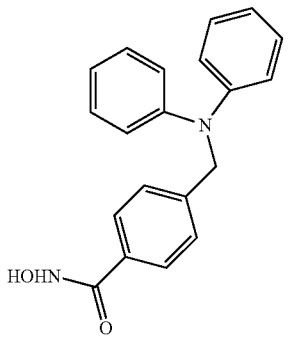 | 6.66 ± 0.51 | 0.0045 ± 0.0004 | 2.38 ± 0.25 | 26.3 |

Values are the mean of two experiments. Data are shown as $IC_{50}$ values in μM±standard deviation. Compounds were tested in duplicate in 10-dose $IC_{50}$ mode with 3-fold serial dilution starting from 30 μM solutions. $IC_{50}$ values were extracted by curve-fitting the dose/response slopes. Assays performed by Reaction Biology Corp.

The present compounds have been evaluated for their activity at HDAC6 and their selectivity for HDAC6 compared to HDAC1. It previously was shown that selective HDAC6 inhibitors are implicated in a variety of disease states including, but not limited to, arthritis, autoimmune disorders, inflammatory disorders, cancer, neurological diseases such as Rett syndrome, peripheral neuropathies such as CMT, stroke, hypertension, and diseases in which oxidative stress is a causative factor or a result thereof. It also was shown that selective HDAC6 inhibitors, when administered in combination with rapamycin, prolonged the lifespan of mice with kidney xenografts. This model was used to evaluate the immunosuppressant properties of the present compounds and serve as a model of transplant rejection. Furthermore, it was previously shown that selective HDAC6 inhibitors confer neuroprotection in rat primary cortical neuron models of oxidative stress. These studies identified selective HDAC6 inhibitors as non-toxic neuroprotective agents. The present compounds behave in a similar manner because they also are selective HDAC6 agents. The present compounds demonstrate a ligand efficiency that renders them more drug-like in their physiochemical properties. In addition, the present compounds maintain the potency and selectivity observed in prior HDACIs. The present compounds therefore are pharmaceutical candidates and research tools to identify the specific functions of HDAC6.

In one embodiment, the present invention relates to a method of treating an individual suffering from a disease or condition wherein inhibition of HDACs provides a benefit comprising administering a therapeutically effective amount of a present HDACI compound to an individual in need thereof.

The methods described herein relate to the use of a present HDACI and an optional second therapeutic agent useful in the treatment of diseases and conditions wherein inhibition of HDAC provides a benefit. The methods of the present invention can be accomplished by administering a present HDACI as the neat compound or as a pharmaceutical composition. Administration of a pharmaceutical composition, or a neat HDACI of the present invention, can be performed during or after the onset of the disease or condition of interest. Typically, the pharmaceutical compositions are sterile, and contain no toxic, carcinogenic, or mutagenic compounds that would cause an adverse reaction when administered.

In many embodiments, a present HDACI is administered in conjunction with a second therapeutic agent useful in the treatment of a disease or condition wherein inhibition of HDAC provides a benefit. The second therapeutic agent is different from the present HDACI. A present HDACI and the second therapeutic agent can be administered simultaneously or sequentially. In addition, a present HDACI and second therapeutic agent can be administered from a single composition or two separate compositions. A present HDACI and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein inhibition of HDAC provides a benefit. The present invention also is directed to pharmaceutical compositions comprising a present HDACI and an optional second therapeutic agent useful in the treatment of diseases and conditions wherein inhibition of HDAC provides a benefit. Further provided are kits comprising a present HDACI and, optionally, a second therapeutic agent useful in the treatment of diseases and conditions wherein inhibition of HDAC provides a benefit, packaged separately or together, and an insert having instructions for using these active agents.

A present HDACI and the second therapeutic agent can be administered together as a single-unit dose or separately as multi-unit doses, wherein the present HDACI is administered before the second therapeutic agent or vice versa. One or more dose of a present HDACI and/or one or more dose of the second therapeutic agent can be administered. The present HDACIs therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, a present HDACI is a potent inhibitor of HDAC and can be used in treating diseases and conditions wherein inhibition of HDAC provides a benefit, for example, cancer, a neurological disease, a neurodegenerative condition, traumatic brain injury, stroke, an inflammation, an autoimmune disease, autism, and malaria.

In one preferred embodiment, the present invention provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof a therapeutically effective amount of a present HDACI.

In one embodiment, the invention provides a method for treating cancer comprising administering to a subject in need thereof an amount of a present HDACI or a pharmaceutically acceptable salt thereof sufficient to treat the cancer. A present HDACI can be used as the sole anticancer agent, or in combination with another anticancer treatment, e.g., radiation, chemotherapy, and surgery.

In another embodiment, the invention provides a method for increasing the sensitivity of a cancer cell to the cytotoxic effects of radiotherapy and/or chemotherapy comprising contacting the cell with a present HDACI or a pharmaceutically acceptable salt thereof in an amount sufficient to increase the sensitivity of the cell to the cytotoxic effects of radiotherapy and/or chemotherapy.

In a further embodiment, the present invention provides a method for treating cancer comprising: (a) administering to an individual in need thereof an amount of a present HDACI compound; and (b) administering to the individual an amount of radiotherapy, chemotherapy, or both. The amounts administered are each effective to treat cancer. In another embodiment, the amounts are together effective to treat cancer.

In another embodiment, the invention provides a method for treating cancer, said method comprising administering to a subject in need thereof a pharmaceutical composition comprising an amount of a present HDACI effective to treat cancer.

This combination therapy of the invention can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiornyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myclomonocytic leukemia, acute nonlymphocyctic leukemia, acute undifferentiated leukemia, chronic myclocytic leukemia, chronic lymphocytic leukemia, hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

The present HDACIs can also be administered to prevent progression to a neoplastic or malignant state, including but not limited to the cancers listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where chronic irritation or inflammation exists, and often is found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include, for example, morphology changes, looser substratum attachment, loss of contact inhibition, loss of anchorage dependence, protease release, increased sugar transport, decreased serum requirement, expression of fetal antigens, disappearance of the 250,000 dalton cell surface protein.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., Archives of Medical Research (1997) 28:265-271), Epstein-Ban virus (EBV) can lead to lymphoma (see, e.g., Herrmann et al., J Pathol (2003) 199(2):140-5), hepatitis B or C virus can lead to liver carcinoma (see, e.g., El-Serag, J Clin Gastroenterol (2002) 35(5 Suppl 2):572-8), human T cell leukemia virus (HTLV)-I can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11):1574-9), and Human Immune deficiency Virus (HIV) infection contribute to cancer development as a consequence of immunodeficiency (see, e.g., Dal Maso et al., Lancet Oncol (2003) 4(2):110-9).

In other embodiments, a subject exhibiting one or more of the following predisposing factors for malignancy can be treated by administration of the present HDACIs and methods of the invention: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.), and exposure to carcinogens (e.g., smoking, and inhalation of or contacting with certain chemicals).

In another specific embodiment, the present HDACIs and methods of the invention are administered to a human subject to prevent progression of breast, colon, ovarian, or cervical cancer.

In one embodiment, the invention provides methods for treating cancer comprising (a) administering to an individual in need thereof an amount of a present HDACI; and (b) administering to the individual one or more additional anti-cancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In one embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, a present HDACI or a pharmaceutically acceptable salt thereof is administered adjunctively with the additional anticancer treatment modality.

In a preferred embodiment, the additional anticancer treatment modality is radiotherapy. In the methods of the present invention, any radiotherapy protocol can be used depending upon the type of cancer to be treated. Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophylla, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present HDACI, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

In a preferred embodiment, a present HDACI or a pharmaceutically acceptable salt thereof is administered prior to the administration of radiotherapy and/or chemotherapy.

In another preferred embodiment, a present HDACI or a pharmaceutically acceptable salt thereof is administered adjunctively with radiotherapy and/or chemotherapy.

A present HDACI and additional treatment modalities can act additively or synergistically (i.e., the combination of a present HDACI or a pharmaceutically acceptable salt thereof, and an additional anticancer treatment modality is more effective than their additive effects when each are administered alone). A synergistic combination permits the use of lower dosages of a present HDACI and/or the additional treatment modality and/or less frequent administration of a present HDACI and/or additional treatment modality to a subject with cancer. The ability to utilize lower dosages of a present HDACI and/or an additional treatment modality and/or to administer a compound of the invention and the additional treatment modality less frequently can reduce the toxicity associated with the administration without reducing the efficacy of a present HDACI and/or the additional treatment modality in the treatment of cancer. In addition, a synergistic effect can result in the improved efficacy of the treatment of cancer and/or the reduction of adverse or unwanted side effects associated with the administration of a present HDACI and/or an additional anticancer treatment modality as monotherapy.

In one embodiment, the present HDACIs may act synergistically with radiotherapy when administered in doses typically employed when such HDACIs are used alone for the treatment of cancer. In another embodiment, the present HDACIs may act synergistically with radiotherapy when administered in doses that are less than doses typically employed when such HDACIs are used as monotherapy for the treatment of cancer.

In one embodiment, radiotherapy may act synergistically with a present HDACI when administered in doses typically employed when radiotherapy is used as monotherapy for the treatment of cancer. In another embodiment, radiotherapy may act synergistically with a compound of the invention when administered in doses that are less than doses typically employed when radiotherapy is used as monotherapy for the treatment of cancer.

The effectiveness of the HDACIs as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14- about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

The present invention provides methods of treating cancers comprising the administration of an effective amount of a present HDACI in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the present HDACIs as radiosensitizers in conjunction with radiotherapy.

When the combination therapy of the invention comprises administering a present HDACI with one or more additional anticancer agents, the present HDACI and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; anyone or a combination of the additional anticancer agents listed below may be administered.

The present invention includes methods for treating cancer comprising administering to an individual in need thereof a present HDACI and one or more additional anticancer agents or pharmaceutically acceptable salts thereof. A present HDACI and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, trofosfamide, chlorambucil, nitrosoureas, carmustine (BCNU), lomustine (CCNU), alkylsulphonates, busulfan, treosulfan, triazenes, plant alkaloids, vinca alkaloids (vineristine, vinblastine, vindesine, vinorelbine), taxoids, DNA topoisomcrase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, floxuridine, doxifluridine, ratitrexed, cytosine analogs, cytarabine (ara C), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, E1) 1089, CB 1093, ICH 1060, photodynamic therapies, vertoporfin, BPD-MA, phthalocyanine, photosensitizer Pc4, demethoxy-hypocrellin A (2BA-2DMHA), cytokines, interferon-α, interferon-I3, interferon-γ, tumor necrosis factor, angiogenesis inhibitors, angiostatin (plasminogen fragment), antiangiogenic antithrombin UI, angiozyme, ABT-627, Bay 12-9566, benefin, bevacizumab, BMS-275291, cartilage-derived inhibitor (CDI), CAI, CD59 complement fragment, CEP-7055, Col 3, combretastatinA-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (UMPs), 2-methoxyestradiol, MMI 270 (CGS 27023A), MoAb IMC-I C11, neovastat, NM-3, panzem, P1-88, placental ribonuclease inhibitor, plasminogen activator inhibitor, platelet factor-4 (PF4), prinomastat, prolactin 161(D fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1), TNP-470, transforming growth factor-beta (TGF-11), vasculostatin, vasostatin (calreticulin fragment), ZD 6126, ZD 6474, farnesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, $Ca^{2+}$ ATPase inhibitors, and thapsigargin.

Other anti-cancer agents that may be used in the present invention include, but are not limited to, acivicin; aclarubicin; acodazole hydrochloride; acronine; adozelesin; aldesleukin; altretamine; arnbomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelcsin; bleomycin sulfate; brequinar sodium; bropirimine; busul fan; cactinomycin; calusterone; caracemide; carbetimer; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexornnaplatin; dezaguanine; dezaguanine mesylate; diaziquone; docetaxel; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mecchlorethamine hydrochloride; megestrol acetate; melengestrol acetate; melphalan; menogaril; mercaptopurine; methotrexate sodium; metoprine; meturedepa; mitindomide; mitocarcin; mitocromin; mitogillin; mitomalcin; mitomycin; mitusper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsornycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracit mustard; uredepa; vapreotide; verteporfln; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride.

Further anti-cancer drugs that can be used in the present invention include, but are not limited to: 17-AAG; 20-epi-1, 25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR-ABL antagonists; benzochlorins; benzoylstaurosporine; beta lactam derivatives; beta alethine; betaclarnycin B; betulinic acid; bFGF inhibitor; bicalutamide; bisantrene; bisaziridinylsperrnine; bisnafide; bistratene A; bizelesin; bortezomib; breflate; bropirimine; budotitane; buthionine sulfoximine; calcipotriol; calphostin C; camptothecin derivatives; canarypox IL-2; carboxamide amino triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexveraparnil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fltidarabine; fluorodaunoruniein hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubiein; ipomeanol, 4; iroplact; irsogladine; isobengazole; isohomohalicondrin B; itasetron; jasplakinolide; kahalalide F; larnellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; acridones; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RH retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the invention that the present HDACIs can be administered in conjunction with chemical agents that are understood to mimic the effects of radiotherapy and/or that function by direct contact with DNA. Preferred agents for use in combination with the present HDACIs for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the present HDACIs as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

The present HDACIs can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a present HDACI effective to eradicate the subject's remaining bone-marrow cell population, then the stem cell graft is infused back into the subject. Supportive care then is provided while bone marrow function is restored and the subject recovers.

The present methods for treating cancer can further comprise the administration of a present HDACI and an additional therapeutic agent or pharmaceutically acceptable salts or hydrates thereof. In one embodiment, a composition comprising a present HDACI is administered concurrently with the administration of one or more additional therapeutic agent(s), which may be part of the same composition or in a different composition from that comprising the present HDACI. In another embodiment, a present HDACI is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

In a preferred embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargramostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, the present HDACIs are used in methods of treating diseases, conditions, and injuries to the central nervous system, such as neurological diseases, neurodegenerative disorders, and traumatic brain injuries (TBIs). In preferred embodiments, a present HDACI is capable of crossing the blood brain barrier to inhibit HDAC in the brain of the individual.

It has been shown that HDAC6 inhibition protects against neuronal degeneration and stimulates neurite outgrowth in dorsal root ganglion neurons, therefore indicating methods of treating CNS diseases. Accordingly, present HDACI compounds were examined in a model of oxidative stress induced by homocysteic acid (HCA). This model leads to depletion of glutathione, the major intracellular antioxidant. HDAC6 inhibition rescues neuronal death in this model, possibly by causing hyperacetylation of peroxiredoxins. Previous work reported that nonselective, hydroxamic acid HDACIs displayed considerable toxicity to the primary cortical neurons. (A. P. Kozikowski et al., J. Med. Chem. 2007, 50, 3054-61.)

Figure 2:
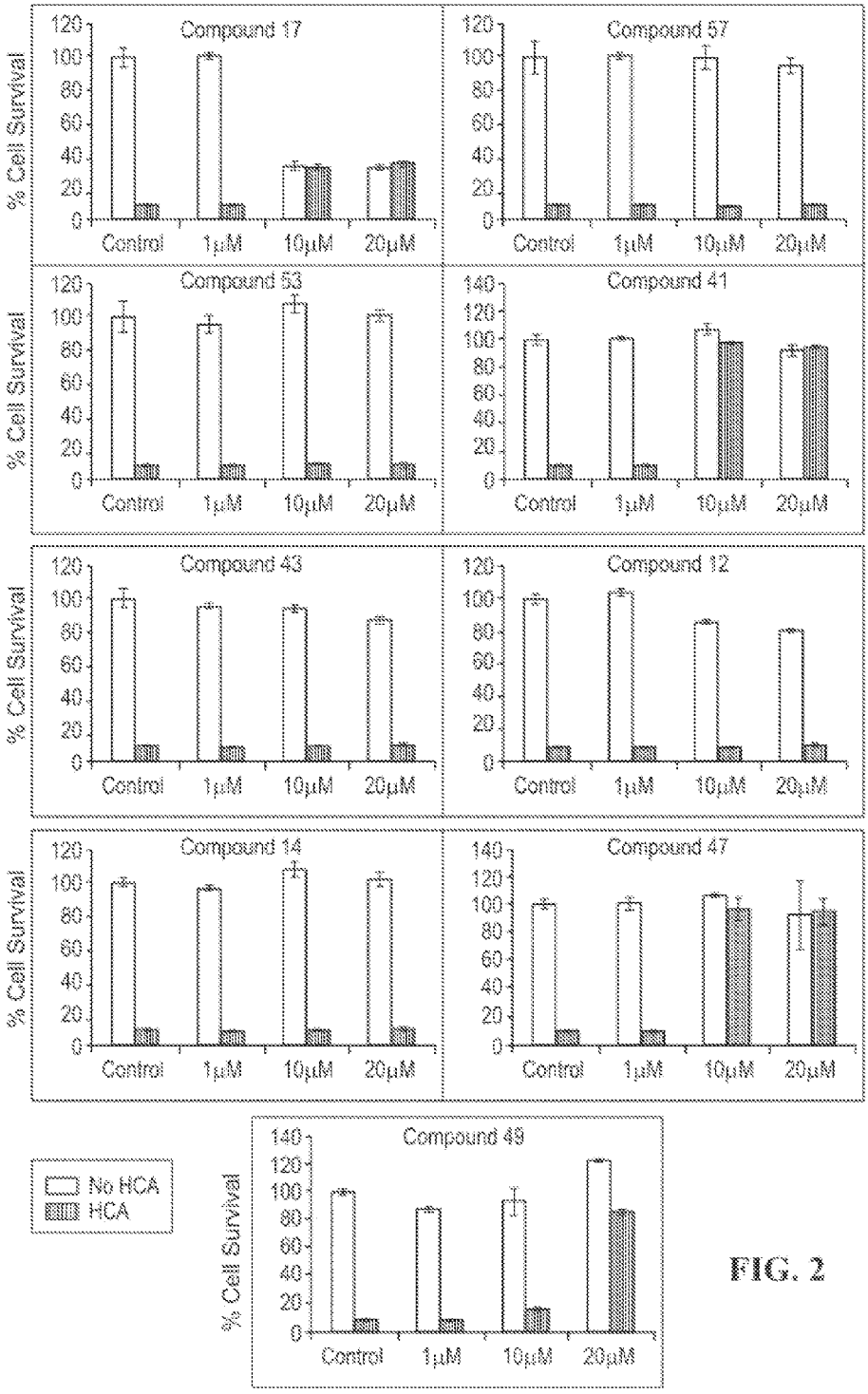
FIG. 2 contains bar graphs of concentrations of various inventive HDACIs vs. survival (% control) for the HCA oxidative stress assay.

In the HCA-induced neurodegeneration assays, TSA was moderately neuroprotective at 0.5 μM, although protection declined at higher concentrations due to dose-dependant neurotoxicity (FIG. 1). Compounds of the present invention displayed dose-dependent protection against HCA-induced neuronal cell death starting at 10 μM with near complete protection at 10 μM (FIG. 2). This compares well with published results showing that Tubacin induces α-tubulin acetylation at 5 μM and protects prostate cancer (LNCaP) cells from hydrogen peroxide-induced death at 8 μM via peroxiredoxin acetylation. (R. B. Parmigiani et al., Proc. Natl. Acad. Sci. USA 2008, 105, 9633-8.) Importantly, when tested at all of the concentrations shown, the present HDACI compounds exhibited no toxicity, indicating that neurotoxicity is likely a product of class I HDAC inhibition, and not a property inherent to hydroxamic acids. These results demonstrate that HDAC6 inhibition provides a method for treating neurodegenerative conditions.

FIGS. 1 and 2 contain neuroprotection bar graphs of the HCA oxidative stress test assay. Neurons were treated with TSA (FIG. 1) or a present HDACI compound (FIG. 2), alone or with the addition of HCA (homocysteic acid).

The data summarized in FIGS. 1 and 2 was obtained according to the following neuroprotective assay. Primary cortical neuron cultures were obtained from the cerebral cortex of fetal Sprague-Dawley rats (embryonic day 17). All experiments were initiated 24 hours after plating. Under these conditions, the cells are not susceptible to glutamate-mediated excitotoxicity. For cytotoxicity studies, cells were rinsed with warm PBS, then placed in minimum essential medium (Invitrogen) containing 5.5 g/liter glucose, 10% fetal calf serum, 2 mM L-glutamine, and 100 μM cystine. Oxidative stress was induced by the addition of the glutamate analog homocysteate (HCA; 5 mM) to the media. HCA was diluted from 100-fold concentrated solutions that were adjusted to pH 7.5. In combination with HCA, neurons were treated with either TSA or a present HDACI compound at the indicated concentrations. Viability was assessed after 24 hours by the MTT assay (3-(4,5-dimethylthiazol-2-yl)-2,5-diphenyltetrazolium bromide) method.

The present HDACI compounds also provide a therapeutic benefit in models of peripheral neuropathies, such as CMT. HDAC6 inhibitors have been found to cross the blood nerve barrier and rescue the phenotype observed in transgenic mice exhibiting symptoms of distal hereditary motor neuropathy. Administration of HDAC6 inhibitors to symptomatic mice increased acetylated α-tubulin levels, restored proper mitochondrial motility and axonal transport, and increased muscle re-innervation. Other peripheral neuropathies include, but are not limited to, giant axonal neuropathy and various forms of mononeuropathies, polyneuropathies, autonomic neuropathies, and neuritis.

The present HDACI compounds also ameliorate associative memory loss following Aβ elevation. In this test, mice were infused with Aβ42 via cannulas implanted into dorsal hippocampus 15 minutes prior to training. The test compounds are dosed ip (25 mg/kg) 2 hours before training. Fear learning was assessed 24 hours later.

Contextual fear conditioning performed 24 hours after training shows a reduction of freezing in Aβ-infused mice compared to vehicle-infused mice. Treatment with a present compound ameliorates deficit in freezing responses in Aβ-infused mice, and has no effect in vehicle-infused mice. A test compound alone does not affect the memory performance of the mice. In addition, treatment had no effects on motor, sensorial, or motivational skills assessed using the visible platform test in which the compounds are injected twice a day for two days. During these experiments, no signs of overt toxicity, including changes in food and liquid intake, weight loss, or changes in locomotion and exploratory behavior, are observed.

These results demonstrate that the HDACIs of the present invention are beneficial against impairment of associative memory following Aβ elevation.

The present HDACIs therefore are useful for treating a neurological disease by administration of amounts of a present HDACI effective to treat the neurological disease or by administration of a pharmaceutical composition comprising amounts of a present HDACI effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCA7), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, multi-infarct state, CMT, GAN and other peripheral neuropathies.

In a preferred embodiment, the neurological disease treated is Huntington's disease, Parkinson's disease, Alzheimer's disease, spinal muscular atrophy, lupus, or schizophrenia.

A present HDACI also can be used with a second therapeutic agent in methods of treating conditions, diseases, and injuries to the CNS. Such second therapeutic agents are those drugs known in the art to treat a particular condition, diseases, or injury, for example, but not limited to, lithium in the treatment of mood disorders, estradiol benzoate, and nicotinamide in the treatment of Huntington's disease.

The present HDACIs also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis (MS), Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

The present HDACIs therefore also are useful in the treatment of inflammation and strokes, and in the treatment of autism and autism spectrum disorders. The present HDACIs further can be used to treat parasitic infections, (e.g., malaria, toxoplasmosis, trypanosomiasis, helminthiasis, protozoal infections (see Andrews et al. Int. J. Parasitol. 2000, 30(6), 761-768).

In certain embodiments, the compound of the invention can be used to treat malaria. A present HDACI can be co-administered with an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones, and iron chelating agents. The antimalarial compound can be, but is not limited to, quinine, quinidine, mefloquine, halfantrine, chloroquine, amodiaquine, proguanil, chloroproquanil, pyrimethamine, primaquine, 8-[(4-amino-1-methylbutyl)amino]-2,6-dimethoxy-4-methyl-5-[(3-trifluoromethyl)phenoxy]quinoline succinate (WR238, 605), tetracycline, doxycycline, clindamycin, azithromycin, fluoroquinolones, artemether, areether, artesunate, artelinic acid, atovaquone, and deferrioxamine. In a preferred embodiment, the antimalarial compound is chloroquine.

The present HDACIs also can be used as imaging agents. In particular, by providing a radiolabeled, isotopically labeled, or fluorescently-labeled HDACI, the labeled compound can image HDACs, tissues expressing HDACs, and tumors. Labeled HDACIs of the present invention also can image patients suffering from a cancer, or other HDAC-mediated diseases, e.g., stroke, by administration of an effective amount of the labeled compound or a composition containing the labeled compound. In preferred embodiments, the labeled HDACI is capable of emitting positron radiation and is suitable for use in positron emission tomography (PET). Typically, a labeled HDACI of the present invention is used to identify areas of tissues or targets that express high concentrations of HDACs. The extent of accumulation of labeled HDACI can be quantified using known methods for quantifying radioactive emissions. In addition, the labeled HDACI can contain a fluorophore or similar reporter capable of tracking the movement of particular HDAC isoforms or organelles in vitro.

The present HDACIs useful in the imaging methods contain one or more radioisotopes capable of emitting one or more forms of radiation suitable for detection by any standard radiology equipment, such as PET, SPECT, gamma cameras, MRI, and similar apparatus. Preferred isotopes including tritium ($^{3}H$) and carbon ($^{11}C$). Substituted HDACIs of the present invention also can contain isotopes of fluorine ($^{18}F$) and iodine ($^{123}I$) for imaging methods. Typically, a labeled HDACI of the present invention contains an alkyl group having a $^{11}C$ label, i.e., a $^{11}C$-methyl group, or an alkyl group substituted with $^{18}F$, $^{123}I$, $^{125}I$, $^{131}I$, or a combination thereof.

Fluorescently-labeled HDACIs of the present invention also can be used in the imaging method of the present invention. Such compounds have an FITC, carbocyamine moiety or other fluorophore which will allow visualization of the HDAC proteins in vitro.

The labeled HDACIs and methods of use can be in vivo, and particularly on humans, and for in vitro applications, such as diagnostic and research applications, using body fluids and cell samples. Imaging methods using a labeled HDACI of the present invention are discussed in WO 03/060523, designating the U.S. and incorporated in its entirety herein. Typically, the method comprises contacting cells or tissues with a radiolabeled, isotopically labeled, fluorescently labeled, or tagged (such as biotin tagged) compound of the invention, and making a radiographic, fluorescent, or similar type of image depending on the visualization method employed, i.e., in regard to radiographic images, a sufficient amount to provide about 1 to about 30 mCi of the radiolabeled compound.

Preferred imaging methods include the use of labeled HDACIs of the present invention which are capable of generating at least a 2:1 target to background ratio of radiation intensity, or more preferably about a 5:1, about 10:1, or about 15:1 ratio of radiation intensity between target and background.

In preferred methods, the labeled HDACIs of the present invention are excreted from tissues of the body quickly to prevent prolonged exposure to the radiation of the radiolabeled compound administered to the individual. Typically, labeled HDACIs of the present invention are eliminated from the body in less than about 24 hours. More preferably, labeled HDACIs are eliminated from the body in less than about 16 hours, 12 hours, 8 hours, 6 hours, 4 hours, 2 hours, 90 minutes, or 60 minutes. Typically, preferred labeled HDACIs are eliminated in about 60 to about 120 minutes.

In addition to isotopically labeled and fluorescently labeled derivatives, the present invention also embodies the use of derivatives containing tags (such as biotin) for the identification of biomolecules associated with the HDAC isoforms of interest for diagnostic, therapeutic or research purposes.

The present HDACIs also are useful in the treatment of autoimmune diseases and inflammations. Compounds of the present invention are particularly useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by costimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (R. Tao et al., Nat Med, 13, 1299-1307, (2007)), and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo sutides are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with floxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

The present compounds are envisioned to demonstrate anti-arthritic efficacy in a collagen-induced arthritis model in DBA1/J mice. In this test, DBA1/J mice (male, 7-8 weeks) are used, with 8 animals per group. Systemic arthritis is induced with bovine collagen type II and CFA, plus an IFA booster injection on day 21. A present HDACI is dosed at 50 mg/kg and 100 mg/kg on day 28 for 2 consecutive weeks, and the effects determined from the Average Arthritic Score vs. Days of Treatment data.

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

The present HDACIs are potent immunosuppressive agents that suppress humoral immunity and cell-mediated immune reactions, such as allograft rejection, delayed hypersensitivity, experimental allergic encephalomyelitis, Freund's adjuvant arthritis and graft versus host disease. HDACIs of the present invention are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of a present HDACI can be used for immunosuppression including, for example, to prevent organ rejection or graft vs. host disease, and to treat diseases and conditions, in particular, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

A present HDACI can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and particularly HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present invention.

In the present method, a therapeutically effective amount of one or more HDACI of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present HDACI can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present HDACI is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present HDACI that is sufficient to maintain therapeutic effects.

Toxicity and therapeutic efficacy of the present HDACI compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present HDACI required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present HDACI, or a composition containing the same, can be from about 1 ng/kg to about 200 mg/kg, about 1 μg/kg to about 100 mg/kg, or about 1 mg/kg to about 50 mg/kg of body weight. The dosage of a composition may be at any dosage including, but not limited to, about 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present HDACI used in a method of the present invention typically is administered in an amount of about 0.005 to about 500 milligrams per dose, about 0.05 to about 250 milligrams per dose, or about 0.5 to about 100 milligrams per dose. For example, a present HDACI can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the present HDACIs.

The term "carrier" refers to a diluent, adjuvant, or excipient, with which a present HDACI is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present HDACI is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present HDACI. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present HDACI is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present HDACI can be infused with other fluids over a 10-30 minute span or over several hours.

The present HDACIs can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present HDACI can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present HDACI can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present HDACI also can be formulated in rectal compositions, such as suppositories or retention enemas, e.g., containing conventional suppository bases. In addition to the formulations described previously, a present HDACI also can be formulated as a depot preparation. Such long-acting formulations can be administered by implantation (for example, subcutaneously or intramuscularly) or by intramuscular injection. Thus, for example, a present HDACI can be formulated with suitable polymeric or hydrophobic materials (for example, as an emulsion in an acceptable oil) or ion exchange resins.

In particular, a present HDACI can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present HDACIs also can be injected parenterally, for example, intravenously, intramuscularly, subcutaneously, or intracoronarily. For parenteral administration, the present HDACIs are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present HDACI and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, the present compounds is a lyophilate. In this instance, the kit can further comprise an additional container which contains a solution useful for the reconstruction of the lyophilate.

Prior HDACIs possessed properties that hindered their development as therapeutic agents. In accordance with an important feature of the present invention, the present HDACIs were synthesized and evaluated as inhibitors for HDAC. The present compounds demonstrate an increased HDAC6 potency and selectivity against HDAC1 and HDAC8 with improvements in BEI relative to prior compounds. The improved properties of the present compounds, particularly the increase in BEI and reduced potency at HDAC8, indicate that the present compounds are useful for applications such as, but not limited to, immunosuppressive and neuroprotective agents. For example, compounds of the present invention typically have a bonding affinity ($IC_{50}$) to HDAC6 of less than 100 μM, less than 25 μM, less than 10 μM, less than 1 μM, less than 0.5 μM, and less than 0.2 μM.

What is claimed:

1. A compound having a structural formula

Cap-L-M wherein Cap is selected from the group consisting of (a)

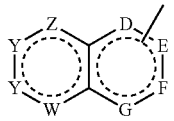

wherein ring

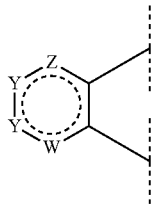

is an aliphatic or aromatic five or six membered ring,

W, X, Y, and Z independently are selected from the group consisting of null, $C(R^1)_2$, [O, S,] and $NR^1$, ring

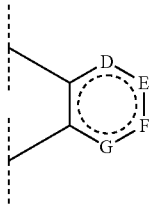

is an aliphatic or aromatic six membered ring, wherein D, E, F, and G independently are selected from the group consisting of $C(R^1)_2$, [O, and S,]

or ring

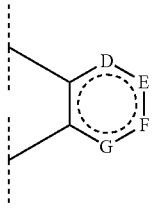

is an aliphatic or aromatic five membered ring, wherein D, E, F, and G are selected from the group consisting of null, $C(R^1)_2$, and $NR^1$, $R^1$, independently, is selected from the group consisting of null, hydrogen, $C_{1-6}$alkyl, $C_{1-6}$heteroalkyl, $C_{2-6}$alkenyl, $C_{1-6}$perfluoroalkyl, $C_{1-6}$perfluoroalkoxy, [aryl, heteroaryl,] $C_{3-10}$cycloalkyl, $C_{3-10}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

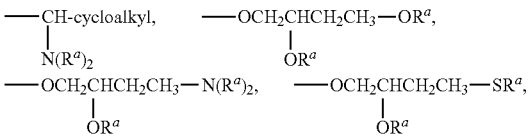

$OR^a$, halo, $N(R^a)_2$, $SR^a$, $SOR^a$, $SO_2R^a$, CN, $C(=O)R^a$, $CF_3$, $OCF_3$, $NO_2$, $OC(=O)R^a$, $SO_2N(R^a)_2$, $OSO_2CF_3$, $C(=O)OR^a$, $C(=O)N(R^a)_2$, $C_{1-6}$alkyleneN$(R^a)_2$, $C_{1-6}$alkyleneC$(=O)R^a$, $C_{1-6}$alkyleneO$R^a$, $C_{1-6}$alkyleneS$R^a$, $C_{1-6}$alkyleneN$R^aSO_2R^a$, $C_{1-6}$alkyleneSO$R^a$, $C_{1-6}$alkyleneCN, $C_{1-6}$heteroalkyleneCN, $C_{1-6}$alkyleneC$(=O)OR^a$, $C_{1-6}$alkyleneOC$(=O)N(R^a)_2$, $C_{1-6}$alkyleneN$R^aC(=O)OR^a$, $C_{1-6}$alkyleneN$R^aC(=O)R^a$, [$C_{1-6}$alkylene $C(=O)N(R^a)_2$] *$C_{1-6}$alkyleneC$(=O)N(R^a)_2$*, $C_{1-6}$alkyleneO$C_{1-6}$alkyleneC$(=O)OR^a$, $C(=O)NR^aSO_2R^a$, $C(=O)C_{1-6}$alkylenearyl, $C(=O)NR^aC_{1-6}$alkyleneO$R^a$, O$C_{1-6}$alkyleneC$(=O)OR^a$, O$C_{1-6}$alkyleneN$(R^a)_2$, O$C_{1-6}$alkyleneO$R^a$, O$C_{1-6}$alkyleneN$R^aC(=O)OR^a$, $NR^aC_{1-6}$alkyleneN$(R^a)_2$, $NR^aC(=O)R^a$, $NR^aC(=O)N(R^a)_2$, $N(SO_2C_{1-6}alkyl)_2$, and $NR^a(SO_2C_{1-6}alkyl)$, and $R^a$, independently, is selected from the group consisting of hydrogen, $C_{1-6}$alkyl, $C_{1-6}$heteroalkyl, $C_{1-6}$alkyleneN$H_2$, $C_{1-6}$alkyleneNH($C_{1-6}$alkyl), $C_{1-6}$alkyleneN$(C_{1-6}alkyl)_2$, $C_{1-6}$alkyleneNH$(C_{1-6}alkyl)_2$, $C_{1-6}$alkyleneNHC$(=O)(C_{1-6}alkyl)$, $C_{1-6}$alkyleneC$(=O)NH_2$, $C_{1-6}$alkyleneOH, $C_{1-6}$alkyleneCN, $C_{1-6}$heteroalkyleneCN, $C_{1-6}$alkyleneO$C_{1-6}$alkyl, $C_{1-6}$alkyleneSH, $C_{1-6}$alkyleneS$C_{1-6}$alkyl, $C_{1-6}$alkyleneNH$(SO_2C_{1-6}alkyl)$, aryl, heteroaryl, $C_{3-8}$cycloalkyl, and $C_{3-10}$heterocycloalkyl, wherein linker L is attached to any atom D, E, F, or G, *and*

(b)

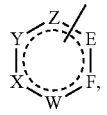

wherein ring

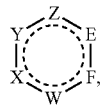

is an aliphatic or aromatic five or six membered ring, E, F, W, X, Y, Z, $R^1$, and $R^a$ are as defined above, [and

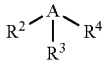

wherein A is C, N, O, S, B, or P, and L is attached to A, $R^2$, $R^3$ and $R^4$ independently are selected from the group consisting of null, hydrogen, $C_{1-6}$alkyl, $C_{1-6}$heteroalkyl, $C_{2-6}$alkenyl, $C_{1-6}$perfluoroalkyl, $C_{1-6}$perfluoroalkoxy, aryl, heteroaryl, $C_{3-10}$cycloalkyl, $C_{3-8}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

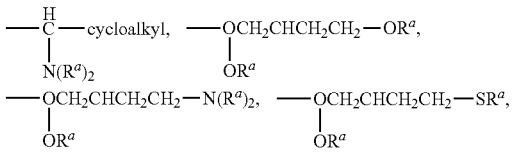

$OR^a$, halo, $N(R^a)_2$, $SR^a$, $SOR^a$, $SO_2R^a$, CN, $C(=O)R^a$, $OC(=O)R^a$, $C(=O)OR^a$, $C_{1-6}$alkyleneN$(R^a)_2$, $C_{1-6}$alkyleneO$R^a$, $C_{1-6}$alkyleneS$R^a$, $C_{1-6}$alkyleneC$(=O)OR^a$, $C(=O)N(R^a)_2$, $C(=O)NR^aC_{1-6}$alkyleneO$R^a$, O$C_{1-6}$alkyleneC$(=O)OR^a$, O$C_{1-6}$alkyleneN$(R^a)_2$, O$C_{1-6}$alkyleneO$R^a$, O$C_{1-6}$alkyleneN$R^aC(=O)OR^a$, $NR^aC_{1-6}$alkyleneN$(R^a)_2$, $NR^aC(=O)R^a$, $NR^aC(=O)N(R^a)_2$, $N(SO_2C_{1-6}alkyl)_2$, $NR^a(SO_2C_{1-6}alkyl)$, nitro, and $SO_2N(R^a)^2$, and $R^a$ is defined above;] *wherein at least one of E, F, W, X, Y, and Z is $NR^1$;*

L is [selected from the group consisting of null, $C_{1-8}$alkylene, $R^a$ substituted $C_{1-8}$alkylene, $NR^a$, C(=O), aryl, C(=O)aryl, C(=O)$C_{1-6}$alkylene, $C_{1-8}$alkyleneN$R^a$, $C_{1-6}$alkylenearyleneC$_{1-6}$alkylene, $C_{2-6}$alkenylene, $C_{4-8}$alkdienylene, $C_{1-6}$alkylenearylene, $C_{1-6}$alkyleneheteroarylene, $R^a$ substituted $C_{1-6}$alkyleneheteroarylene, and $C_{2-6}$alkenylenearyleneC$_{1-6}$alkylene, and $R^a$ is defined above] *$CH_2$—$C_6H_5$*;

M is

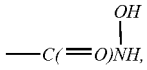

[selected from the group consisting of —C(=O)N($R^b$)OH,

—O$(CH_2)_{1-6}$C(=O)N($R^b$)O$R^b$,

—N($R^b$)$(CH_2)_{1-6}$C(=O)N($R^b$)O$R^b$,

—N($R^b$)$(CH_2)_{1-6}$C(=O)N($R^b$)O$R^b$, arylC(=O)NHOH,

—N(OH)C(=O)$R^b$, heteroarylC(=O)NHOH,

—$C_{3-6}$cycloalkylN—C(=O)$CH_2$SH,

—B$(OR^b)_2$, $SO_2NHR^b$,

—$NHSO_2NHR^b$, $NHSO_2C_{1-6}$alkyl,

—$SO_2C_{1-6}$alkyl,

—$SR^c$,

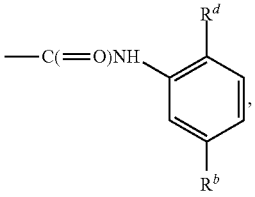

—C(═O)$R^e$,
—P(═O)($OR^f$)$_2$,
—NH—P(═O)($OR^f$)$_2$,

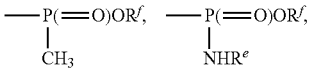

—C(═O)(C($R^b$)$^2$)$_{1-6}$SH,
—C(═O)C(═O)NH$R^b$,
—C(═O)NHN($R^b$)$_2$,
—C(═O)NH($CH_2$)$_{1-3}$N($R^b$)$_2$,

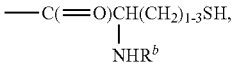

—S—(C═O)$C_{1-6}$alkyl,
$C_{3-10}$heterocycloalkyl optionally substituted with oxo (═O), thioxo (═S), or both,
aryl optionally substituted with one or more of $C_{1-6}$alkyl, —C(═O)$R^d$, —$NH_2$, and —SH,
heteroaryl optionally substituted with —$NH_2$, —SH, or both,
—N(H)C(═O)SH,
—NHC(═O)NH$R^d$,
—NHC(═O)$CH_2R^d$,
—NHC(═O)($CH_2$)$_{1-6}$SH,
—NHC(═O)$CH_2$Hal,
—NHC(═S)NH$R^d$,
—NHC(═S)$CH_2R^d$,
—C(═S)NH$R^d$,
—C(═S)$CH_2R^d$,
—NHC(═S)$CH_2R^d$,
—NHC(═S)$CH_2$Hal, and
—(C═O)$C_{1-6}$alkyl;
$R^b$, independently, is selected from the group consisting of hydrogen, (C═O)$CH_3$, $C_{1-6}$alkyl, $CF_3$, $CH_2F$, and aryl, or two $R^b$ groups are taken together with the carbon to which they attached to form a $C_{3-8}$cycloalkyl group;
$R^c$ is selected from hydrogen or (C═O)$CH_3$;
$R^d$ is $NH_2$ or OH;
$R^e$ is selected from the group consisting of OH, N($R^b$)$^2$, NH($OCH_3$), N($CH_3$)OH, $C_{1-6}$alkyl, $CF_3$, aryl, heteroaryl, $C_{3-8}$cycloalkyl, $NHSO_2CH_3$, $NHSO_2CF_3$, and $C_{1-6}$haloalkyl;
$R^f$ independently is hydrogen, methyl, or ethyl; and
Hal is halo],
or a pharmaceutically acceptable salt, hydrate, or prodrug thereof.

2. The compound of claim 1 wherein the bicyclic ring system

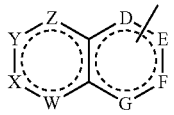

is selected from a residue of the group consisting of [thionaphthene, isothionaphthene,] indole, indolenine, 1H-isoindole, cyclopenta[b]pyridine, [pyrano[3,4-b] pyrrole,] indazole, [benzisoxazole, benzoxazole, anthranil,] naphthalene, tetralin, decalin, [2H-1-benzopyran, coumarin, coumarin-4-one, isochromen-1-one, isochromen-3-one,] quinoline, isoquinoline, cinnoline, quinazoline, [naphthyridine, pyrido[3,4-b]-pyridine, pyrido[3,2-b]-pyridine, pyrido[4,3-b]-pyridine, 2H-1, 3-benzoxazine, 1H-2,3-benzoxazine, 4H-3,1-benzoxazine, 2H-1,2-benzoxazine, 4H-1,4-benzoxazine,] purine, indoline, [benzo(b)furan,] indene, pteridine, quinoxaline, benzimidazole, [benzthiazole,] and phthalzine,
and wherein the linker L is attached to any atom D, E, F, G, W, X, Y, or Z.

3. The compound of claim 1 wherein

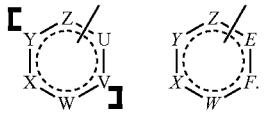

is selected from the group consisting of [cyclohexyl, cyclohexenyl, cyclopentyl, cyclopentenyl, cycloheptyl, cycloheptenyl, phenyl, furanyl,] 2H-pyrrolyl, [thienyl,] pyrrolyl, [oxazolyl, thiazolyl,] imidazolyl, pyrazolyl, [isoxazolyl, isothiazolyl, 1,2,3,-oxadiazolyl,] 1,2,3,-triazolyl, [1,2,5-oxadiazolyl,] 2-pyrrolinyl, 3-pyrrolinyl, pyrrolidinyl, [1,3-dioxolanyl,oxazolyl,] 2-imidazolinyl, imidazolidinyl, 2-pyrazolinyl, pyrazolidinyl, 3H-pyrrolyl, [1,3-dithiolyl, 3H-1,2-oxathiolyl, 3H-1,2, 3-dioxazolyl, 1,3,2-dioxazolyl, 1,2-dithiolyl, 5H-1,2,5-oxathiazolyl, 1,3-oxathiolyl, 2H-pyranyl, 4H-pyranyl, piperidinyl, 1,4-dioxanyl, morpholinyl, 1,4-dithianyl, thiomorpholinyl,] pyrimidinyl, piperazinyl, [2-pyronyl, 4-pyronyl, 1,2-dioxinyl, 1,3-dioxinyl, 1,2,4-triazinyl,] 1,2,3-triazinyl, [4H-1,3-oxazinyl, 2H-1,3-oxazinyl, 6H-1,3-oxazinyl, 6H-1,2-oxazinyl, 4H-1,4-oxazinyl, 2H-1,2-oxazinyl, 1,4-oxazinyl, p-isoxazinyl, o-isoxazinyl,] pyridinyl, [1,2,6-oxathiazinyl, 1,2,5-oxathiazinyl, 1,4,2-oxadiazinyl,] pyridazinyl, *and* pyrazinyl[, azacycloheptyl, azacycloheptenyl, oxacycloheptyl, and thiacycloheptyl],
wherein linker L is attached to any atom [U, V] *E, F*, W, X, Y, or Z.

4. The compound of claim 1 wherein the Cap group has a structure:

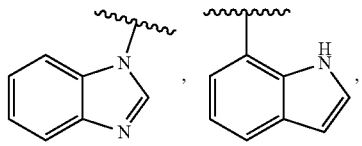

-continued

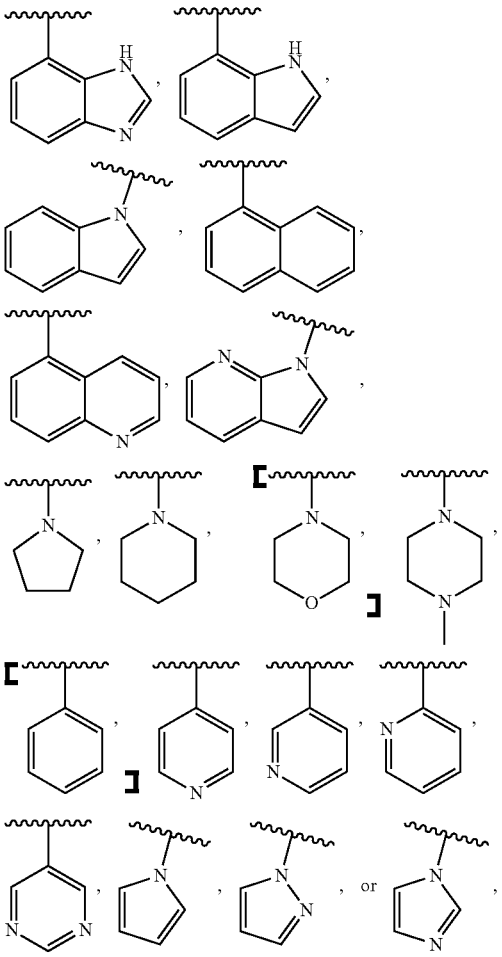

either unsubstituted or substituted with one or more $R^1$.

[5. The compound of claim 1 wherein

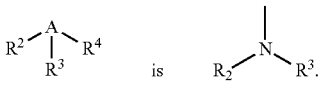

]

6. The compound of claim 1 wherein $R^1$ is selected from the group consisting of null, hydrogen, $OR^a$, halo, $C_{1-6}$alkyl, [aryl,] heterocycloalkyl, —$(CH_2)_{1-4}$heterocycloalkyl, —$(CH_2)_{1-4}N(R^a)_2$,

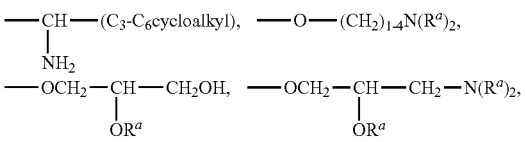

or —C(═O)$N(CH_2)_{1-4}N(R^a)_2$.

7. The compound of claim 1 wherein $R^a$ is selected from the group consisting of [null,] hydrogen, $C_{1-6}$alkyl, $C_{1-6}$heteroalkyl, aryl, and heteroaryl.

[8. The compound of claim 1 wherein L is null, —$(CH_2)_{1-6}$—,

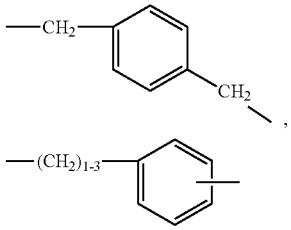

optionally substituted with halo, $CF_3$, or CN,

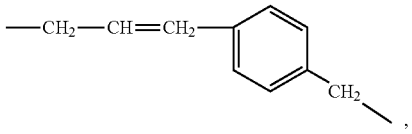

—$CH_2$—CH═$CH_2$—, —$(CH_2)_2$—CH═CH—CH═$CH_2$—, —$(CH_2)_{0-6}$—NH—,

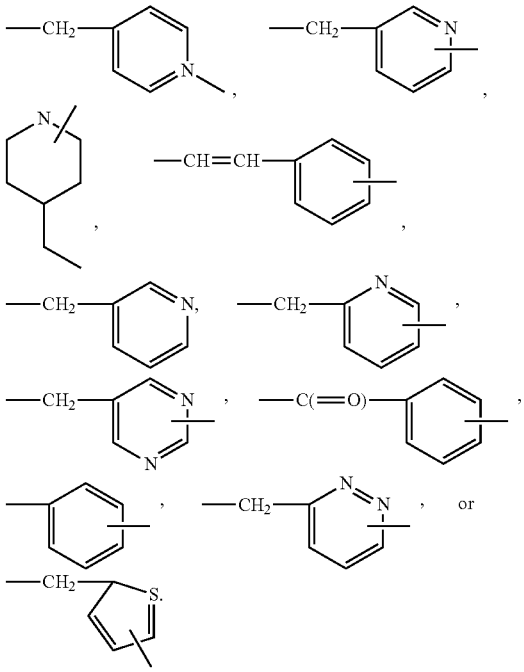

]

[9. The compound of claim 1 wherein M is

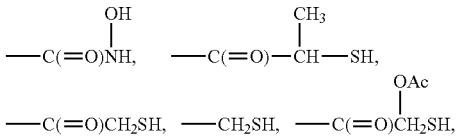

—SC(═O)tBu, —SC(═O)$CF_3$, —S$(CH_2)_{1-3}$C(═O)$CF_3$, —$CH_2$SAc,

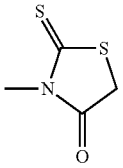
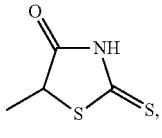
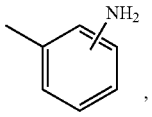
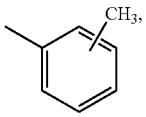

—NH—C(═O)$CH_2$SH,

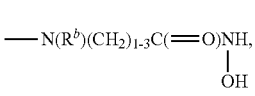
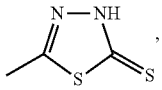
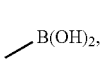
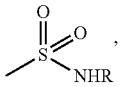
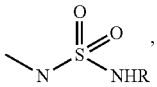

R = H or alkyl or —OH

R = H or alkyl or —OH

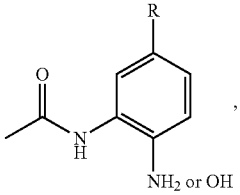

R = H or alkyl

R is aryl

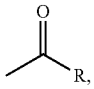

R = OH, $NH_2$ NHOMe, NMeOH, $C_{1-4}$alkyl, $CF_3$, heterocycle, $NHSO_2CH_3$, $NHSO_2CF_3$, NH-Alkyl, $NMe_2$, $OR^b$, halo$C_{1-4}$alkyl, aryl, heteroaryl, $C_{3-8}$cycloalkyl, $C_{3-10}$heterocycloakyl

—C(═O)NHNHR,

R = OH, $NH_2$

—O$(CH_2)_{1-3}$C(═O)NH(OH), —C(═O)OR,

R = H or alkyl

—C(═O)N$(CH_2)_{1-3}$N(R)$_2$, —N(OH)C(═O)R,

R = H or alkyl R = H or alkyl

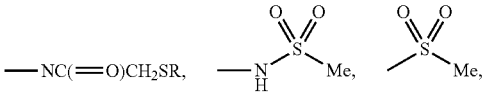

—NC(═O)$CH_2$SR,

R = H or alkyl

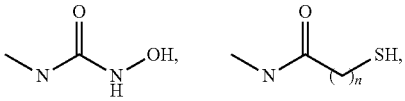

n = 1-9

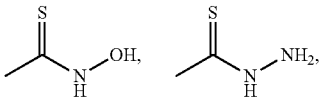

—SR,

R = H, Ac, Me

-continued

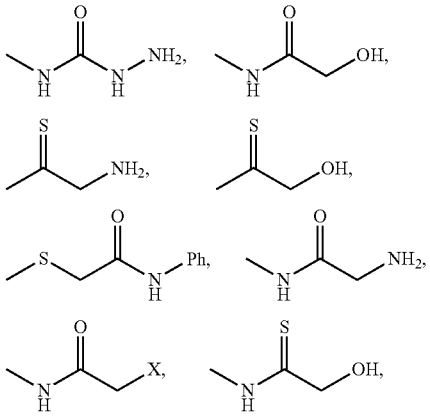

X = F, Cl, Br

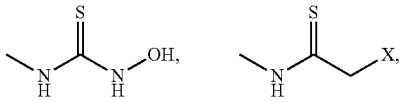

X = F, Cl, Br

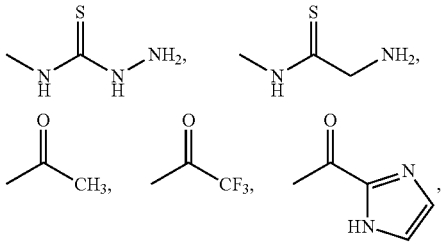

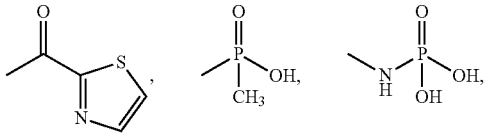

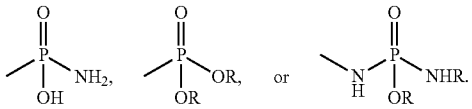

R = H, Me, Et R = H, Me, Et

]

10. The compound of claim 1 wherein the Cap group is selected from the group consisting of

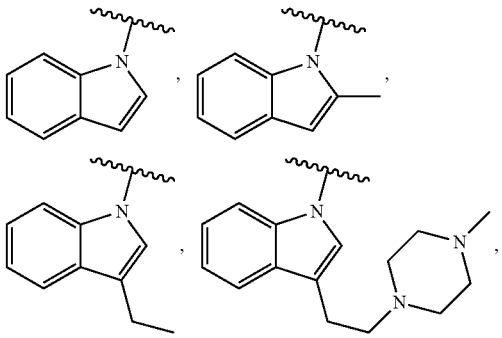

-continued
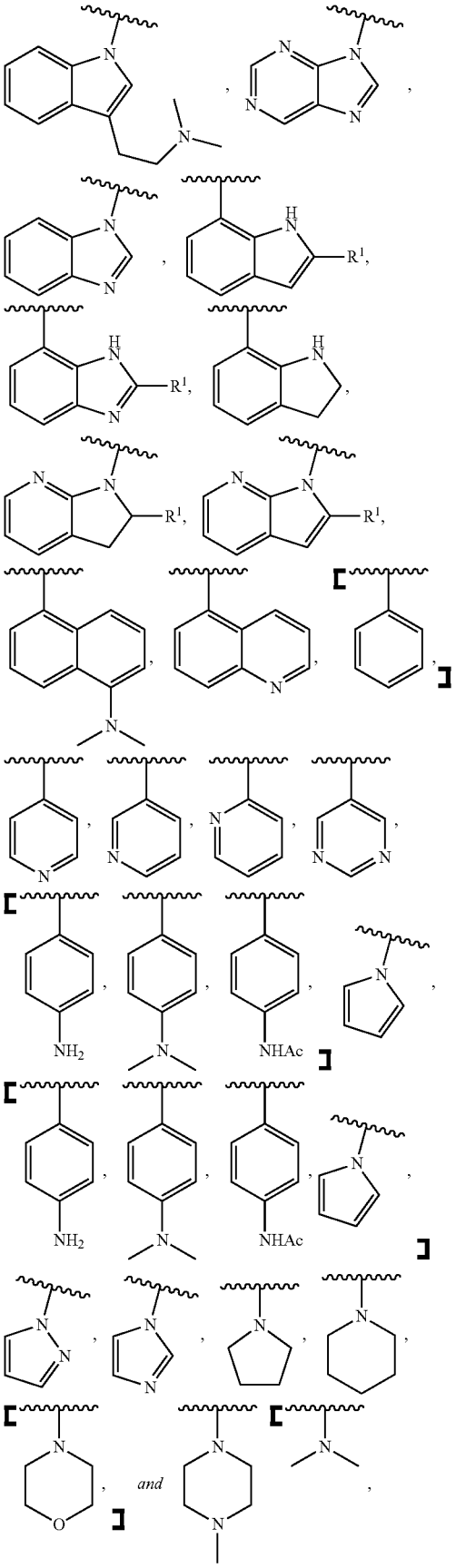
-continued
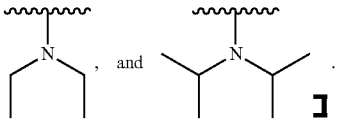
11. A composition comprising (a) compound of claim 1, (b) an optional second therapeutic agent useful in the treatment of a disease or condition wherein inhibition of histone deacetylase provides a benefit, and (c) an excipient and/or pharmaceutically acceptable carrier.
12. A compound selected from the group consisting of
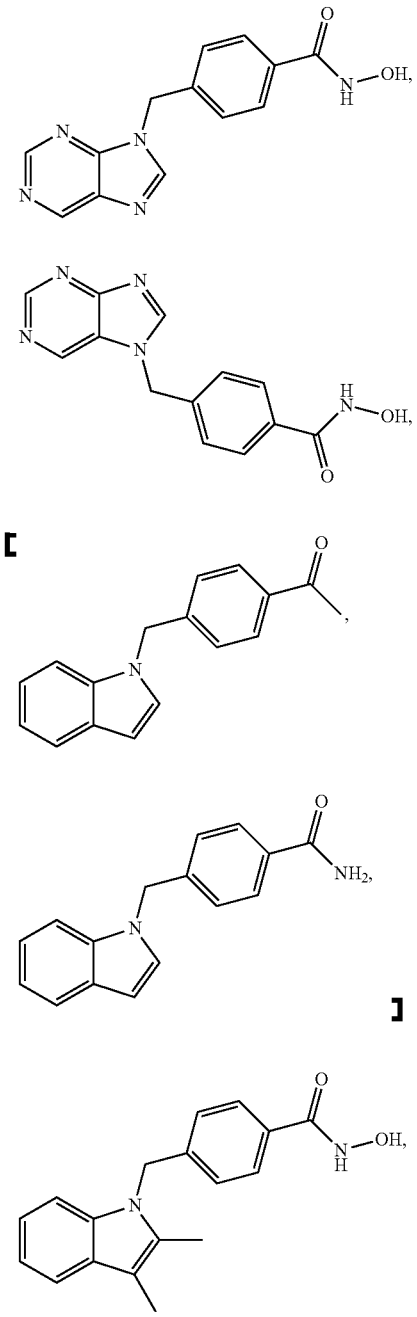

-continued
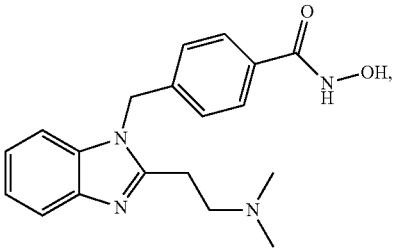
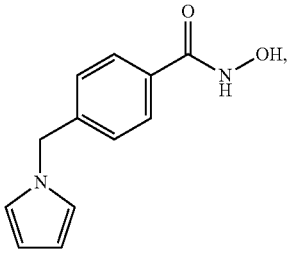
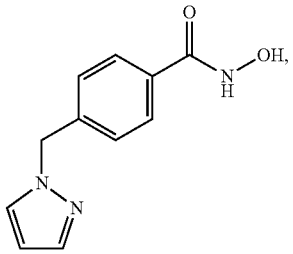
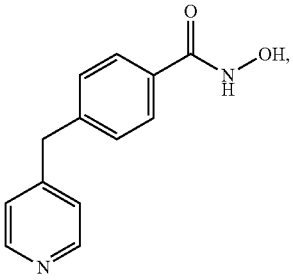
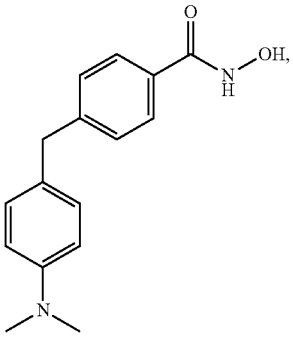
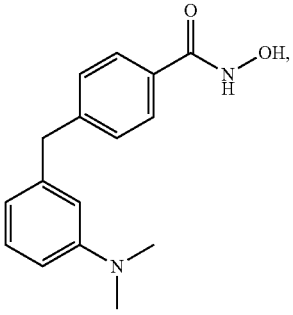
-continued
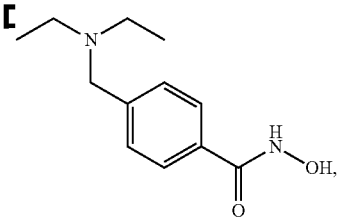
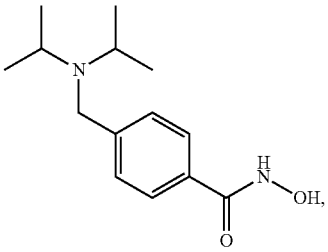
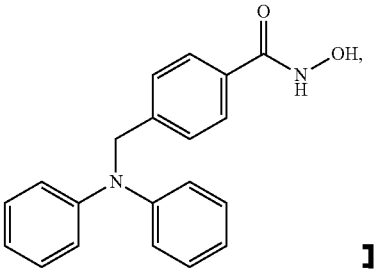
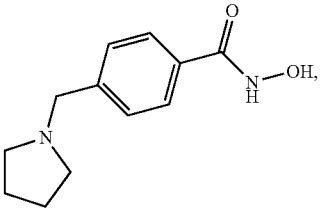
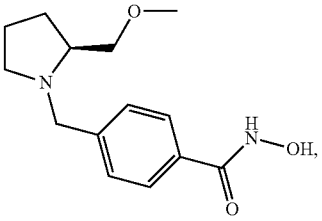
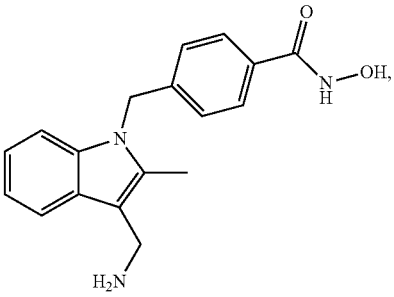
and -continued
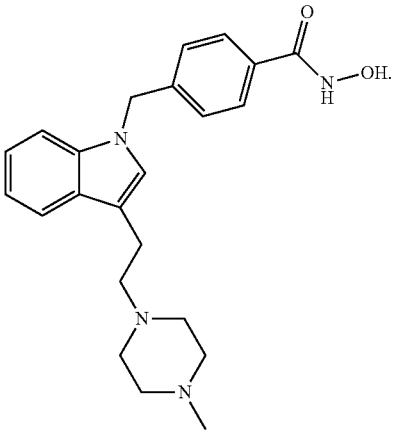
13. A compound having a structure
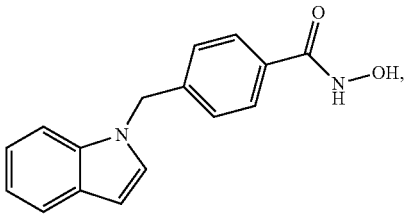
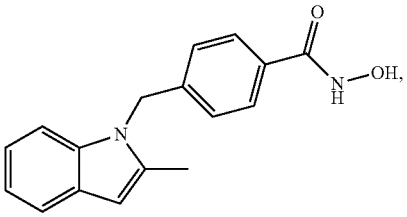
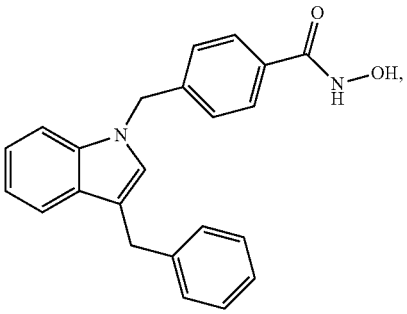
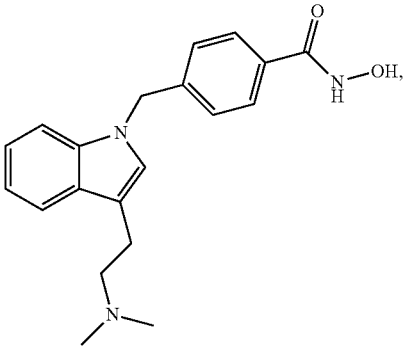
or
-continued
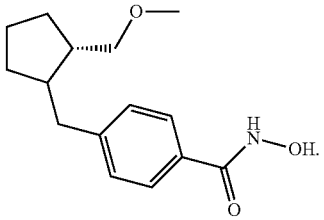
14. A compound having a structure
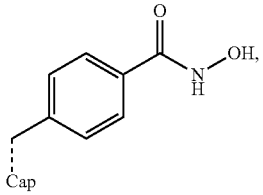
wherein Cap is selected from the group consisting of
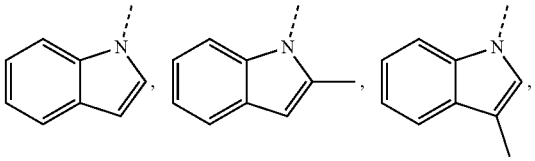
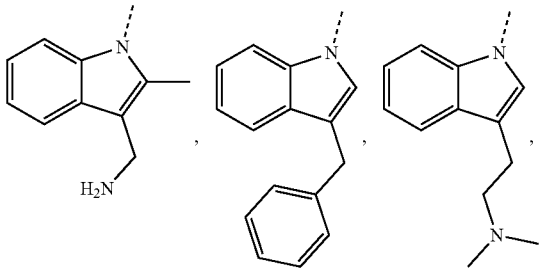
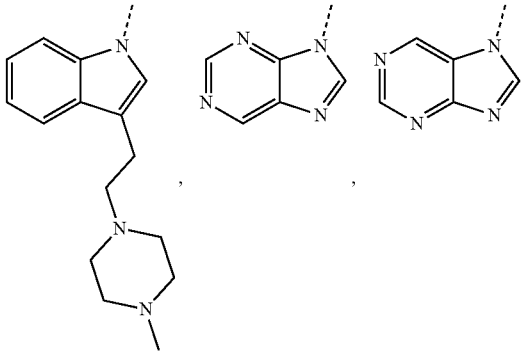
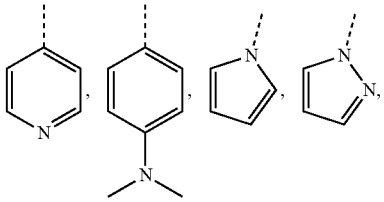

-continued
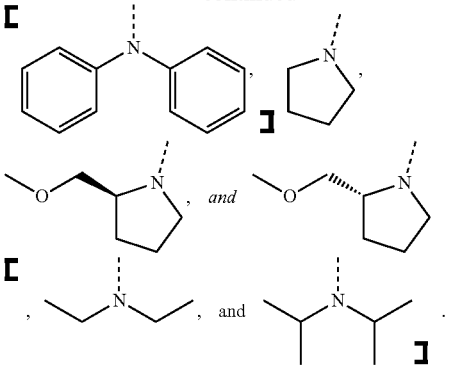
* * * * *